United States Patent
Selby et al.

(10) Patent No.: US 10,167,262 B2
(45) Date of Patent: Jan. 1, 2019

(54) HERBICIDAL SUBSTITUTED 3-ARYLPYRAZOLES

(71) Applicant: FMC CORPORATION, Philadelphia, PA (US)

(72) Inventors: Thomas Paul Selby, Hockessin, DE (US); Stephen Frederick McCann, Newark, DE (US); Andrew Duncan Satterfield, Furlong, PA (US); Kenneth Andrew Hughes, Rising Sun, MD (US); David Andrew Travis, North East, MD (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 15/316,222

(22) PCT Filed: Jun. 5, 2015

(86) PCT No.: PCT/US2015/034362
§ 371 (c)(1),
(2) Date: Dec. 5, 2016

(87) PCT Pub. No.: WO2015/191377
PCT Pub. Date: Dec. 17, 2015

(65) Prior Publication Data
US 2017/0183312 A1 Jun. 29, 2017

Related U.S. Application Data

(60) Provisional application No. 62/010,324, filed on Jun. 10, 2014.

(51) Int. Cl.
| | |
|---|---|
| C07D 231/12 | (2006.01) |
| A01N 43/56 | (2006.01) |
| C07D 231/14 | (2006.01) |
| C07D 401/04 | (2006.01) |
| C07D 409/04 | (2006.01) |
| C07D 403/04 | (2006.01) |
| C07D 409/06 | (2006.01) |

(52) U.S. Cl.
CPC .......... *C07D 231/12* (2013.01); *A01N 43/56* (2013.01); *C07D 231/14* (2013.01); *C07D 401/04* (2013.01); *C07D 403/04* (2013.01); *C07D 409/04* (2013.01); *C07D 409/06* (2013.01)

(58) Field of Classification Search
USPC ......................................................... 504/103
See application file for complete search history.

(56) References Cited

U.S. PATENT DOCUMENTS

| | | | |
|---|---|---|---|
| 5,939,559 A | 8/1999 | Morimoto et al. | |
| 6,030,926 A * | 2/2000 | Morimoto | A01N 43/56 504/280 |

FOREIGN PATENT DOCUMENTS

| | | |
|---|---|---|
| EP | 822187 A1 | 2/1998 |
| WO | 2013/063282 A1 | 5/2013 |

* cited by examiner

*Primary Examiner* — Johann R Richter
*Assistant Examiner* — Courtney A Brown
(74) *Attorney, Agent, or Firm* — Linda D. Birch

(57) ABSTRACT

Disclosed are compounds of Formula 1, including all stereoisomers, N-oxides, and salts thereof,

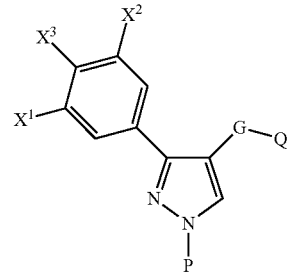

wherein $X^1$, $X^2$, $X^3$, G and Q are as defined in the Summary of the Invention; P is $P^1$ or $P^2$; and $P^1$ and $P^2$ are as defined in the Summary of the Invention. Also disclosed are compositions containing the compounds of Formula 1 and methods for controlling undesired vegetation comprising contacting the undesired vegetation or its environment with an effective amount of a compound or a composition of the invention. Also disclosed is a herbicidal mixture comprising (a) a compound of Formula 1, and (b) at least one additional active ingredient selected from (b1) through (b16); and salts of compounds of (b1) through (b16), wherein (b1) through (b16) are as defined in the disclosure.

5 Claims, No Drawings

HERBICIDAL SUBSTITUTED 3-ARYLPYRAZOLES

FIELD OF THE INVENTION

This invention relates to certain herbicidal substituted 3-arylpyrazoles, their N-oxides, salts and compositions, and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action. U.S. Pat. Nos. 5,939,559 and 6,030,926 disclose certain herbicidal pyrazoles. The substituted herbicidal 3-arylpyrazoles of the present invention are not disclosed in this publication.

SUMMARY OF THE INVENTION

This invention is directed to a compound of Formula 1, including all stereoisomers, N-oxides, and salts thereof, agricultural compositions containing them, and their use as herbicides

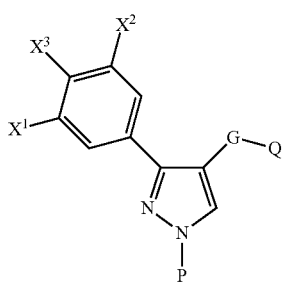

1 wherein
$X^1$ is halogen, $CF_3$, $CF_2H$, $-OCF_3$, $-OCF_2H$, $-SCHF_2$ or $-C\equiv CH$;
$X^2$ is halogen, $CF_3$, $CF_2H$, $-OCF_3$, $-OCF_2H$, $-SCHF_2$ or $-C\equiv CH$;
$X^3$ is H or halogen;
G is $C(=O)$, $C(=NOR^1)$, $C(=NR^{14})$, $C(=NNR^2R^3)$, $C(OR^4)_2$ or $C(SR^4)_2$;
Q is phenyl, 2-thienyl, 3-thienyl, 3-pyridyl or 5-fluoro-3-pyridyl;
P is $P^1$ or $P^2$;
provided when G is $C(=O)$ then P is $P^1$; and when G is $C(=NOR^1)$, $C(=NR^{14})$, $C(=NNR^2R^3)$ or $C(OR^4)_2$ then P is $P^2$;
$P^1$ is $C_1$-$C_7$ alkyl, $C_3$-$C_7$ alkenyl, $C_3$-$C_7$ alkynyl, $C_3$-$C_7$ cycloalkyl, $C_1$-$C_7$ haloalkyl, $C_3$-$C_7$ haloalkenyl, $C_4$-$C_7$ cycloalkylalkyl, $C_4$-$C_7$ haloalkynyl, $C_1$-$C_7$ alkoxy, $C_1$-$C_7$ alkoxyalkyl, $C_3$-$C_7$ alkylcarbonylalkyl, $C_3$-$C_7$ alkoxycarbonylalkyl, $C_4$-$C_7$ halocycloalkylalkyl, $C_2$-$C_7$ haloalkoxyalkyl, $C_2$-$C_7$ alkylthioalkyl, $C_2$-$C_7$ alkylsulfonylalkyl, $C_2$-$C_7$ alkylsulfinylalkyl, $C_2$-$C_7$ haloalkylthioalkyl, $C_2$-$C_7$ haloalkylsulfonylalkyl, $C_2$-$C_7$ haloalkylsulfinylalkyl, $C_3$-$C_7$ haloalkylcarbonylalkyl, $C_2$-$C_7$ alkylaminoalkyl, $C_3$-$C_7$ dialkylaminoalkyl, $C_2$-$C_7$ cyanoalkyl, $C_1$-$C_7$ nitroalkyl, $C(=O)R^5$, $SO_2R^6$, $CO_2R^7$, $C(=O)NR^8R^9$, $SO_2NR^8R^9$, $NH_2$, $OH$, $CH_2OH$, $CH(OR^{10})_2$ or $CH(CO_2CH_3)_2$;
$P^2$ is H, $C_1$-$C_7$ alkyl, $C_3$-$C_7$ alkenyl, $C_3$-$C_7$ alkynyl, $C_3$-$C_7$ cycloalkyl, $C_1$-$C_7$ haloalkyl, $C_3$-$C_7$ haloalkenyl, $C_2$-$C_7$ alkoxyalkyl, $C_4$-$C_7$ cycloalkylalkyl, $C_4$-$C_7$ haloalkynyl, $C_1$-$C_7$ alkoxy, $C_4$-$C_7$ alkoxyalkoxyalkyl, $C_3$-$C_7$ alkylcarbonylalkyl, $C_3$-$C_7$ alkoxycarbonylalkyl, $C_4$-$C_7$ halocycloalkylalkyl, $C_2$-$C_7$ haloalkoxyalkyl, $C_2$-$C_7$ alkylthioalkyl, $C_2$-$C_7$ alkylsulfonylalkyl, $C_2$-$C_7$ alkylsulfinylalkyl, $C_2$-$C_7$ haloalkylthioalkyl, $C_2$-$C_7$ haloalkylsulfonylalkyl, $C_2$-$C_7$ haloalkylsulfinylalkyl, $C_3$-$C_7$ haloalkylcarbonylalkyl, $C_2$-$C_7$ alkylaminoalkyl, $C_3$-$C_7$ dialkylaminoalkyl, $C_2$-$C_7$ cyanoalkyl, $C_1$-$C_7$ nitroalkyl, $C(=O)R^{12}$, $SO_2R^{13}$, $CO_2R^{14}$, $C(=O)NR^{15}R^{16}$, $SO_2NR^{15}R^{16}$, $NH_2$, $OH$, $CH_2OH$, $CH(OR^{17})_2$, $CH(CO_2CH_3)_2$ or $CH(CO_2C_2H_5)_2$;
$R^1$ is H, $C_1$-$C_7$ alkyl;
$R^{14}$ is H, cyano or $C_1$-$C_4$ alkyl;
$R^2$ is H, $C_1$-$C_7$ alkyl;
$R^3$ is $C_1$-$C_7$ alkyl, $C_3$-$C_7$ alkenyl, $C_3$-$C_7$ alkynyl, $C_3$-$C_7$ cycloalkyl, $C_1$-$C_7$ haloalkyl, $C_3$-$C_7$ haloalkenyl, $C_2$-$C_7$ alkoxyalkyl or $C_4$-$C_7$ cycloalkylalkyl; or phenyl optionally substituted by $R^{11}$; or benzyl optionally substituted by $R^{11}$ on ring members; or pyridyl optionally substituted by $R^{11}$; or
$R^2$ and $R^3$ may be taken together as $-(CH_2)_3-$, $-(CH_2)_4-$, $-(CH_2)_5-$ or $-(CH_2)_2O(CH_2)_2-$ to form a ring;
$R^4$ is $C_1$-$C_3$ alkyl; or
two $R^4$ may be taken together as $-(CH_2)_2-$, $-(CH_2)_3-$ or $-CH_2CH(CH_3)-$ to form a ring;
$R^5$ is H, $C_3$-$C_7$ alkenyl, $C_3$-$C_7$ alkynyl, $C_3$-$C_7$ cycloalkyl, $C_1$-$C_7$ haloalkyl, $C_2$-$C_7$ haloalkenyl, $C_2$-$C_7$ alkoxyalkyl or $C_4$-$C_7$ cycloalkylalkyl; or phenyl optionally substituted by $R^{11}$; or benzyl optionally substituted by $R^{11}$ on ring members; or pyridyl optionally substituted by $R^{11}$;
$R^6$ is H, $C_3$-$C_7$ alkenyl, $C_3$-$C_7$ alkynyl, $C_3$-$C_7$ cycloalkyl, $C_1$-$C_7$ haloalkyl, $C_2$-$C_7$ haloalkenyl, $C_2$-$C_7$ alkoxyalkyl or $C_4$-$C_7$ cycloalkylalkyl; or phenyl substituted by $R^{11}$; or benzyl optionally substituted by $R^{11}$ on ring members; or pyridyl optionally substituted by $R^{11}$;
$R^7$ is $C_3$-$C_7$ alkenyl, $C_3$-$C_7$ alkynyl, $C_3$-$C_7$ cycloalkyl, $C_1$-$C_7$ haloalkyl, $C_3$-$C_7$ haloalkenyl, $C_2$-$C_7$ alkoxyalkyl or $C_4$-$C_7$ cycloalkylalkyl; or phenyl optionally substituted by $R^{11}$; or benzyl optionally substituted by $R^{11}$ on ring members; or pyridyl optionally substituted by $R^{11}$;
$R^8$ is H, $C_1$-$C_7$ alkyl;
$R^9$ is H, $C_3$-$C_7$ alkenyl, $C_3$-$C_7$ alkynyl, $C_3$-$C_7$ cycloalkyl, $C_1$-$C_7$ haloalkyl, $C_2$-$C_7$ haloalkenyl, $C_2$-$C_7$ alkoxyalkyl or $C_4$-$C_7$ cycloalkylalkyl; or phenyl optionally substituted by $R^{11}$; or benzyl optionally substituted by $R^{11}$ on ring members; or pyridyl optionally substituted by $R^{11}$;
$R^{11}$ is $C_1$-$C_2$ alkyl, halogen, $C_1$-$C_3$ haloalkyl, $C_1$-$C_3$ haloalkoxy, CN or $C_1$-$C_3$ alkoxy;
$R^{12}$ is H, $C_1$-$C_7$ alkyl, $C_3$-$C_7$ alkenyl, $C_3$-$C_7$ alkynyl, $C_3$-$C_7$ cycloalkyl, $C_1$-$C_7$ haloalkyl, $C_3$-$C_7$ haloalkenyl, $C_2$-$C_7$ alkoxyalkyl or $C_4$-$C_7$ cycloalkylalkyl; or phenyl optionally substituted by $R^{18}$; or benzyl optionally substituted by $R^{18}$ on ring members; or pyridyl optionally substituted by $R^{18}$;

$R^{13}$ is H, $C_1$-$C_7$ alkyl, $C_3$-$C_7$ alkenyl, $C_3$-$C_7$ alkynyl, $C_3$-$C_7$ cycloalkyl, $C_1$-$C_7$ haloalkyl, $C_3$-$C_7$ haloalkenyl, $C_2$-$C_7$ alkoxyalkyl or $C_4$-$C_7$ cycloalkylalkyl; or phenyl optionally substituted by $R^{18}$; or benzyl optionally substituted by $R^{18}$ on ring members; or pyridyl optionally substituted by $R^{18}$;

$R^{14}$ is $C_3$-$C_7$ alkenyl, $C_3$-$C_7$ alkynyl, $C_3$-$C_7$ cycloalkyl, $C_1$-$C_7$ haloalkyl, $C_3$-$C_7$ haloalkenyl, $C_2$-$C_7$ alkoxyalkyl or $C_4$-$C_7$ cycloalkylalkyl; or phenyl optionally substituted by $R^{18}$; or benzyl optionally substituted by $R^{18}$ on ring members; or pyridyl optionally substituted by $R^{18}$;

$R^{15}$ is H, $C_1$-$C_7$ alkyl;

$R^{16}$ is H, $C_1$-$C_7$ alkyl, $C_3$-$C_7$ alkenyl, $C_3$-$C_7$ alkynyl, $C_3$-$C_7$ cycloalkyl, $C_1$-$C_7$ haloalkyl, $C_3$-$C_7$ haloalkenyl, $C_2$-$C_7$ alkoxyalkyl or $C_4$-$C_7$ cycloalkylalkyl; or phenyl optionally substituted by $R^{18}$; or benzyl optionally substituted by $R^{18}$ on ring members; or pyridyl optionally substituted by $R^{18}$;

$R^{17}$ is $C_1$-$C_3$ alkyl; or two $R^{17}$ may be taken together as —$(CH_2)_2$—, —$(CH_2)_3$— or —$CH_2CH(CH_3)$— to form a ring; and $R^{18}$ is $C_1$-$C_2$ alkyl, halogen, $C_1$-$C_3$ haloalkyl, $C_1$-$C_3$ haloalkoxy, CN, $C_1$-$C_3$ alkoxy; provided when i) G is C(=O), $P^1$ is C(=O)$R^5$, $R^5$ is phenyl, $X^1$ is Cl, and $X^2$ is Cl then $X^3$ is other than H, F or Cl;

ii) G is C(=O), $P^1$ is C(=O)$R^5$, $R^5$ is phenyl, $X^1$ is F, $X^2$ is F then $X^3$ is other than H;

iii) G is C(=O), $P^1$ is C(=O)$R^5$, $R^5$ is phenyl, $X^1$ is Br, and $X^2$ is Br, then $X^3$ is other than H or F;

iv) G is C(=O), Q is phenyl, $X^1$ is Cl, $X^2$ is Cl and $X^3$ is H, then $P^1$ is other than $CH_2CF_3$ or $CH_2F$;

v) G is C(=N-pyrr), Q is phenyl, $X^1$ is Cl, $X^2$ is F, and $X^3$ is Cl, then Q is other than $CH_2CF_3$.

More particularly, this invention pertains to a compound of Formula 1 (including all stereoisomers), an N-oxide or a salt thereof. This invention also relates to a herbicidal composition comprising a compound of the invention (i.e. in a herbicidally effective amount) and at least one component selected from the group consisting of surfactants, solid diluents and liquid diluents. This invention further relates to a method for controlling the growth of undesired vegetation comprising contacting the vegetation or its environment with a herbicidally effective amount of a compound of the invention (e.g., as a composition described herein).

This invention also includes a herbicidal mixture comprising (a) a compound selected from Formula 1, N-oxides, and salts thereof, and (b) at least one additional active ingredient selected from (b1) through (b16); and salts of compounds of (b1) through (b16).

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of".

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed.

As referred to herein, the term "broadleaf" used either alone or in words such as "broadleaf weed" means dicot or dicotyledon, a term used to describe a group of angiosperms characterized by embryos having two cotyledons. As used herein, the term "alkylating agent" refers to a chemical compound in which a carbon-containing radical is bound through a carbon atom to a leaving group such as halide or sulfonate, which is displaceable by bonding of a nucleophile to said carbon atom. Unless otherwise indicated, the term "alkylating" does not limit the carbon-containing radical to alkyl; the carbon-containing radicals in alkylating agents include the variety of nitrogen-bound substituent radicals specified for $P^1$, $P^2$.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkoxyalkoxyalkyl" denotes alkoxyalkoxy substitution on alkyl.

"Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$—, $CH_3CH_2S(O)$—, $CH_3CH_2CH_2S(O)$—, $(CH_3)_2CHS(O)$— and the different butylsulfinyl, pentylsulfinyl and hexylsulfinyl isomers. "Alkylsulfinylalkyl" includes alkylsulfinyl substitution on alkyl. Examples of "alkylsulfonyl" include $CH_3S(O)_2$—, $CH_3CH_2S(O)_2$—, $CH_3CH_2CH_2S(O)_2$—, $(CH_3)_2CHS(O)_2$—, and the different butylsulfonyl, pentylsulfonyl and hexylsulfonyl isomers. "Alkylsulfonylalkyl" indicates alkylsulfonyl substitution alkyl. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Cyanoalkyl" denotes an alkyl group substituted with one cyano group. Examples of "cyanoalkyl" include $NCCH_2$—, $NCCH_2CH_2$— and $CH_3CH(CN)CH_2$—. "Nitroalkyl" denotes an alkyl group with on nitro group. "Alkylaminoalkyl", "dialkylaminoalkyl", and the like, are defined analogously to the above examples.

"Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "halocycloalkyl", "haloalkoxy", "haloalkylcarbonylalkyl", "haloalkylthioalkyl", "haloalkylsulfonylalkyl", "haloalkylsulfinylalkyl" "haloalkenyl", "haloalkynyl", and the like, are defined analogously to the term "haloalkyl". Examples of "haloalkoxy" include $CF_3O$—, $CCl_3CH_2O$—, $HCF_2CH_2CH_2O$— and $CF_3CH_2O$—. Examples of "haloalkylthio" include $CCl_3S$—, $CF_3S$—, $CCl_3CH_2S$— and $ClCH_2CH_2CH_2S$—. Examples of "haloalkylsulfinyl" include $CF_3S(O)$—, $CCl_3S(O)$—, $CF_3CH_2S(O)$— and $CF_3CF_2S(O)$—. Examples of "haloalkylsulfonylalkyl" include $CF_3S(O)_2$—, $CCl_3S(O)_2$—, $CF_3CH_2S(O)_2$— and $CF_3CF_2S(O)_2$—. Examples of "haloalkynyl" include $HC\equiv CCHCl$—, $CF_3C\equiv C$—, $CCl_3C\equiv C$— and $FCH_2C\equiv CCH_2$—.

"Alkylcarbonyl" denotes a straight-chain or branched alkyl moieties bonded to a $C(=O)$ moiety. Examples of "alkylcarbonyl" include $CH_3C(=O)$—, $CH_3CH_2CH_2C(=O)$— and $(CH_3)_2CHC(=O)$—. "Alkylcarbonylalkyl" denotes a alkylcarbonyl substitution on an alkyl moiety. Examples of "alkylcarbonylalkyl" include $CH_3C(=O)CH_2$—, $CH_3CH_2CH_2C(=O)CH_2$— and $(CH_3)_2CHC(=O)CH_2CH_2$—. Examples of "alkoxycarbonylalkyl" include $CH_3OC(=O)CH_2CH_2$—, $CH_3CH_2OC(=O)$ $CH_2$—, $CH_3CH_2CH_2OC(=O)$ $CH_2$—, $(CH_3)_2CHOC(=O)$ $CH_2$—.

The total number of carbon atoms in a substituent group is indicated by the "$C_i$-$C_j$" prefix where i and j are numbers from 1 to 7. For example, $C_1$-$C_4$ alkylsulfonyl designates methylsulfonyl through butylsulfonyl; $C_2$ alkoxyalkyl designates $CH_3OCH_2$—; $C_3$ alkoxyalkyl designates, for example, $CH_3CH(OCH_3)$—, $CH_3OCH_2CH_2$— or $CH_3CH_2OCH_2$—; and $C_4$ alkoxyalkyl designates the various isomers of an alkyl group substituted with an alkoxy group containing a total of four carbon atoms, examples including $CH_3CH_2CH_2OCH_2$— and $CH_3CH_2OCH_2CH_2$—.

When a group contains a substituent which can be hydrogen, for example $P^2$, $R^1$, $R^{1\text{-}4}$, $R^5$, $R^6$, $R^8$, $R^9$, $R^{12}$, $R^{15}$ and $R^{16}$, then when this substituent is taken as hydrogen, it is recognized that this is equivalent to said group being unsubstituted. When a variable group is shown to be optionally attached to a position, for example $R^{11}$ and $R^{18}$, then hydrogen may be at the position even if not recited in the variable group definition. When one or more positions on a group are said to be "unsubstituted", then hydrogen atoms are attached to take up any free valency. Unless otherwise indicated, a "ring" as a component of Formula 1 (e.g., substituent $R^3$, $R^5$, $R^6$, $R^7$, $R^9$, $R^{12}$, $R^{13}$ and $R^{14}$) is carbocyclic or heterocyclic. The term "ring member" refers to an atom or other moiety (e.g., $C(=O)$, $C(=S)$, $S(O)$ or $S(O)_2$) forming the backbone of a ring or ring system.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

As noted above, Q can be phenyl, 2-thienyl, 3-thienyl, 3-pyridyl or 5-fluoro-3-pyridyl. Examples of phenyl, 2-thienyl, 3-thienyl, 3-pyridyl or 5-fluoro-3-pyridyl are illustrated in Exhibit 1 as U-1 through U-5.

Exhibit 1

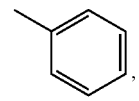,

U-1

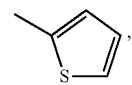,

U-2

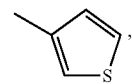,

U-3

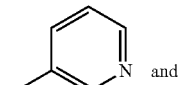 and

U-4

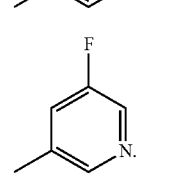.

U-5

As noted above, G can be (inter alia) $C(OR^4)_2$ or $C(SR^4)_2$, and "two $R^4$ may be taken together as —$(CH_2)_2$—, —$(CH_2)_3$— or —$CH_2CH(CH_3)$— to form a ring" When two $R^4$ are taken together with the oxygen or sulfur atoms to which they are attached. said ring is a 5- or 6-membered ring. The resulting ring consists of the recited $R^4$ value, the oxygen or sulfer atoms connected to the carbon atom, which is bonded to the remainder of Formula 1 and Q. Examples of when G is $C(OR^4)_2$ or $C(SR^4)_2$ and two $R^4$ are taken together include U-6 through U-10 where the bond projecting to the left is connected to the remainder of Formula 1.

U-6

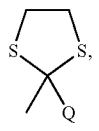

U-7

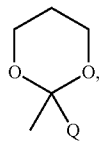

U-8

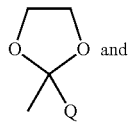

U-9

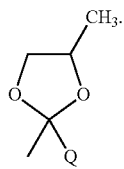

U-10

As referred to herein, U-6 is known as 1,3-dithianyl, U-7 as 1,3-dithiolanyl, U-8 as 1,3-dioxanyl, U-9 as 1,3-dioxolanyl, and U-10 as 4-methyl-1,3-dioxolanyl.

As noted above, G can be (inter alia) $C(=NNR^2R^3)$ and "$R^2$ and $R^3$ may be taken together as —$(CH_2)_2$—, —$(CH_2)_3$—, —$(CH_2)_4$— or —$(CH_2)_2O(CH_2)_2$— to form a ring". When $R^2$ and $R^3$ are taken together as a ring, said ring is a 4-, 5- or 6-membered ring. The resulting ring consists of the recited $R^2$ and $R^3$ value and the nitrogen atom to which they are attached. Examples of when two $R^2$ and $R^3$ are taken together as a ring include U-11 through U-14 where the bond projecting to the left is connected to the remainder of Formula 1.

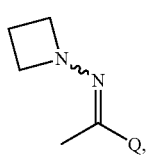

U-11

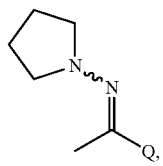

U-12

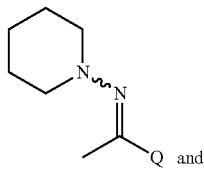

U-13

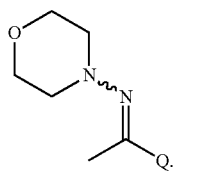

U-14

The ring depicted for U-11 is referred to as a N-azetidinyl, the ring depicted in U-12 as N-pyrrolidinyl, U-13 as N-piperidinyl, and U-14 as N-morpholinyl.

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

Compounds of Formula 1 (when P is H) can also as be isolated as the tautomeric mixture of Formula 1A and 1A' under certain reaction conditions.

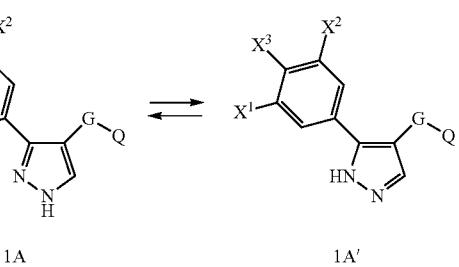

1A  1A'

The Summary of the Invention and any Embodiments herein refer to either tautomer so long as the presence of the tautomer 1A' does not detract from the biological activity of the compound of the invention. When a compound of Formula 1A or 1A' are alkylated or capped with electrophiles, the predominant product is generally that from one or the other tautomer, however either "N-alkylated" tautomer isomer can be isolated using routing techniques known to one skilled in the art. In general, the tautomer represented by Formula 1A is known to impart the most biological activity.

Compounds of Formula 1 can comprise additional chiral centers. For example, substituents and other molecular constituents (such as P) may contain chiral centers. This invention comprises racemic mixtures as well as enriched and essentially pure stereoconfigurations at these additional chiral centers. Compounds of this invention can exist as one or more conformational isomers due to restricted rotation about the amide bond (e.g., —C(=O)(2- and/or 6-fluorophenyl) in Formula 1. This invention comprises mixtures of conformational isomers. In addition, this invention includes compounds that are enriched in one conformer relative to others.

Compounds of Formula 1 typically exist in more than one form, and Formula 1 thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Embodiments of the present invention as described in the Summary of the Invention include (where Formula 1 as used in the following Embodiments includes N-oxides and salts thereof):

Embodiment 1

A compound of Formula 1 as described in the Summary of the Invention.

Embodiment 2

A compound of Embodiment 1 wherein $X^1$ is halogen, $CF_3$, $CF_2H$, —$OCF_3$ or —$OCF_2H$.

Embodiment 3

A compound of Embodiment 2 wherein $X^1$ is halogen or $CF_3$.

Embodiment 4

A compound of Embodiment 3 wherein $X^1$ is halogen.

Embodiment 5

A compound of Embodiment 4 wherein $X^1$ is Cl or Br.

Embodiment 6

A compound of Embodiment 5 wherein $X^1$ is Cl.

Embodiment 7

A compound of any one of Embodiments 1 through 6 wherein $X^2$ is halogen, $CF_3$, $CF_2H$, $-OCF_3$ or $-OCF_2H$.

Embodiment 8

A compound of Embodiments 7 wherein $X^2$ is halogen or $CF_3$.

Embodiment 9

A compound of Embodiment 8 wherein $X^2$ is halogen.

Embodiment 10

A compound of Embodiment 9 wherein $X^2$ is Cl or Br.

Embodiment 11

A compound of Embodiment 10 wherein $X^2$ is Cl.

Embodiment 12

A compound of any one of Embodiments A1 through A11 wherein $X^3$ is H, F, Cl or Br.

Embodiment 13

A compound of Embodiment 12 wherein $X^3$ is H, F or Cl.

Embodiment 14

A compound of Embodiment 13 wherein $X^3$ is H or Cl.

Embodiment 15

A compound of Embodiment 14 wherein $X^3$ is H.

Embodiment 16

A compound of Embodiment 14 wherein $X^3$ is Cl.

Embodiment 17

A compound of any one of Embodiments 1 through 16 wherein Q is phenyl, 2-thienyl or 3-thienyl.

Embodiment 18

A compound of Embodiment 17 wherein Q is phenyl or 2-thienyl.

Embodiment 19

A compound of Embodiment 18 wherein Q is phenyl.

Embodiment 20

A compound of Embodiment 19 wherein Q is 2-thienyl.

Embodiment 21

A compound of any one of Embodiments 1 through 20 wherein G is $C(=O)$, $C(=NOR^1)$, $C(=NNR^2R^3)$ or $C(OR^4)_2$.

Embodiment 22

A compound of Embodiment 21 wherein G is $C(=O)$.

Embodiment 23

A compound of Embodiment 21 wherein G is $C(=NOR^1)$, $C(=NNR^2R^3)$ or $C(OR^4)_2$.

Embodiment 24

A compound of Embodiment 23 wherein G is $C(=NNR^2R^3)$ or $C(OR^4)_2$.

Embodiment 25

A compound of Embodiment 24 wherein G is $C(OR^4)_2$.

Embodiment 26

A compound of any one of Embodiments 1 through 22 wherein P is $P^1$.

Embodiment 27

A compound of Embodiment 26 wherein $P^1$ is $C_1$-$C_7$ alkyl, $C_3$-$C_7$ alkenyl, $C_3$-$C_7$ alkynyl, $C_1$-$C_7$ alkoxyalkyl, $C(=O)R^5$, $SO_2R^6$, $CO_2R^7$, $C(=O)NR^8R^9$, $SO_2NR^8R^9$, $NH_2$, OH, $CH_2OH$, $CH(OR^{10})_2$ or $CH(CO_2CH_3)_2$.

Embodiment 28

A compound of Embodiment 27 wherein $P^1$ is $C_1$-$C_4$ alkyl, $C_3$-$C_4$ alkenyl, $C_3$-$C_4$ alkynyl, $CH_2OCH_3$, $C(=O)CH_2OCH_3$, $SO_2CF_3$ or $CH_2OH$.

Embodiment 29

A compound of Embodiment 28 wherein $P^1$ is $C_1$-$C_4$ alkyl, $C_3$-$C_4$ alkenyl, $C_3$-$C_4$ alkynyl, $CH_2OCH_3$, $C(=O)CH_2OCH_3$ or $CH_2OH$.

Embodiment 30

A compound of Embodiment 29 wherein $P^1$ is $CH_3$.

Embodiment 31

A compound of Embodiment 29 wherein $P^1$ is $CH_2CH_3$.

Embodiment 32

A compound of Embodiment 29 wherein $P^1$ is $CH=CH_2$.

Embodiment 33

A compound of Embodiment 29 wherein $P^1$ is $-C\equiv CH$.

Embodiment 34

A compound of Embodiment 29 wherein $P^1$ is $CH_2OCH_3$.

Embodiment 35

A compound of Embodiment 29 wherein $P^1$ is $C(=O)CH_2OCH_3$.

Embodiment 36

A compound of Embodiment 29 wherein $P^1$ is $CH_2OH$.

Embodiment 37

A compound of any one of Embodiments 1 through 21 or 23 through 25 wherein P is $P^2$.

Embodiment 38

A compound of Embodiment 37 wherein $P^2$ is H, $C_1$-$C_7$ alkyl, $C_3$-$C_7$ alkenyl, $C_3$-$C_7$ alkynyl, $C_3$-$C_7$ cycloalkyl, $C_1$-$C_7$ haloalkyl, $C_3$-$C_7$ haloalkenyl, $C_2$-$C_7$ alkoxyalkyl, $C(=O)R^{12}$, $SO_2R^{13}$, $CO_2R^{14}$, $C(=O)NR^{15}R^{16}$, $SO_2NR^{15}R^{16}$, $NH_2$, OH or $CH_2OH$.

Embodiment 39

A compound of Embodiment 39 wherein $P^2$ is H, $C_1$-$C_4$ alkyl, —$CH_2C\equiv CH$ or $C(=O)R^{12}$.

Embodiment 40

A compound of Embodiment 39 wherein $P^2$ is H.

Embodiment 41

A compound of Embodiment 39 wherein $P^2$ is —$CH_2C\equiv CH$.

Embodiment 42

A compound of Embodiment 39 wherein $P^2$ is $C(=O)CH_3$.

Embodiment 43

A compound of Embodiment 39 wherein $P^2$ is $C(=O)CH_2CH_3$.

Embodiment 44

A compound of any one of Embodiments 1 through 21, 22, or 37 through 43 wherein $R^1$ is H, $CH_3$ or $CH_2CH_3$.

Embodiment 45

A compound of Embodiments 44 wherein $R^1$ is $CH_3$ or $CH_2CH_3$.

Embodiment 46

A compound of Embodiments 45 wherein $R^1$ is $CH_3$.

Embodiment 47

A compound of any one of Embodiments 1 through 21, 22, or 37 through 43 wherein $R^2$ is H, $CH_3$ or $CH_2CH_3$.

Embodiment 48

A compound of Embodiment 47 wherein $R^2$ is H or $CH_3$.

Embodiment 49

A compound of Embodiment 48 wherein $R^2$ is H.

Embodiment 50

A compound of any one of Embodiments 1 through 21, 22, or 37 through 43 wherein $R^3$ is $C_1$-$C_7$ alkyl; or benzyl optionally substituted by $R^{11}$ on ring members.

Embodiment 51

A compound of Embodiment 50 wherein $R^3$ is $CH_2CH_3$; or benzyl optionally substituted by $R^{11}$ on ring members.

Embodiment 52

A compound of Embodiment 51 wherein $R^3$ is $CH_2CH_3$; or benzyl (i.e. unsubstituted benzyl).

Embodiment 53

A compound of any one of Embodiments 1 through 21, 22, or 37 through 43 wherein when $R^2$ and $R^3$ are taken together, they are taken together as —$(CH_2)_4$— or —$(CH_2)_2O(CH_2)_2$— to form a ring.

Embodiment 54

A compound of Embodiment 50 wherein when $R^2$ and $R^3$ are taken together, they are taken together as —$(CH_2)_4$— to form a ring.

Embodiment 55

A compound of any one of Embodiments 1 through 21, 22, or 37 through 43 wherein $R^4$ is $CH_3$ or $CH_2CH_3$.

Embodiment 56

A compound of Embodiment 55 wherein $R^4$ is $CH_2CH_3$.

Embodiment 57

A compound of any one of Embodiments 1 through 21, 22, or 37 through 43 wherein when two $R^4$ are taken together, they are taken together as —$(CH_2)_2$— or —$(CH_2)_3$— to form a ring.

Embodiment 58

A compound of any one of Embodiments 1 through 22, or 26 through 36 wherein $R^5$ is $C_1$-$C_7$ haloalkyl or $C_2$-$C_7$ alkoxyalkyl.

Embodiment 59

A compound of Embodiment 58 wherein $R^5$ is $CF_3$ or $CH_2OCH_3$.

Embodiment 60

A compound of Embodiment 59 wherein $R^5$ is $CH_2OCH_3$.

Embodiment 61

A compound of any one of Embodiments 1 through 22, or 26 through 36 wherein $R^6$ is $C_3$-$C_7$ cycloalkyl or $C_1$-$C_7$ haloalkyl.

Embodiment 62

A compound of Embodiment 61 wherein $R^6$ is c-Pr or $CF_3$.

Embodiment 63

A compound of Embodiment 62 wherein $R^6$ is $CF_3$.

Embodiment 64

A compound of any one of Embodiments 1 through 22, or 26 through 36 wherein $R^7$ is $C_3$-$C_7$ alkenyl, $C_3$-$C_7$ cycloalkyl or $C_1$-$C_7$ haloalkyl.

Embodiment 65

A compound of Embodiment 64 wherein $R^7$ is $CH=CH_2$, c-Pr or $CF_3$.

Embodiment 66

A compound of Embodiment 65 wherein $R^7$ is $CF_3$.

Embodiment 67

A compound of any one of Embodiments 1 through 22, or 26 through 36 wherein $R^8$ is H, $CH_3$ or $CH_2CH_3$.

Embodiment 68

A compound of Embodiment 67 wherein $R^8$ is H or $CH_3$.

Embodiment 69

A compound of Embodiment 68 wherein $R^8$ is H.

Embodiment 70

A compound of any one of Embodiments 1 through 22, or 26 through 36 wherein $R^9$ is H, $C_3$-$C_7$ alkenyl, $C_3$-$C_7$ cycloalkyl, $C_2$-$C_7$ alkoxyalkyl or $C_4$-$C_7$ cycloalkylalkyl; or benzyl optionally substituted by $R^{11}$ on ring members.

Embodiment 71

A compound of Embodiment 70 wherein $R^9$ is H or $C_3$-$C_7$ cycloalkyl.

Embodiment 72

A compound of Embodiment 71 wherein $R^9$ is H or c-Pr.

Embodiment 73

A compound of any one of Embodiments 1 through 22, or 26 through 36 wherein $R^{10}$ is $CH_3$ or $CH_2CH_3$.

Embodiment 74

A compound of Embodiment 73 wherein $R^{10}$ is $CH_2CH_3$.

Embodiment 75

A compound of any one of Embodiments 1 through 22, or 26 through 36 wherein when two $R^{10}$ are taken together, they are taken together as $—(CH_2)_2—$ or $—(CH_2)_3—$ to form a ring.

Embodiment 76

A compound of any one of Embodiments 1 through 75 wherein $R^{11}$ is $CH_3$, $CH_2CH_3$, F, Cl, $CF_3$, $OCH_3$ or CN.

Embodiment 77

A compound of Embodiment 76 wherein $R^{11}$ is $CH_3$, F, Cl, $OCH_3$ or CN.

Embodiment 78

A compound of Embodiment 77 wherein $R^{11}$ is Cl or $OCH_3$.

Embodiment 79

A compound of any one of Embodiments 1 through 25 or 37 through 43 wherein $R^{12}$ is $C_1$-$C_7$ alkyl or $C_2$-$C_7$ alkoxyalkyl.

Embodiment 80

A compound of Embodiment 79 wherein $R^{12}$ is $CH_3$, $CH_2CH_3$ or $CH_2OCH_3$.

Embodiment 81

A compound of Embodiment 80 wherein $R^{12}$ is $CH_3$ or $CH_2CH_3$.

Embodiment 82

A compound of any one of Embodiments 1 through 25 or 37 through 43 wherein $R^{13}$ is H, $C_1$-$C_7$ alkyl or $C_1$-$C_7$ haloalkyl.

Embodiment 83

A compound of Embodiment 82 wherein $R^{13}$ is H, $CH_3$ or $CH_2CH_3$ or $CF_3$.

Embodiment 84

A compound of Embodiment 83 wherein $R^{13}$ is $CF_3$.

Embodiment 85

A compound of Embodiment 1 through 25 or 37 through 43 wherein $R^{14}$ is $C_3$-$C_7$ alkenyl or $C_3$-$C_7$ cycloalkyl.

Embodiment 86

A compound of Embodiment 85 wherein $R^{14}$ is $CH=CH_2$ or c-Pr.

Embodiment 87

A compound of Embodiment 86 wherein $R^{14}$ is c-Pr.

Embodiment 88

A compound of any one of Embodiments 1 through 25 or 37 through 43 wherein $R^{15}$ is H, $CH_3$ or $CH_2CH_3$.

Embodiment 89

A compound of Embodiments 88 wherein $R^{15}$ is H or $CH_3$.

Embodiment 90

A compound of Embodiments 89 wherein $R^{15}$ is H.

Embodiment 91

A compound of any one of Embodiments 1 through 25 or 37 through 43 wherein $R^{16}$ is H, $C_3$-$C_7$ alkenyl, $C_3$-$C_7$ cycloalkyl, $C_2$-$C_7$ alkoxyalkyl or $C_4$-$C_7$ cycloalkylalkyl; or benzyl optionally substituted by $R^{11}$ on ring members.

Embodiment 92

A compound of Embodiment 91 wherein $R^{16}$ is H or $C_3$-$C_7$ cycloalkyl.

Embodiment 93

A compound of Embodiment 91 wherein $R^{16}$ is H or c-Pr.

Embodiment 94

A compound of any one of Embodiments 1 through 25 or 37 through 43 wherein $R^{17}$ is $CH_3$ or $CH_2CH_3$.

Embodiment 95

A compound of Embodiment 94 wherein $R^{17}$ is $CH_2CH_3$.

Embodiment 96

A compound of any one of Embodiments 1 through 25 or 37 through 43 wherein when two $R^{17}$ are taken together, they are taken together as —$(CH_2)_2$— or —$(CH_2)_3$— to form a ring.

Embodiment 97

A compound of any one of Embodiments 1 through 96 wherein $R^{18}$ is $CH_3$, $CH_2CH_3$, F, Cl, $CF_3$, $OCH_3$ or CN.

Embodiment 98

A compound of Embodiment 97 wherein $R^{18}$ is $CH_3$, F, Cl, $OCH_3$ or CN.

Embodiment 99

A compound of Embodiment 98 wherein $R^{18}$ is Cl or $OCH_3$.

Embodiments of this invention, including Embodiments 1-99 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-99 above as well as any other embodiments described herein, and any combination thereof, pertain to the compositions and methods of the present invention.

Combinations of Embodiments 1 through 99 are illustrated by:

Embodiment A

A compound of Formula 1 wherein
Q is phenyl, 2-thienyl or 3-thienyl;
G is C(=O), C(=$NOR^1$), C(=$NNR^2R^3$) or $C(OR^4)_2$;
$P^1$ is $C_1$-$C_7$ alkyl, $C_3$-$C_7$ alkenyl, $C_3$-$C_7$ alkynyl, $C_1$-$C_7$ alkoxyalkyl, C(=O)$R^5$, $SO_2R^6$, $CO_2R^7$, C(=O)$NR^8R^9$, $SO_2NR^8R^9$, $NH_2$, OH, $CH_2OH$, $CH(OR^{10})_2$ or $CH(CO_2CH_3)_2$;
$P^2$ is H, $C_1$-$C_7$ alkyl, $C_3$-$C_7$ alkenyl, $C_3$-$C_7$ alkynyl, $C_3$-$C_7$ cycloalkyl, $C_1$-$C_7$ haloalkyl, $C_3$-$C_7$ haloalkenyl, $C_2$-$C_7$ alkoxyalkyl, C(=O)$R^{12}$, $SO_2R^{13}$, $CO_2R^{14}$, C(=O)$NR^{15}R^{16}$, $SO_2NR^{15}R^{16}$, $NH_2$, OH or $CH_2OH$;
$R^1$ is H, $CH_3$ or $CH_2CH_3$;
$R^2$ is H, $CH_3$ or $CH_2CH_3$;
$R^3$ is $C_1$-$C_7$ alkyl; or benzyl optionally substituted by $R^{11}$ on ring members; or
$R^2$ and $R^3$ are taken together as —$(CH_2)_4$— or —$(CH_2)_2O(CH_2)_2$— to form a ring;
$R^4$ is $CH_3$ or $CH_2CH_3$;
$R^5$ is $C_1$-$C_7$ haloalkyl or $C_2$-$C_7$ alkoxyalkyl;
$R^6$ is $C_3$-$C_7$ cycloalkyl or $C_1$-$C_7$ haloalkyl;
$R^7$ is $C_3$-$C_7$ alkenyl, $C_3$-$C_7$ cycloalkyl or $C_1$-$C_7$ haloalkyl;
$R^8$ is H, $CH_3$ or $CH_2CH_3$;
$R^9$ is H, $C_3$-$C_7$ alkenyl, $C_3$-$C_7$ cycloalkyl, $C_2$-$C_7$ alkoxyalkyl or $C_4$-$C_7$ cycloalkylalkyl; or benzyl optionally substituted by $R^{11}$ on ring members
$R^{10}$ is $CH_3$ or $CH_2CH_3$;
$R^{11}$ is $CH_3$, $CH_2CH_3$, F, Cl, $CF_3$, $OCH_3$ or CN;
$R^{12}$ is $C_1$-$C_7$ alkyl or $C_2$-$C_7$ alkoxyalkyl;
$R^{13}$ is H, $C_1$-$C_7$ alkyl or $C_1$-$C_7$ haloalkyl;
$R^{14}$ is $C_3$-$C_7$ alkenyl or $C_3$-$C_7$ cycloalkyl;
$R^{15}$ is H, $CH_3$ or $CH_2CH_3$; and
$R^{16}$ is H, $C_3$-$C_7$ alkenyl, $C_3$-$C_7$ cycloalkyl, $C_2$-$C_7$ alkoxyalkyl or $C_4$-$C_7$ cycloalkylalkyl; or benzyl optionally substituted by $R^{11}$ on ring members.

Embodiment B

A compound of Embodiment A wherein
$X^1$ is halogen, $CF_3$, $CF_2H$, —$OCF_3$ or —$OCF_2H$;
$X^2$ is halogen, $CF_3$, $CF_2H$, —$OCF_3$ or —$OCF_2H$;
$X^3$ is H, F, Cl or Br;
G is C(=O);
Q is phenyl or 2-thienyl; and
$P^1$ is $C_1$-$C_4$ alkyl, $C_3$-$C_4$ alkenyl, $C_3$-$C_4$ alkynyl, $CH_2OCH_3$, C(=O)$CH_2OCH_3$, $SO_2CF_3$ or $CH_2OH$.

Embodiment C

A compound of Embodiment B wherein
$X^1$ is halogen or $CF_3$;
$X^2$ is halogen or $CF_3$;
$X^3$ is H, F or Cl; and
$P^1$ is $C_1$-$C_4$ alkyl, $C_3$-$C_4$ alkenyl, $C_3$-$C_4$ alkynyl, $CH_2OCH_3$, C(=O)$CH_2OCH_3$ or $CH_2OH$.

Embodiment D

A compound of Embodiment C wherein
$X^1$ is halogen;
$X^2$ is halogen; and
$X^3$ is H, F or Cl.

Embodiment E

A compound of Embodiment A wherein
$X^1$ is halogen, $CF_3$, $CF_2H$, $-OCF_3$ or $-OCF_2H$;
$X^2$ is halogen, $CF_3$, $CF_2H$, $-OCF_3$ or $-OCF_2H$;
$X^3$ is H, F, Cl or Br;
G is $C(=NOR^1)$, $C(=NNR^2R^3)$ or $C(OR^4)_2$;
Q is phenyl or 2-thienyl;
$P^2$ is H, $C_1$-$C_4$ alkyl, $-CH_2C\equiv CH$ or $C(=O)R^{12}$;
$R^1$ is $CH_3$ or $CH_2CH_3$;
$R^2$ is H or $CH_3$;
$R^3$ is $CH_2CH_3$; or benzyl optionally substituted by $R^{11}$ on ring members; and
$R^4$ is $CH_2CH_3$;
$R^{11}$ is $CH_3$, F, Cl, $OCH_3$ or CN; and
$R^{12}$ is $CH_3$, $CH_2CH_3$ or $CH_2OCH_3$.

Embodiment F

A compound of Embodiment E wherein
$X^1$ is halogen or $CF_3$;
$X^2$ is halogen or $CF_3$;
$X^3$ is H, F or Cl;
G is $C(=NNR^2R^3)$ or $C(OR^4)_2$;
$P^2$ is H;
$R^2$ is H;
$R^3$ is $CH_2CH_3$; or benzyl.

Embodiment G

A compound of Embodiment F wherein
$X^1$ is halogen;
$X^2$ is halogen;
$X^3$ is H, F or Cl; and
G is $C(OR^4)_2$.

Specific embodiments include a compound of Formula 1 selected from the group consisting of
[3-(3,5-dichlorophenyl)-1-methyl-1H-pyrazol-4-yl]phenylmethanone (Compound 54);
[3-(3,5-dichlorophenyl)-1-ethyl-1H-pyrazol-4-yl]phenylmethanone (Compound 31);
[3-(3,5-dichlorophenyl)-1-propyl-1H-pyrazol-4-yl]phenylmethanone (Compound 61);
[3-(3,5-dichlorophenyl)-1-(2-propyn-1-yl)-1H-pyrazol-4-yl]phenylmethanone (Compound 39);
N-[[3-(3,5-dichlorophenyl)-1H-pyrazol-4-yl]phenylmethylene]-1-pyrrolidinamine (Compound 30);
[3-(3,5-dichlorophenyl)-1-(hydroxymethyl)-1H-pyrazol-4-yl]phenylmethanone (Compound 15);
1-[4-benzoyl-3-(3,5-dichlorophenyl)-1H-pyrazol-1-yl]-2-methoxyethanone (Compound 16);
3-(3,5-dichlorophenyl)-1-[(trifluoromethyl)sulfonyl]-1H-pyrazol-4-yl]phenylmethanone (Compound 2);
3-(3,5-dichlorophenyl)-4-(diethoxyphenylmethyl)-1H-pyrazole (Compound 14); and
3-(3,5-dichlorophenyl)-4-(dimethoxyphenylmethyl)-1H-pyrazole (Compound 13).

This invention also relates to a method for controlling undesired vegetation comprising applying to the locus of the vegetation herbicidally effective amounts of the compounds of the invention (e.g., as a composition described herein). Of note as embodiments relating to methods of use are those involving the compounds of embodiments described above. Compounds of the invention are particularly useful for selective control of weeds such as lambsquarters, velvetleaf, chickweed, pigweed, ragweed and waterhemp in crops such as wheat, barley, maize, soybean, sunflower, cotton, oilseed rape and rice, and specialty crops such as sugarcane, citrus, fruit and nut crops.

Also noteworthy as embodiments are herbicidal compositions of the present invention comprising the compounds of embodiments described above.

This invention also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics and (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, metam, methyldymron, oleic acid, oxaziclomefone, pelargonic acid and pyributicarb, and (b16) herbicide safeners; and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, desmetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol, pyridate, siduron, simazine, simetryn, tebuthiuron, terbacil, terbumeton, terbuthylazine, terbutryn and trietazine.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for DNA synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-sodium, foramsulfuron, halosulfuron-methyl, imazamethabenz-methyl, imazamox, imazapic, imazapyr, imazaquin, imazethapyr, imazosulfuron, iodosulfuron-methyl (including sodium salt), iofensulfuron (2-iodo-N-[[(4-methoxy-6-methyl-1,3,5-triazin-2-yl)amino]carbonyl]benzenesulfonamide), mesosulfuron-methyl, metazosulfuron (3-chloro-4-(5,6-dihydro-5-methyl-1,4,2-dioxazin-3-yl)-N-[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuron-methyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethanesulfonamide), triasulfuron, tribenuron-methyl, trifloxysulfuron (including sodium salt), triflusulfuron-methyl and tritosulfuron.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate.

"EPSP (5-enol-pyruvylshikimate-3-phosphate) synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, tiafenacil (methyl N-[2-[[2-chloro-5-[3,6-dihydro-3-methyl-2,6-dioxo-4-(trifluoromethyl)-1(2H)-pyrimidinyl]-4-fluorophenyl]thio]-1-oxopropyl]-β-alaninate) and 3-[7-fluoro-3,4-dihydro-3-oxo-4-(2-propyn-1-yl)-2H-1,4-benzoxazin-6-yl]dihydro-1,5-dimethyl-6-thioxo-1,3,5-triazine-2,4(1H,3H)-dione.

"GS (glutamine synthase) inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P ((2S)-2-amino-4-(hydroxymethylphosphinyl)butanoic acid) and bilanaphos.

"VLCFA (very long chain fatty acid) elongase inhibitors" (b9) are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[(2,5-dichloro-4-ethoxyphenyl)methyl]sulfonyl]-4,5-dihydro-5,5-dimethylisoxazole), fentrazamide, flufenacet, indanofan, mefenacet, metazachlor, metolachlor, naproanilide, napropamide, napropamide-M ((2R)—N,N-diethyl-2-(1-naphthalenyloxy)propanamide), pethoxamid, piperophos, pretilachlor, propachlor, propisochlor, pyroxasulfone, and thenylchlor, including resolved forms such as S-metolachlor and chloroacetamides and oxyacetamides.

"Auxin transport inhibitors" (b10) are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS (phytoene desaturase inhibitors) (b11) are chemical compounds that inhibit carotenoid biosynthesis pathway at the phytoene desaturase step. Examples of PDS inhibitors include beflubutamid, diflufenican, fluridone, flurochloridone, flurtamone norflurzon and picolinafen.

"HPPD (4-hydroxyphenyl-pyruvate dioxygenase) inhibitors" (b12) are chemical substances that inhibit the biosynthesis of synthesis of 4-hydroxyphenyl-pyruvate dioxygenase. Examples of HPPD inhibitors include benzobicyclon, benzofenap, bicyclopyrone (4-hydroxy-3-[[2-[(2-methoxyethoxy)methyl]-6-(trifluoromethyl)-3-pyridinyl]carbonyl]bicyclo[3.2.1]oct-3-en-2-one), fenquinotrione (2-[[8-chloro-3,4-dihydro-4-(4-methoxyphenyl)-3-oxo-2-quinoxalinyl]carbonyl]-1,3-cyclohexanedione), isoxachlortole, isoxaflutole, mesotrione, pyrasulfotole, pyrazolynate, pyrazoxyfen, sulcotrione, tefuryltrione, tembotrione, topramezone, 5-chloro-3-[(2-hydroxy-6-oxo-1-cyclohexen-1-yl)carbonyl]-1-(4-methoxyphenyl)-2(1H)-quinoxalinone, 4-(2,6-diethyl-4-methylphenyl)-5-hydroxy-2,6-dimethyl-3(2H)-pyridazinone, 4-(4-fluorophenyl)-6-[(2-hydroxy-6-oxo-1-cyclohexen-1-yl)carbonyl]-2-methyl-1,2,4-triazine-3,5(2H,4H)-dione, 5-[(2-hydroxy-6-oxo-1-cyclohexen-1-yl)carbonyl]-2-(3-methoxyphenyl)-3-(3-methoxypropyl)-4(3H)-pyrimidinone, 2-methyl-N-(4-methyl-1,2,5-oxadiazol-3-yl)-3-(methylsulfinyl)-4-(trifluoromethyl)benzamide and 2-methyl-3-(methylsulfonyl)-N-(1-methyl-1H-tetrazol-5-yl)-4-(trifluoromethyl)benzamide.

HST (homogentisate solenesyltransererase) inhibitors (b13) disrupt a plant's ability to convert homogentisate to 2-methyl-6-solanyl-1,4-benzoquinone, thereby disrupting carotenoid biosynthesis. Examples of HST inhibitors include haloxydine, pyriclor, 3-(2-chloro-3,6-difluorophenyl)-4-hydroxy-1-methyl-1,5-naphthyridin-2(1H)-one, dichloro-4-pyridinyl)-5-(2,2-difluoroethyl)-8-hydroxy-pyrido[2,3-b]pyrazin-6(5H)-one and 4-(2,6-diethyl-4-methylphenyl)-5-hydroxy-2,6-dimethyl-3(2H)-pyridazinone.

HST inhibitors also include compounds of Formulae A and B.

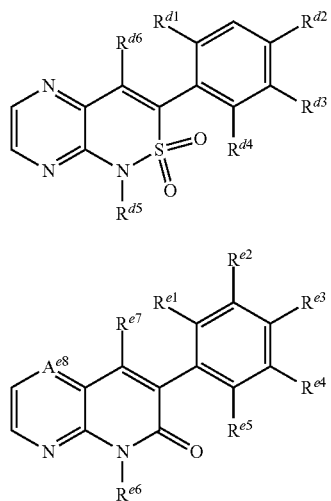

wherein $R^{d1}$ is H, Cl or $CF_3$; $R^{d2}$ is H, Cl or Br; $R^{d3}$ is H or Cl; $R^{d4}$ is H, Cl or $CF_3$; $R^{d5}$ is $CH_3$, $CH_2CH_3$ or $CH_2CHF_2$; and $R^{d6}$ is OH, or —OC(═O)-i-Pr; and $R^{e1}$ is H, F, Cl, $CH_3$ or $CH_2CH_3$; $R^{e2}$ is H or $CF_3$; $R^{e3}$ is H, $CH_3$ or $CH_2CH_3$; $R^{e4}$ is H, F or Br; $R^{e5}$ is Cl, $CH_3$, $CF_3$, $OCF_3$ or $CH_2CH_3$; $R^{e6}$ is H, $CH_3$, $CH_2CHF_2$ or C≡CH; $R^{e1}$ is OH, —OC(═O)Et, —OC(═O)-i-Pr or —OC(═O)-t-Bu; and $A^{e8}$ is N or CH.

Cellulose biosynthesis inhibitors (b14) inhibit the biosynthesis of cellulose in certain plants. They are most effective when using a pre-application or early post-application on young or rapidly growing plants. Examples of cellulose biosynthesis inhibitors include chlorthiamid, dichlobenil, flupoxam, indaziflam ($N^2$-[(1R,2S)-2,3-dihydro-2,6-dimethyl-1H-inden-1-yl]-6-(1-fluoroethyl)-1,3,5-triazine-2,4-diamine), isoxaben and triaziflam.

Other herbicides (b15) include herbicides that act through a variety of different modes of action such as mitotic disruptors (e.g., flamprop-M-methyl and flamprop-M-isopropyl) organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, bromobutide, cinmethylin, clomazone, cumyluron, cyclopyrimorate (6-chloro-3-(2-cyclopropyl-6-methylphenoxy)-4-pyridazinyl 4-morpholinecarboxylate), daimuron, difenzoquat, etobenzanid, fluometuron, flurenol, fosamine, fosamine-ammonium, dazomet, dymron, ipfencarbazone (1-(2,4-dichlorophenyl)-N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 5-[[(2,6-difluorophenyl)methoxy]methyl]-4,5-dihydro-5-methyl-3-(3-methyl-2-thienyl)isoxazole.

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzenesulfonamide and N-(aminocarbonyl)-2-fluorobenzenesulfonamide, 1-bromo-4-[(chloromethyl)sulfonyl]benzene, 2-(dichloromethyl)-2-methyl-1,3-dioxolane (MG 191), 4-(dichloroacetyl)-1-oxa-4-azospiro[4.5]decane (MON 4660).

The compounds of Formula 1 can be prepared by general methods known in the art of synthetic organic chemistry. One or more of the following methods and variations as described in Schemes 1-14 can be used to prepare compounds of Formula 1. The definitions of $X^1$, $X^2$, $X^3$, n, $P^1$ and $P^2$ in the compounds of Formulae 1-17 below are as defined above in the Summary of the Invention unless otherwise noted. A compound of Formulae 1A, 1B, and 1C are subsets of Formula 1, and all substituents for compounds of Formulae 1A, 1B and 1C are as defined above for a compound of Formula 1 unless otherwise noted. A compound of Formulae 10A and 10B are subsets of Formula 10, and all substituents for compounds of Formulae 10A and 10B are as defined above for a compound of Formula 10 unless otherwise noted.

As shown in Scheme 1, pyrazoles of Formula 1A (a subset of compounds of Formula 1 where P is hydrogen) can be alkylated or allowed to react with a suitable electrophilic reagent in the presence of base in an appropriate solvent to afford compounds of Formulae 1B where P is other than H as defined for compounds of Formulae 1 in the Summary of the Invention. Although shown as only one tautomer where the exchangeable ring hydrogen resides on the nitrogen with no adjacent substituents, pyrazoles of Formula 1A can exist in equilibrium with a tautomeric species where the ring hydrogen resides on the pyrazole nitrogen adjacent to the aryl substituent. Compounds of Formula 1B are generally formed as the predominant product due to preferred alkylation at the less sterically hindered pyrazole ring nitrogen but some alkylation of the other pyrazole ring nitrogen adjacent to the aryl ring can take place through tautomerization to give the regioisomer pyrazole of Formula 2. However, isomeric pyrazoles of Formula 2 are generally obtained as minor products relative to pyrazoles of Formula 1B. The relative amounts of regioisomeric pyrazoles of Formulae 1B and 2 formed can vary depending on substituents present on pyrazoles of Formula 1A and the specific alkylation method used. Pyrazoles of Formula 1A can be treated initially with base to form a carbanionic species that is then allowed to react with the alkylating agent or electrophilic reagent. Alternatively, base and electrophile can be added simultaneously in some cases to compounds of Formula 1A previously dissolved in solvent. Examples of suitable bases for this reaction include but are not limited to potassium carbonate, sodium hydroxide, potassium hydroxide, sodium hydride, potassium t-butoxide and, depending on the specific base used, appropriate solvents can be protic or aprotic and used anhydrous or as an aqueous mixture. Some examples of solvents include acetonitrile, methanol, ethanol, tetrahydrofuran, diethyl ether, dioxane, dichloromethane or N,N-dimethylformamide. The reaction can be run at a range of temperatures, with temperatures typically ranging from 0° C. to the reflux temperature of the solvent.

isomerization where the exchangeable hydrogen can reside on either ring nitrogen, although this hydrogen is shown in the compounds of Formulae 1A and 4 to reside of the ring nitrogen furthest from the aryl group. The ratio of pyrazoles of Formulae 1A and 4 formed in this reaction can vary depending on substitution on the substitution on the intermediate compound of Formula 3 and the reaction conditions employed.

Scheme 2

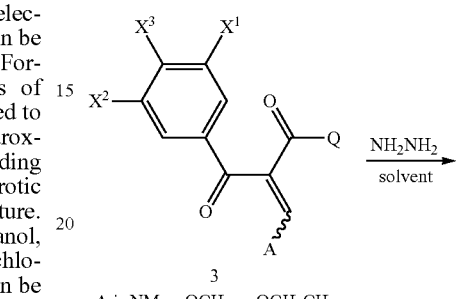

A is NMe$_2$, OCH$_3$ or OCH$_2$CH$_3$

Scheme 1

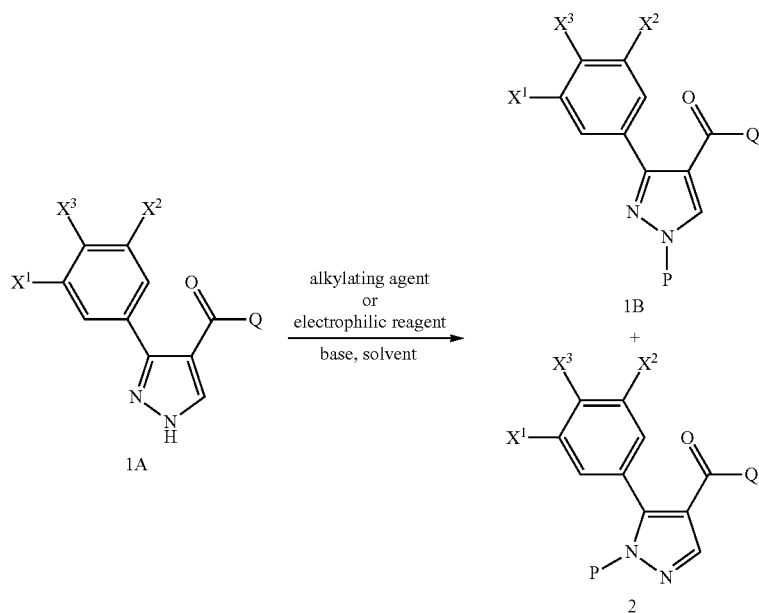

A non-regioselective method for making pyrazoles of Formula 1A is outlined in Scheme 2. By the method taught in Example 2 of U.S. Pat. No. 5,939,559, or following the method described in *J. Heterocyclic Chem.* 1982, 19, 1355, hydrazine (anhydrous or the hydrate) can be cyclized with substituted 2-methylene-1,3-pentanediones of Formulae 3 (where A serves as a leaving group such as dimethylamino, ethoxy or methoxy) in a protic or aprotic solvent such as acetonitrile, methanol, ethanol or N,N-dimethylformamide to afford regioisomeric pyrazole mixtures of 1A and 4 that are separated via chromatography and/or fractional crystallization. Temperatures for this reaction typically range from 0° C. to the reflux temperature of the solvent. Pyrazoles of Formulae 1A and 4 can exist as tautomeric species via -continued

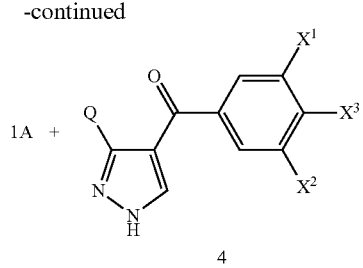

Substituted 2-methylene-1,3-pentanediones of Formula 3, where A is a leaving group such dimethylamino, ethoxy or methoxy, can be made by reacting substituted diaryl-1,3-pentanediones of Formula 5 with N,N-dimethylformamide dimethylacetal or a trialkyl orthoformate such as HC(OMe)$_3$ or HC(OEt)$_3$ neat or in a suitable solvent such as acetonitrile, methanol, ethanol, tetrahydrofuran, dioxane, toluene, dichloromethane or N,N-dimethylformamide. Temperatures for this reaction generally range from 25° C. to the reflux temperature of the neat mixture or solvent.

Scheme 3

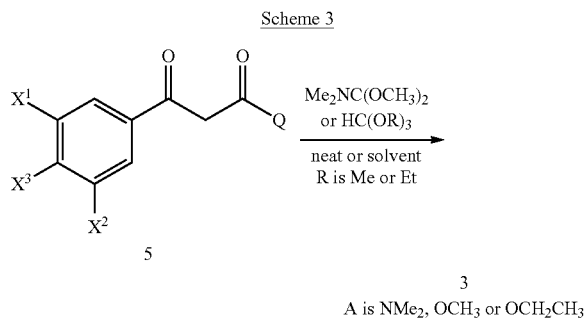

A is NMe$_2$, OCH$_3$ or OCH$_2$CH$_3$

Methods to make substituted 1,3-diaryl-1,3-pentanediones of Formula 5 are well established with many procedures documented in the literature. For example, see *Synth. Comm.* 2007, 37(23), 4111-4115, *Org. Lett.* 2005, 7(3), 455-458, U.S. 20130137688, *Tetrahedron Lett.* 2003, 44(5) 1067-1069 and *Med. Chem. Res.* 2012, 21(5), 584-589. A particularly useful method for making diones of Formula 5 involves base-catalyzed coupling of an appropriately substituted acetophenone with a substituted benzoate by the procedure described in Example 1 of U.S. Pat. No. 5,939,559. As outlined in Scheme 4, benzoates of Formula 6 (generally where R is ethyl or methyl) are allowed to react with a fluoroacetophenone of Formula 7 in the presence of a suitable base, i.e. sodium hydride, a sodium alkoxide or potassium t-butoxide in a solvent such as tetrahydrofuran, dioxane, N,N-dimethylformamide or a protic alcohol solvent such as methanol or ethanol at temperatures ranging from 0° C. to the reflux temperature of the solvent. Alternatively, substituted acetophenones of Formula 8 can undergo base-catalyzed coupling with a fluorobenzoate of Formula 9 under the same reaction conditions to provide diones of Formula 5.

A regioselective route for making pyrazoles of Formula 1A entails a Grignard catalyzed coupling of an unprotected 3-phenyl-4-iodopyrazole of Formula 10A with an aldehyde of Formula 11. As shown in Scheme 5, this reaction can be performed in a suitable solvent such as tetrahydrofuran, dioxane or diethyl ether at temperatures ranging from 0° C. to the reflux temperature of the solvent. A preferred Grignard reagent used to generate the pyrazole Grignard compound of Formula 10A for coupling with an appropriate benzaldehyde is isopropylmagnesium bromide where over 2 equivalents are added to the compound of Formula 10A due to the exchangeable pyrazole ring proton present on the compound of Formula 10A. The formed alcohol adduct is oxidized directly with an appropriate oxidizing reagent such as Jones Reagent, magnesium dioxide or pyridinium chlorochromate, TEMPO or Fehling's solution, to afford pyrazole ketones of Formula 1A. The Grignard coupling described in Scheme 5 also works for 3-phenyl-4-bromopyrazoles but 3-phenyl-4-iodopyrazoles are generally preferred.

Scheme 5

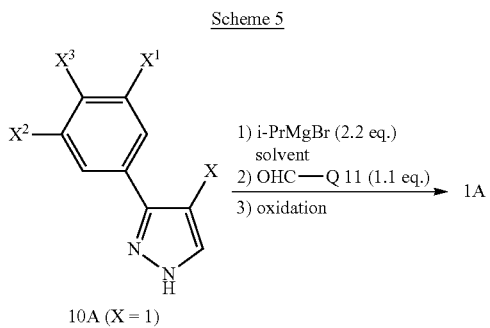

As shown in Scheme 6, iodopyrazoles of Formula 10A are readily made by iodination of pyrazoles of Formula 12 in the presence of an iodinating reagent such as N-iodosuccinimide or ICl in a solvent such as acetonitrile, tetrahydrofuran, dioxane or N,N-dimethylformamide and at temperatures ranging from 0° C. to the reflux temperature of the solvent. Bromination of pyrazoles of Formula 12 with a brominating agent such as bromine or N-bromosuccinimide gives the corresponding 3-phenyl-4-bromopyrazols of Formula 10B.

Scheme 4

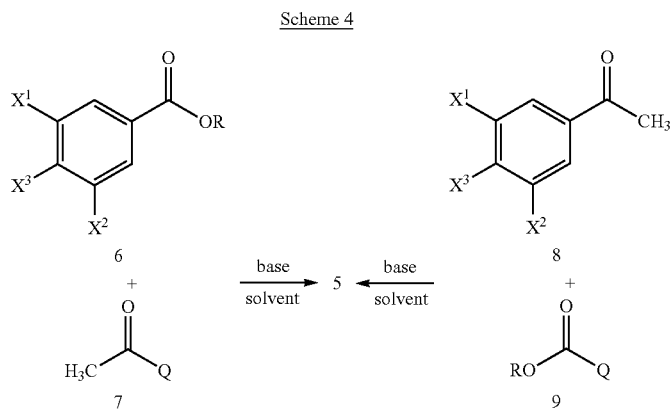

R is Me or Et

Scheme 6

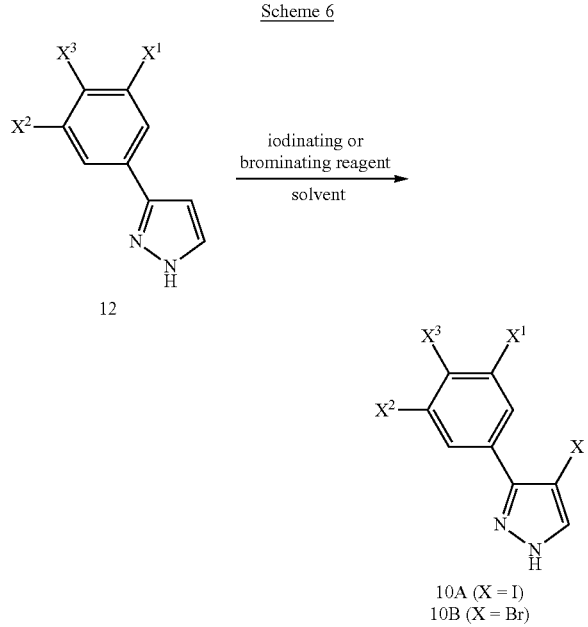

10A (X = I)
10B (X = Br)

Substituted 3-phenylpyrazoles of Formula 12 are readily made by the route outlined in Scheme 7. Stirring substituted acetophenones of Formula 8 with N,N-dimethylformamide dimethylacetal or a trialkyl orthoformate such as HC(OMe)$_3$ or HC(OEt)$_3$ neat or in a solvent such as acetonitrile, methanol, ethanol, tetrahydrofuran, dioxane, toluene, dichloromethane or N,N-dimethylformamide, at a temperature ranging from 25° C. to the reflux temperature of the neat mixture or solvent, gives enone intermediates of Formula 13 (where A is a leaving group that is generally dimethylamino, ethoxy or methoxy). Cyclization of a compound of Formula 13 with hydrazine (anhydrous or the hydrate) in a protic or aprotic solvent, i.e. acetonitrile, methanol, ethanol or N,N-dimethylformamide gives phenylpyrazoles of Formula 12. Temperatures for this reaction can range from 0° C. to the reflux temperature of the solvent. The chemistry methods described in Schemes 6 and 7 have literature precedence as illustrated in WO2013/062887 and *Tetrahedron* 2003, 59(4), 555-560.

Scheme 7

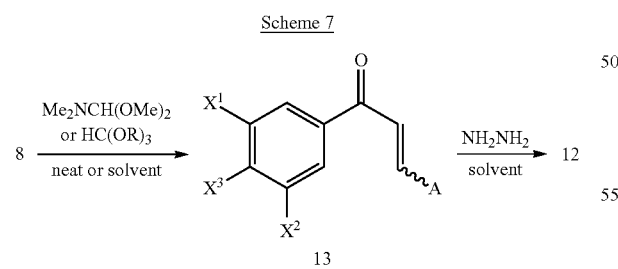

The ring nitrogen on 3-phenyl-4-iodopyrazoles of Formula 10A can also be protected with an appropriate capping group (e.g., N,N-dimethylsulfonyl (—SO$_2$N(CH$_3$)$_2$), methoxymethyl (—CH$_2$OCH$_3$) or benzyl carbamate (cbz)) before generating the Grignard for addition to benzaldehydes of Formula 11 as shown in Scheme 8. For example, reaction of a compound of Formula 10A with N,N-dimethyl chlorosulfonylamine or bromomethylether in the presence of base (i.e. potassium carbonate or sodium hydride) in a solvent (tetrahydrofuran, dioxane, acetonitrile, toluene or N,N-dimethylformamide) affords N-protected pyrazoles 14 where P is SO$_2$N(CH$_3$) or CH$_2$OCH$_3$. Coupling of a compound of Formula 14 with isopropylmagnesium bromide gives the pyrazole Grignard that on reaction with benzaldehydes of Formula 11 in solvent, i.e. tetrahydrofuran, dioxane or diethyl ether, at temperatures ranging from 0° C. to the reflux temperature of the solvent gives alcohol intermediates that are oxidized to pyrazole ketones 1C (i.e. a subset of Formula 1 where P is SO$_2$N(CH$_3$) or CH$_2$OCH$_3$). The oxidation of alcohol to ketone is usually accomplished with Jones Reagent but other oxidants can be used. A preferred Grignard reagent for generating the N-protected pyrazole Grignard is isopropylmagnesium bromide where 1.1 to 1.2 equivalents are generally used. The N-protected 3-phenylpyrazole phenyl ketones of Formula 1C are sometimes the intended synthetic target as a further subset of 1B but can also be converted to pyrazoles of Formula 1A by removal of the N-protecting group with an appropriate reagent such as an acid. Trifluoroacetic acid works well for de-protection when PG is SO$_2$N(CH$_3$)$_2$.

Scheme 8

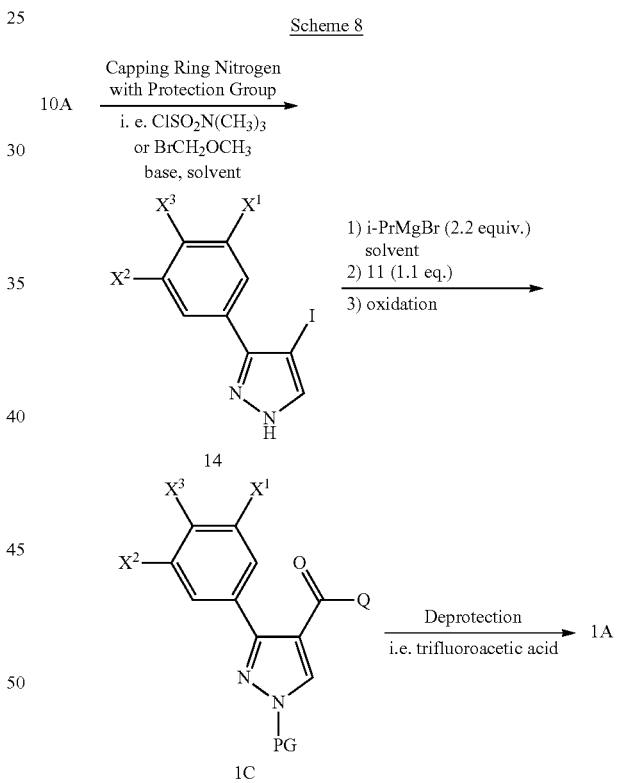

An alternative regioselective method for making 3-phenyl-4-flurobenzoyl pyrazoles of Formula 1A is summarized in Scheme 9. Nitrogen-protected 3-bromo-4-fluorobenzoyl pyrazoles of Formula 15 can be cross-coupled with aryl boronic acids of Formula 16 in the presence of a palladium catalyst such as tetrakis(triphenylphosphine)palladium or dichloro-bis-(triphenylphosphine)palladium, optionally with a base such as a metal carbonate or tertiary amine, in solvents such as dioxane, N,N-dimethylformamide, tetrahydrofuran or toluene at temperatures normally ranging from 25° C. to the reflux temperature of the solvent to give N-protected 3-phenyl-4-fluorobenzoyl pyrazoles of Formula 1C that on de-protection provides compounds of Formula 1A. Protecting groups PG and de-protection conditions are the same as that described for Scheme 8.

Scheme 9

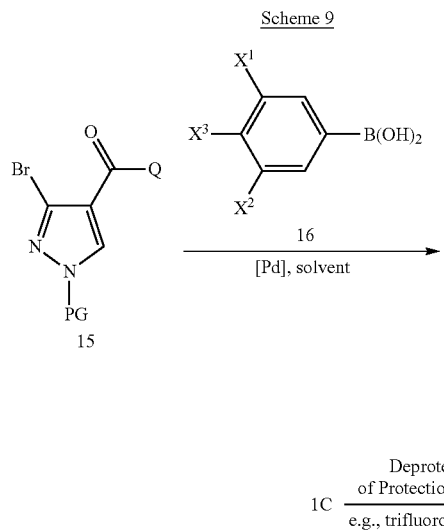

Scheme 10

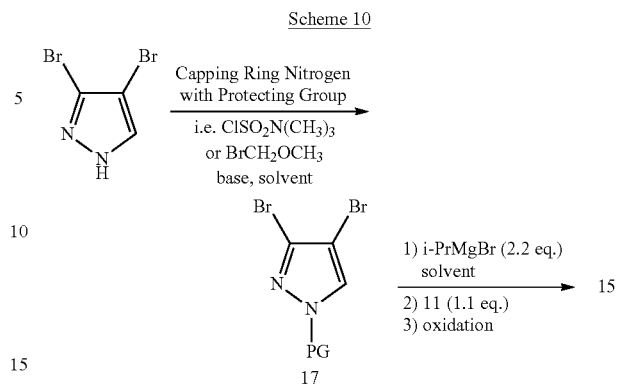

Oximes of Formula 1c where P is defined as for 1 can be made by treating ketones of Formula 1a (which have a free pyrazole NH) or ketones of Formula 1b (where P is other than H) with hydroxylamine or an alkoxylamine of Formula $NH_2OR$, as the free base or salt form, generally in the presence of base but sometimes in the presence of acid catalyst in a protic or aprotic solvent. Some examples of preferred solvents include methanol, ethanol, pyridine, water, dioxane and acetonitrile or N,N-dimethylformamide. Examples of bases include but are not limited to sodium acetate, sodium methoxide and potassium hydroxide. The reaction can be run under a range of temperatures, with temperatures typically ranging from 25° C. to the reflux temperature of the solvent. Use of pyridine as both solvent and base for this reaction is sometimes preferred.

Scheme 11

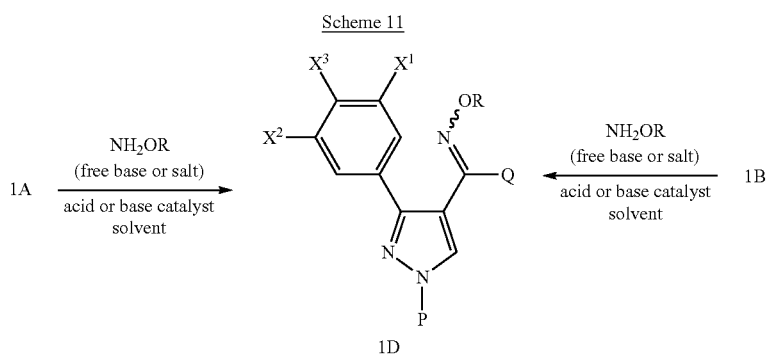

Scheme 10 outlines the preparation of N-protected 3-bromopyrazole ketone intermediates of Formula 15 where a protecting group is first placed on the ring nitrogen of 3,4-dibromopyrazole to give N-protected-3,4-dibromopyrazoles 17. Suitable protecting groups (PG) and reaction conditions are the same as that described in Scheme 8. Conditions for selective Grignard formation at the 4-pyrazole position, addition to benzaldehydes of Formula 11 to give alcohols that are oxidized to pyrazole ketones of Formula 16 is also the same as that in Scheme 8. Grignard formation at the 3-pyrazole position is generally not competitive with Grignard formation at the 4-position which allows for limited side product formation. For literature methods to make N,N-dimethylsulfonyl pyrazoles of Formula 17 where PG is $SO_2N(CH_3)_2$, see WO2011/102399, WO2007/014290 and Synthesis 2006, (5), 793-798.

Under the same conditions outlined in Scheme 11, hydrazones of Formula 1E (where P is the same that defined for 1) can be made by treating ketones of Formula 1A (with a free pyrazole NH) or ketones of Formula 1b (where P is other than H) with hydrazines of Formula $NH_2NR^1R^2$ (as a free base or in the salt form) as shown in Scheme 12. The hydrazines of Formula $NH_2NR^1R^2$ are generally used in the free base form and common solvents for this reaction include methanol, ethanol and acetonitrile. Although geometric isomers are possible, only one isomer is generally obtained as the major product from this condensations outlined in Schemes 11 and 12.

Scheme 12

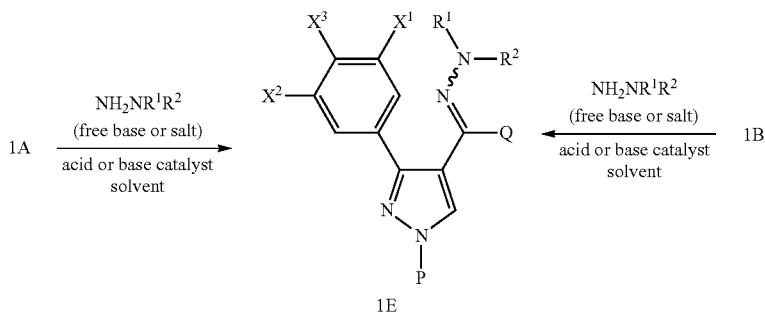

As illustrated in Scheme 13, ketals of Formula 1F (where P is the same as that defined for 1) can be made by reacting ketones of Formula 1A (which have a free pyrazole NH) or ketones of Formula 1B (where P is other than H) with an excess of alcohol of Formula $R^3WH$ (where W is O or S), usually in the presence of an acidic catalyst such as p-toluenesulfonic acid or concentrated sulfuric acid in solvents such as methanol or ethanol or in an aprotic solvent such as toluene. Conditions for preparing a compound of Formula 1F where W is O using a trialkylorthoformate in an alkanol can be found in *Synth. Comm.* 2008, 38, 2607.

Scheme 13

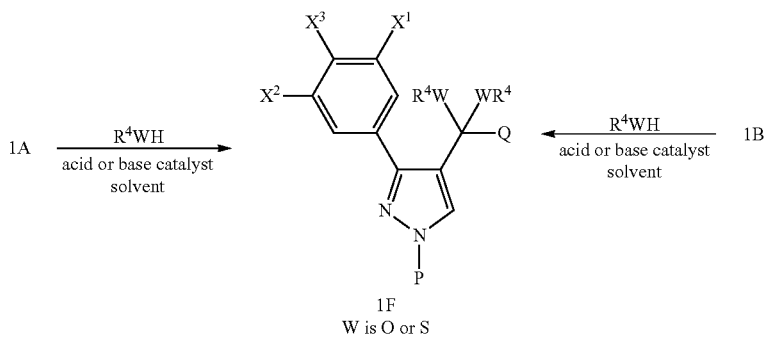

As illustrated in Scheme 14, imines, alkylamines and cyanoimines of Formula 1G can be prepared in the same method as that described in Schemes 11 through 13. A compound of Form of Formula 1F (where P is the same as that defined for a compound of Formula 1) can be made by reacting ketones of Formula 1A (which have a free pyrazole NH) or ketones of Formula 1B (where P is other than H) with an excess of Formula $NH_2R^1$ (where $R^1$ is as defined in the Summary of the Invention), usually in the presence of an acidic catalyst, i.e. p-toluenesulfonic acid or concentrated sulfuric acid in methanol or ethanol or in a aprotic solvent such as toluene.

Scheme 14

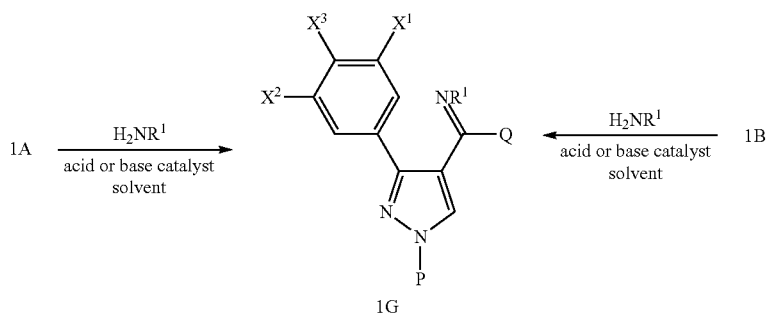

It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations*, 2nd Ed., Wiley-VCH, New York, 1999. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1. The above reactions can also in many cases be performed in alternate order It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. In the following examples the abbreviation "eq" means equivalent, and parts and percentages for chromatographic solvent mixtures are by volume unless otherwise indicated. $^1$H NMR spectra are reported in ppm in $CDCl_3$ at 500 MHz downfield from tetramethylsilane; "s" means singlet, "d" means doublet, "t" means triplet, "m" means multiplet and "bs" means broad singlet.

Synthesis Example 1

Preparation of N-[[3-(3,5-dichlorophenyl)-1H-pyrazol-4-yl]phenylmethylene]-1-pyrrolidinamine (Compound 30)

Step A: Preparation of 1-(3,5-dichlorophenyl)-3-(dimethylamino)-2-propen-1-one

3',5'-Dichloroacetophenone (9.7 g, 51 mmol) was heated at reflux in N,N-dimethylformamide dimethylacetal (50 mL) for 3 h. After cooling to ambient temperature, the reaction mixture was concentrated and dried under vacuum to give of an orange solid (12.3 g) that was used without further purification.

$^1$H NMR δ 7.82 (d, 1H), 7.74 (s, 2H), 7.42 (s, 1H), 5.58 (d, 1H), 3.18 (bs, 3H), 2.95 (bs, 3H).

Step B: Preparation of 3-(3,5-dichlorophenyl)-1H-pyrazole

To 1-(3,5-dichlorophenyl)-3-(dimethylamino)-2-propen-1-one (i.e. the product obtained in Step A) (12.3 g, 50.4 mmol) in ethanol (100 mL) was added hydrazine hydrate (5.7 mL, 55% by weight in water, 100 mmol). The reaction mixture was stirred at ambient temperature for 18 h. The reaction mixture was concentrated and dried under vacuum to give a beige solid (10.9 g) that was used without further purification.

$^1$H NMR δ 11.2 (bs, 1H), 7.67 (s, 2H), 7.62 (m, 1H), 7.31 (m, 1H), 6.62 (m, 1H).

Step C: Preparation of 3-(3,5-dichlorophenyl)-4-iodo-1H-pyrazole

N-Iodosuccinimide (13.7 g, 61 mmol) was added to a mixture of 3-(3,5-dichlorophenyl)-1H-pyrazole (i.e. the product obtained in Step B) (10.9 g, 51 mmol) in acetonitrile (100 mL) at ambient temperature. After stirring for 24 h, water was added, and the product was extracted with ethyl acetate. The organic extract was washed with brine, dried with $Mg(SO_4)_2$, filtered and concentrated. The concentrated solid was triturated with hot hexanes and filtered to provide a beige solid (9.8 g).

$^1$H NMR δ 7.70 (m, 3H), 7.39 (m, 1H).

Step D Preparation of 3-(3,5-dichlorophenyl)-α-phenyl-1H-pyrazole-4-methanol

Isopropylmagnesium bromide (4.0 mL, 2.9 M in 2-methyltetrahydrofuran, 11.8 mmol) was added dropwise to a stirred solution of 3-(3,5-dichlorophenyl)-4-iodo-1H-pyrazole (i.e. the product obtained in Step C) (2.0 g, 5.9 mmol) in tetrahydrofuran (6 mL) at 0° C. The reaction mixture was stirred at 0° C. for 1 h. Benzaldehyde (0.66 mL, 6.5 mmol) was added, and the reaction mixture was stirred for 3 d at ambient temperature. After cooling to 0° C., the reaction mixture was quenched with aqueous saturated ammonium chloride, and extracted with ethyl acetate. The organic extract was dried with $Mg(SO_4)_2$, filtered, concentrated onto Celite® diatomaceous earth filter aid and purified by MPLC, eluting with a 0-100% gradient of ethyl acetate in hexanes to give of a clear, colorless oil (1.35 g).

$^1$H NMR δ 7.60 (m, 2H), 7.35 (m, 4H), 7.30 (m, 3H), 5.90 (s, 1H).

Step E: Preparation of [3-(3,5-dichlorophenyl)-1H-pyrazol-4-yl]phenylmethanone

To a solution of 3-(3,5-dichlorophenyl)-α-phenyl-1H-pyrazole-4-methanol (i.e. the product obtained in Step D) (1.35 g, 4.2 mmol) in acetone (25.0 mL) at 0° C. was added Jones Reagent (1.4 mL, 2.7 M $CrO_3/H_2SO_4$ in $H_2O$)). The solution was stirred cold for 3 h. Saturated aqueous sodium bicarbonate was added, and the mixture was extracted with dichloromethane. The organic extract was dried $Mg(SO_4)_2$, filtered, and concentrated to give 1.21 g of a light beige solid.

¹H NMR δ 11.0 (bs, 1H), 7.95 (s, 1H), 7.80 (d, 2H), 7.57 (m, 3H), 7.45 (m, 2H), 7.33 (m, 1H).

Step F: N-[[3-(3,5-dichlorophenyl)-1H-pyrazol-4-yl] phenylmethylene]-1-pyrrolidinamine To [3-(3,5-dichlorophenyl)-1H-pyrazol-4-yl]phenylmethanone (i.e. the product obtained in Step E) (0.5 g, 1.6 mmol) in pyridine (10 mL) was added 1-aminopyrrolidine hydrochloride (1.9 g, 16 mmol). The reaction mixture was heated at 100° C. for 24 h. After cooling to ambient temperature, 1 N hydrochloric acid was added, and the reaction mixture was extracted with ethyl acetate. The extract was washed once with 1 N hydrochloric acid, once with water and once with brine. The extract was then dried with $Mg(SO_4)_2$, filtered, and concentrated. The concentrate was purified by MPLC, eluting with a 0-100% gradient of ethyl acetate in hexanes to give of a tan solid (0.4 g) with a melting point of 142-149° C.
¹H NMR δ 7.66 (s, 1H), 7.56 (s, 2H), 7.46 (m, 2H), 7.21 (m, 4H), 3.07 (m, 4H), 1.71 (m, 4H).

Synthesis Example 2

Preparation of [3-(3,5-dichlorophenyl)-1-(2-propyn-1-yl)-1H-pyrazol-4-yl]phenylmethanone (Compound 39)

Step A: Preparation of [3-(3,5-dichlorophenyl)-1-(2-propyn-1-yl)-1H-pyrazol-4-yl]phenylmethanone To [3-(3,5-dichlorophenyl)-1H-pyrazol-4-yl]phenylmethanone (i.e. the product obtained in Example 1, Step E) (0.2 g, 0.63 mmol) in acetonitrile (7 mL) was added propargyl bromide (0.11 mL, 80% solution in toluene, 0.95 mmol) and potassium carbonate (0.18 g, 1.3 mmol) at ambient temperature. The reaction mixture was stirred for 2 h. Ethyl acetate was added to the reaction mixture and the organic layer was separated, washed twice with water and once with brine. The organic layer was then dried with $Mg(SO_4)_2$, filtered, and concentrated to give 0.20 g of a clear pale yellow oil.
¹H NMR δ 8.02 (s, 1H), 7.79 (m, 2H), 7.60 (s, 2H), 7.54 (t, 1H), 7.43 (m, 2H), 7.30 (s, 1H), 5.02 (d, 2H), 2.60 (t, 1H).

Synthesis Example 3

Preparation of [3-(3,5-dichlorophenyl)-1-(hydroxymethyl)-1H-pyrazol-4-yl]phenylmethanone (Compound 15)

Step A: Preparation of [3-(3,5-dichlorophenyl)-1-(hydroxymethyl)-1H-pyrazol-4-yl]phenylmethanone To [3-(3,5-dichlorophenyl)-1H-pyrazol-4-yl]phenylmethanone (i.e. the product obtained in Example 1, Step E) (2.0 g, 6.3 mmol) in water (20 mL) was added formaldehyde (2.5 mL, 37% solution in water, 32 mmol) at ambient temperature. The homogenous solution was stirred at ambient temperature for 24 h. The reaction mixture was concentrated and azeotroped twice with toluene. The concentrate was purified by MPLC, eluting with a 0-100% gradient of ethyl acetate in hexanes to give a white solid (1.9 g).
¹H NMR δ 7.95 (s, 1H), 7.77 (m, 2H), 7.56 (s, 3H), 7.44 (m, 2H), 7.31 (m, 1H), 5.58 (m, 2H), 4.85 (bs, 1H).

Synthesis Example 4

Preparation of 1-[4-benzoyl-3-(3,5-dichlorophenyl)-1H-pyrazol-1-yl]-2-methoxyethanone Compound 16

Step A: Preparation of 1-[4-benzoyl-3-(3,5-dichlorophenyl)-1H-pyrazol-1-yl]-2-methoxyethanone To [3-(3,5-dichlorophenyl)-1H-pyrazol-4-yl]phenylmethanone (i.e. the product obtained in Example 1, Step E) (1.0 g, 3.2 mmol) and methoxyacetyl chloride (0.6 mL, 6.4 mmol) in tetrahydrofuran (20 mL) at 0° C. was added pyridine (0.51 mL, 6.4 mmol). The white reaction mixture was stirred cold for 4 h. Aqueous saturated ammonium chloride was added, and the product was extracted with ethyl acetate. The extract was dried with $Mg(SO_4)_2$, filtered, concentrated, and purified by MPLC, eluting with a 0-100% gradient of ethyl acetate in hexanes to give a white solid (1.03 g) with a melting point of 118-123° C.
¹H NMR δ 8.57 (s, 1H), 7.84 (d, 2H), 7.65 (m, 3H), 7.50 (t, 2H), 7.41 (s, 1H), 4.99 (s, 2H), 3.61 (s, 3H).

Synthesis Example 5

Preparation of [3-(3,5-dichlorophenyl)-1-ethyl-1H-pyrazol-4-yl]phenylmethanone (Compound 31)

Step A: Preparation of [3-(3,5-dichlorophenyl)-1-ethyl-1H-pyrazol-4-yl]phenylmethanone To [3-(3,5-dichlorophenyl)-1H-pyrazol-4-yl]phenylmethanone (i.e. the product obtained in Example 1, Step E) (0.3 g, 0.95 mmol) in acetonitrile (15 mL) was added iodoethane (0.1 mL, 1.23 mmol) and potassium carbonate (0.197 g, 1.42 mmol) at ambient temperature. The reaction mixture was stirred for 2 h. An additional 1 eq. iodoethane and 1 eq. potassium carbonate were added. The reaction mixture was stirred an additional 3 h. Dilution of the reaction mixture with water was followed by extraction with ethyl acetate. The ethyl acetate phase was washed once with brine, dried with $Mg(SO_4)_2$, filtered, and concentrated by rotary evaporation. Column chromatography on silica gel eluting with 100% hexanes followed by 100% dichloromethane to yield a clear oil (0.22 g).
¹H NMR δ 7.69-7.89 (m, 3H), 7.63 (m, 2H), 7.47-7.56 (m, 1H), 7.35-7.45 (m, 2H), 7.28 (m, 1H), 4.22 (m, 2H), 1.55 (m, 3H).

Synthesis Example 6

Preparation of [3-(3,5-dichlorophenyl)-1-methyl-1H-pyrazol-4-yl]phenylmethanone (Compound 54)

Step A: [3-(3,5-dichlorophenyl)-1-methyl-1H-pyrazol-4-yl]phenylmethanone

To [3-(3,5-dichlorophenyl)-1H-pyrazol-4-yl]phenylmethanone (i.e. the product obtained in Example 1, Step E) (0.1 g, 0.32 mmol) in acetonitrile (5 mL) was added iodomethane (0.026 mL, 0.41 mmol) and potassium carbonate (0.066 g, 0.47 mmol) at ambient temperature. The reaction mixture was stirred for 2 h. Dilution of the reaction mixture with water was followed by extraction with ethyl acetate. The ethyl acetate phase was washed once with brine, dried with $Mg(SO_4)_2$, filtered, and concentrated by rotary evaporation. Column chromatography on silica gel eluting with 0-20% ethyl acetate in hexanes yielded 0.071 g of clear oil.

$^1$H NMR δ 7.69-7.80 (m, 3H), 7.62 (m, 2H), 7.53 (m, 1H), 7.42 (m, 2H), 7.29 (m, 1H), 3.97 (s, 3H).

Synthesis Example 7

Preparation of [3-(3,5-dichlorophenyl)-1-propyl-1H-pyrazol-4-yl]phenylmethanone (Compound 61)

Step A: Preparation of [3-(3,5-dichlorophenyl)-1-propyl-1H-pyrazol-4-yl]phenylmethanone To [3-(3,5-dichlorophenyl)-1H-pyrazol-4-yl]phenylmethanone (i.e. the product obtained in Example 1, Step E) (0.18 g, 0.57 mmol) in acetonitrile (5 mL) was added 1-bromopropane (0.083 mL, 0.85 mmol) and potassium carbonate (0.118 g, 0.85 mmol) at ambient temperature. The reaction mixture was stirred for 2 h. Dilution of the reaction mixture with water was followed by extraction with ethyl acetate. The ethyl acetate phase was washed once with brine, dried with Mg(SO$_4$)$_2$, filtered, and concentrated by rotary evaporation. Column chromatography on silica gel eluting with 0-0% ethyl acetate in hexanes to yield a clear oil (0.16 g).

$^1$H NMR δ 7.70-7.83 (m, 3H), 7.64 (m, 2H), 7.48-7.55 (m, 1H), 7.34-7.44 (m, 2H), 7.28 (m, 1H), 4.12 (m, 2H), 1.83-2.01 (m, 2H), 0.96 (m, 3H).

By the procedures described herein together with methods known in the art, the following compounds of Tables 1 to 204 can be prepared. The following abbreviations are used in the Tables which follow: Ac means acetate (i.e. —C(=O)CH$_3$), i means iso, c means cyclo, Et means ethyl, Pr means propyl, i-Pr means isopropyl, c-Pr cyclopropyl, Ph means phenyl, Thn means thienyl, OEt means ethoxy, NHMe methylamino, —CN means cyano and Py means pyridinyl.

TABLE 1

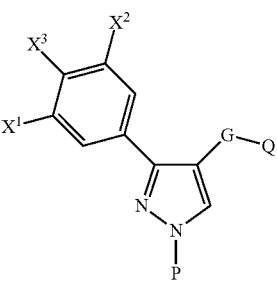

| X$^1$ | X$^2$ | X$^3$ |
|---|---|---|
| F | F | H |
| F | Cl | H |
| F | Br | H |
| F | I | H |
| F | CF$_3$ | H |
| F | CF$_2$H | H |
| F | OCF$_3$ | H |
| F | OCF$_2$H | H |
| F | SCF$_2$H | H |
| F | C≡CH | H |
| Cl | Cl | H |
| Cl | Br | H |
| Cl | I | H |
| Cl | CF$_3$ | H |
| Cl | CF$_2$H | H |

TABLE 1-continued

| X$^1$ | X$^2$ | X$^3$ |
|---|---|---|
| Cl | OCF$_3$ | H |
| Cl | OCF$_2$H | H |
| Cl | SCF$_2$H | H |
| Cl | C≡CH | H |
| Br | Br | H |
| Br | I | H |
| Br | CF$_3$ | H |
| Br | CF$_2$H | H |
| Br | OCF$_3$ | H |
| Br | OCF$_2$H | H |
| Br | SCF$_2$H | H |
| Br | C≡CH | H |
| I | I | H |
| I | CF$_3$ | H |
| I | CF$_2$H | H |
| I | OCF$_3$ | H |
| I | OCF$_2$H | H |
| I | SCF$_2$H | H |
| I | C≡CH | H |
| CF$_3$ | CF$_3$ | H |
| CF$_3$ | CF$_2$H | H |
| CF$_3$ | OCF$_3$ | H |
| CF$_3$ | OCF$_2$H | H |
| CF$_3$ | SCF$_2$H | H |
| CF$_3$ | C≡CH | H |
| CF$_2$H | CF$_2$H | H |
| CF$_2$H | OCF$_3$ | H |
| CF$_2$H | OCF$_2$H | H |
| CF$_2$H | SCF$_2$H | H |
| CF$_2$H | C≡CH | H |
| OCF$_3$ | OCF$_3$ | H |
| OCF$_3$ | OCF$_2$H | H |
| OCF$_3$ | SCF$_2$H | H |
| OCF$_3$ | C≡CH | H |
| OCF$_2$H | OCF$_2$H | H |
| OCF$_2$H | SCF$_2$H | H |
| OCF$_2$H | C≡CH | H |
| SCF$_2$H | SCF$_2$H | H |
| SCF$_2$H | C≡CH | H |
| C≡CH | C≡CH | H |
| F | F | F |
| F | Cl | F |
| F | Br | F |
| F | I | F |
| F | CF$_3$ | F |
| F | CF$_2$H | F |
| F | OCF$_3$ | F |
| F | OCF$_2$H | F |
| F | SCF$_2$H | F |
| F | C≡CH | F |
| Cl | Cl | F |
| Cl | Br | F |
| Cl | I | F |
| Cl | CF$_3$ | F |
| Cl | CF$_2$H | F |
| Cl | OCF$_3$ | F |
| Cl | OCF$_2$H | F |
| Cl | SCF$_2$H | F |
| Cl | C≡CH | F |
| Br | Br | F |
| Br | I | F |
| Br | CF$_3$ | F |
| Br | CF$_2$H | F |

TABLE 1-continued

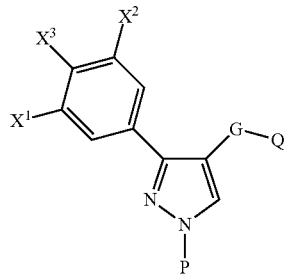

| X¹ | X² | X³ |
|---|---|---|
| Br | OCF₃ | F |
| Br | OCF₂H | F |
| Br | SCF₂H | F |
| Br | C≡CH | F |
| I | I | F |
| I | CF₃ | F |
| I | CF₂H | F |
| I | OCF₃ | F |
| I | OCF₂H | F |
| I | SCF₂H | F |
| I | C≡CH | F |
| CF₃ | CF₃ | F |
| CF₃ | CF₂H | F |
| CF₃ | OCF₃ | F |
| CF₃ | OCF₂H | F |
| CF₃ | SCF₂H | F |
| CF₃ | C≡CH | F |
| CF₂H | CF₂H | F |
| CF₂H | OCF₃ | F |
| CF₂H | OCF₂H | F |
| CF₂H | SCF₂H | F |
| CF₂H | C≡CH | F |
| OCF₃ | OCF₃ | F |
| OCF₃ | OCF₂H | F |
| OCF₃ | SCF₂H | F |
| OCF₃ | C≡CH | F |
| OCF₂H | OCF₂H | F |
| OCF₂H | SCF₂H | F |
| OCF₂H | C≡CH | F |
| SCF₂H | SCF₂H | F |
| SCF₂H | C≡CH | F |
| C≡CH | C≡CH | F |
| F | Cl | Cl |
| F | Br | Cl |
| F | I | Cl |
| F | CF₃ | Cl |
| F | CF₂H | Cl |
| F | OCF₃ | Cl |
| F | OCF₂H | Cl |
| F | SCF₂H | Cl |
| F | C≡CH | Cl |
| Cl | Cl | Cl |
| Cl | Br | Cl |
| Cl | I | Cl |
| Cl | CF₃ | Cl |
| Cl | CF₂H | Cl |
| Cl | OCF₃ | Cl |
| Cl | OCF₂H | Cl |
| Cl | SCF₂H | Cl |
| Cl | C≡CH | Cl |
| Br | Br | Cl |
| Br | I | Cl |
| Br | CF₃ | Cl |
| Br | CF₂H | Cl |
| Br | OCF₃ | Cl |
| Br | OCF₂H | Cl |
| Br | SCF₂H | Cl |
| Br | C≡CH | Cl |
| I | I | Cl |
| I | CF₃ | Cl |
| I | CF₂H | Cl |
| I | OCF₃ | Cl |
| I | OCF₂H | Cl |

TABLE 1-continued

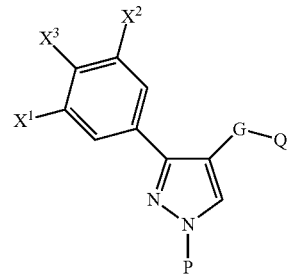

| X¹ | X² | X³ |
|---|---|---|
| I | SCF₂H | Cl |
| I | C≡CH | Cl |
| CF₃ | CF₃ | Cl |
| CF₃ | CF₂H | Cl |
| CF₃ | OCF₃ | Cl |
| CF₃ | OCF₂H | Cl |
| CF₃ | SCF₂H | Cl |
| CF₃ | C≡CH | Cl |
| CF₂H | CF₂H | Cl |
| CF₂H | OCF₃ | Cl |
| CF₂H | OCF₂H | Cl |
| CF₂H | SCF₂H | Cl |
| CF₂H | C≡CH | Cl |
| OCF₃ | OCF₃ | Cl |
| OCF₃ | OCF₂H | Cl |
| OCF₃ | SCF₂H | Cl |
| OCF₃ | C≡CH | Cl |
| OCF₂H | OCF₂H | Cl |
| OCF₂H | SCF₂H | Cl |
| OCF₂H | C≡CH | Cl |
| SCF₂H | SCF₂H | Cl |
| SCF₂H | C≡CH | Cl |
| C≡CH | C≡CH | Cl |
| F | Cl | Br |
| F | Br | Br |
| F | I | Br |
| F | CF₃ | Br |
| F | CF₂H | Br |
| F | OCF₃ | Br |
| F | OCF₂H | Br |
| F | SCF₂H | Br |
| F | C≡CH | Br |
| Cl | Cl | Br |
| Cl | Br | Br |
| Cl | I | Br |
| Cl | CF₃ | Br |
| Cl | CF₂H | Br |
| Cl | OCF₃ | Br |
| Cl | OCF₂H | Br |
| Cl | SCF₂H | Br |
| Cl | C≡CH | Br |
| Br | Br | Br |
| Br | I | Br |
| Br | CF₃ | Br |
| Br | CF₂H | Br |
| Br | OCF₃ | Br |
| Br | OCF₂H | Br |
| Br | SCF₂H | Br |
| Br | C≡CH | Br |
| I | I | Br |
| I | CF₃ | Br |
| I | CF₂H | Br |
| I | OCF₃ | Br |
| I | OCF₂H | Br |
| I | SCF₂H | Br |
| I | C≡CH | Br |
| CF₃ | CF₃ | Br |
| CF₃ | CF₂H | Br |
| CF₃ | OCF₃ | Br |
| CF₃ | OCF₂H | Br |
| CF₃ | SCF₂H | Br |
| CF₃ | C≡CH | Br |
| CF₂H | CF₂H | Br |

TABLE 1-continued

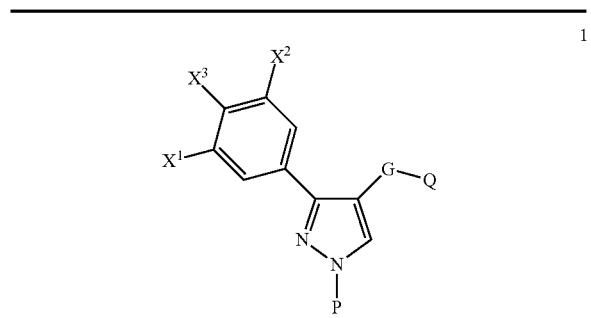

| X¹ | X² | X³ |
|---|---|---|
| CF₂H | OCF₃ | Br |
| CF₂H | OCF₂H | Br |
| CF₂H | SCF₂H | Br |
| CF₂H | C≡CH | Br |
| OCF₃ | OCF₃ | Br |
| OCF₃ | OCF₂H | Br |
| OCF₃ | SCF₂H | Br |
| OCF₃ | C≡CH | Br |
| OCF₂H | OCF₂H | Br |
| OCF₂H | SCF₂H | Br |
| OCF₂H | C≡CH | Br |
| SCF₂H | SCF₂H | Br |
| SCF₂H | C≡CH | Br |
| C≡CH | C≡CH | Br |
| F | Cl | I |
| F | Br | I |
| F | I | I |
| F | CF₃ | I |
| F | CF₂H | I |
| F | OCF₃ | I |
| F | OCF₂H | I |
| F | SCF₂H | I |
| F | C≡CH | I |
| Cl | Cl | I |
| Cl | Br | I |
| Cl | I | I |
| Cl | CF₃ | I |
| Cl | CF₂H | I |
| Cl | OCF₃ | I |
| Cl | OCF₂H | I |
| Cl | SCF₂H | I |
| Cl | C≡CH | I |
| Br | Br | I |
| Br | I | I |
| Br | CF₃ | I |
| Br | CF₂H | I |
| Br | OCF₃ | I |
| Br | OCF₂H | I |
| Br | SCF₂H | I |
| Br | C≡CH | I |
| I | I | I |
| I | CF₃ | I |
| I | CF₂H | I |
| I | OCF₃ | I |
| I | OCF₂H | I |
| I | SCF₂H | I |
| I | C≡CH | I |
| CF₃ | CF₃ | I |
| CF₃ | CF₂H | I |
| CF₃ | OCF₃ | I |
| CF₃ | OCF₂H | I |
| CF₃ | SCF₂H | I |
| CF₃ | C≡CH | I |
| CF₂H | CF₂H | I |
| CF₂H | OCF₃ | I |
| CF₂H | OCF₂H | I |
| CF₂H | SCF₂H | I |
| CF₂H | C≡CH | I |
| OCF₃ | OCF₃ | I |
| OCF₃ | OCF₂H | I |
| OCF₃ | SCF₂H | I |
| OCF₃ | C≡CH | I |
| OCF₂H | OCF₂H | I |

TABLE 1-continued

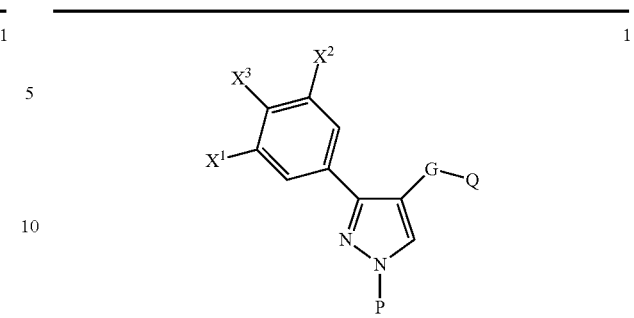

| X¹ | X² | X³ |
|---|---|---|
| OCF₂H | SCF₂H | I |
| OCF₂H | C≡CH | I |
| SCF₂H | SCF₂H | I |
| SCF₂H | C≡CH | I |
| C≡CH | C≡CH | I |

G = C(=O),
Q = Ph,
P = C(=O)CH₂OMe

The present disclosure also includes Tables 2 through 264, each of which is constructed the same as Table 1 above, except that the row heading in Table 1 (i.e. "G=C(=O), Q=Ph, P=C(=O)CH₂OMe") is replaced with the respective row heading shown below. For Example, in Table 2 the row heading is "G=C(=O), Q=2-Thn, P=C(=O)OCH₂OMe" and X¹, X², and X³ are as defined in Table 1 above.

| Table | Header Row |
|---|---|
| 2 | G = C(=O), Q = 2-Thn, P = C(=O)CH₂OMe |
| 3 | G = C(=O), Q = 3-Thn, P = C(=O)CH₂OMe |
| 4 | G = C(=O), Q = 3-Py, P = C(=O)CH₂OMe |
| 5 | G = C(=O), Q = 5-F-3-Py, P = C(=O)CH₂OMe |
| 6 | G = C(=O), Q = Ph, P = Me |
| 7 | G = C(=O), Q = 2-Thn, P = Me |
| 8 | G = C(=O), Q = 3-Thn, P = Me |
| 9 | G = C(=O), Q = 3-Py, P = Me |
| 10 | G = C(=O), Q = 5-F-3-Py, P = Me |
| 11 | G = C(=O), Q = Ph, P = CH₂Me |
| 12 | G = C(=O), Q = 2-Thn, P = CH₂Me |
| 13 | G = C(=O), Q = 3-Thn, P = CH₂Me |
| 14 | G = C(=O), Q = 3-Py, P = CH₂Me |
| 15 | G = C(=O), Q = 5-F-3-Py, P = CH₂Me |
| 16 | G = C(=O), Q = Ph, P = (CH₂)₂Me |
| 17 | G = C(=O), Q = 2-Thn, P = (CH₂)₂Me |
| 18 | G = C(=O), Q = 3-Thn, P = (CH₂)₂Me |
| 19 | G = C(=O), Q = 3-Py, P = (CH₂)₂Me |
| 20 | G = C(=O), Q = 5-F-3-Py, P = (CH₂)Me |
| 21 | G = C(=O), Q = Ph, P = CH₂C≡CH |
| 22 | G = C(=O), Q = 2-Thn, P = CH₂C≡CH |
| 23 | G = C(=O), Q = 3-Thn, P = CH₂C≡CH |
| 24 | G = C(=O), Q = 3-Py, P = CH₂C≡CH |
| 25 | G = C(=O), Q = 5-F-3-Py, P = CH₂C≡CH |
| 26 | G = C(=O), Q = Ph, P = C(=O)Me |
| 27 | G = C(=O), Q = 2-Thn, P = C(=O)Me |
| 28 | G = C(=O), Q = 3-Thn, P = C(=O)Me |
| 29 | G = C(=O), Q = 3-Py, P = C(=O)Me |
| 30 | G = C(=O), Q = 5-F-3-Py, P = C(=O)Me |
| 31 | G = C(=O), Q = Ph, P = C(=O)CF₃ |
| 32 | G = C(=O), Q = 2-Thn, P = C(=O)CF₃ |
| 33 | G = C(=O), Q = 3-Thn, P = C(=O)CF₃ |
| 34 | G = C(=O), Q = 3-Py, P = C(=O)CF₃ |
| 35 | G = C(=O), Q = 5-F-3-Py, P = C(=O)CF₃ |
| 36 | G = C(=O), Q = Ph, P = CH₂OH |
| 37 | G = C(=O), Q = 2-Thn, P = CH₂OH |
| 38 | G = C(=O), Q = 3-Thn, P = CH₂OH |
| 39 | G = C(=O), Q = 3-Py, P = CH₂OH |
| 40 | G = C(=O), Q = 5-F-3-Py, P = CH₂OH |

| Table | Header Row |
|---|---|
| 41 | G = C(=O), Q = Ph, P = SO$_2$CF$_3$ |
| 42 | G = C(=O), Q = 2-Thn, P = SO$_2$CF$_3$ |
| 43 | G = C(=O), Q = 3-Thn, P = SO$_2$CF$_3$ |
| 44 | G = C(=O), Q = 3-Py, P = SO$_2$CF$_3$ |
| 45 | G = C(=O), Q = 5-F-3-Py, P = SO$_2$CF$_3$ |
| 46 | G = C(=O), Q = Ph, P = SO$_2$NMe$_2$ |
| 47 | G = C(=O), Q = 2-Thn, P = SO$_2$N(Me)$_2$ |
| 48 | G = C(=O), Q = 3-Thn, P = SO$_2$N(Me)$_2$ |
| 49 | G = C(=O), Q = 3-Py, P = SO$_2$N(Me)$_2$ |
| 50 | G = C(=O), Q = 5-F-3-Py, P = SO$_2$N(Me)$_2$ |
| 51 | G = C(=O), Q = Ph, P = CF$_2$H |
| 52 | G = C(=O), Q = 2-Thn, P = CF$_2$H |
| 53 | G = C(=O), Q = 3-Thn, P = CF$_2$H |
| 54 | G = C(=O), Q = 3-Py, P = CF$_2$H |
| 55 | G = C(=O), Q = 5-F-3-Py, P = CF$_2$H |
| 56 | G = C(=O), Q = Ph, P = C(=O)Et |
| 57 | G = C(=O), Q = 2-Thn, P = C(=O)Et |
| 58 | G = C(=O), Q = 3-Thn, P = C(=O)Et |
| 59 | G = C(=O), Q = 3-Py, P = C(O)Et |
| 60 | G = C(=O), Q = Ph, P = SO$_2$CF$_3$ |
| 61 | G = C(=O), Q = 2-Thn, P = SO$_2$CF$_3$ |
| 62 | G = C(=O), Q = 3-Thn, P = SO$_2$CF$_3$ |
| 63 | G = C(=O), Q = 3-Py, P = SO$_2$CF$_3$ |
| 64 | G = C(=O), Q = 5-F-3-Py, P = SO$_2$CF$_3$ |
| 65 | G = C(=O), Q = Ph, P = SO$_2$CH$_2$Cl |
| 66 | G = C(=O), Q = 2-Thn, P = SO$_2$CH$_2$Cl |
| 67 | G = C(=O), Q = 3-Thn, P = SO$_2$CH$_2$Cl |
| 68 | G = C(=O), Q = 3-Py, P = SO$_2$CH$_2$Cl |
| 69 | G = C(=O), Q = 5-F-3-Py, P = SO$_2$CH$_2$Cl |
| 70 | G = C(=O), Q = Ph, P = SO$_2$CH$_2$CF$_3$ |
| 71 | G = C(=O), Q = 2-Thn, P = SO$_2$CH$_2$CF$_3$ |
| 72 | G = C(=O), Q = 3-Thn, P = SO$_2$CH$_2$CF$_3$ |
| 73 | G = C(=O), Q = 3-Py, P = SO$_2$CH$_2$CF$_3$ |
| 74 | G = C(=O), Q = 5-F-3-Py, P = SO$_2$CH$_2$CF$_3$ |
| 75 | G = C(=O), Q = Ph, P = C(=O)i-Pr |
| 76 | G = C(=O), Q = 2-Thn, P = C(=O)i-Pr |
| 77 | G = C(=O), Q = 3-Thn, P = C(=O)i-Pr |
| 78 | G = C(=O), Q = 3-Py, P = C(=O)i-Pr |
| 79 | G = C(=O), Q = 5-F-3-Py, P = C(=O)i-Pr |
| 80 | G = C(=O), Q = Ph, P = C(=O)c-Pr |
| 81 | G = C(=O), Q = 2-Thn, P = C(=O)c-Pr |
| 82 | G = C(=O), Q = 3-Thn, P = C(=O)c-Pr |
| 83 | G = C(=O), Q = 3-Py, P = C(=O)c-Pr |
| 84 | G = C(=O), Q = 5-F-3-Py, P = C(=O)c-Pr |
| 85 | G = C(=O), Q = Ph, P = C(=O)H |
| 86 | G = C(=O), Q = 2-Thn, P = C(=O)H |
| 87 | G = C(=O), Q = 3-Thn, P = C(=O)H |
| 88 | G = C(=O), Q = 3-Py, P = C(=O)H |
| 89 | G = C(=O), Q = 5-F-3-Py, P = C(=O)H |
| 90 | G = C(=O), Q = Ph, P = CH$_2$OMe |
| 91 | G = C(=O), Q = 2-Thn, P = CH$_2$OMe |
| 92 | G = C(=O), Q = 3-Thn, P = CH$_2$OMe |
| 93 | G = C(=O), Q = 3-Py, P = CH$_2$OMe |
| 94 | G = C(=O), Q = 5-F-3-Py, P = CH$_2$OMe |
| 95 | G = C(=O), Q = Ph, P = CH$_2$CH=CH$_2$ |
| 96 | G = C(=O), Q = 2-Thn, P = CH$_2$CH=CH$_2$ |
| 97 | G = C(=O), Q = 3-Thn, P = CH$_2$CH=CH$_2$ |
| 98 | G = C(=O), Q = 3-Py, P = CH$_2$CH=CH$_2$ |
| 99 | G = C(=O), Q = 5-F-3-Py, P = CH$_2$CH=CH$_2$ |
| 100 | G = C(=O), Q = Ph, P = SO$_2$Me |
| 101 | G = C(=O), Q = 2-Thn, P = SO$_2$Me |
| 102 | G = C(=O), Q = 3-Thn, P = SO$_2$Me |
| 103 | G = C(=O), Q = 3-Py, P = SO$_2$Me |
| 104 | G = C(=O), Q = 5-F-3-Py, P = SO$_2$Me |
| 105 | G = C(=O), Q = Ph, P = SO$_2$Ph |
| 106 | G = C(=O), Q = 2-Thn, P = SO$_2$Ph |
| 107 | G = C(=O), Q = 3-Thn, P = SO$_2$Ph |
| 108 | G = C(=O), Q = 3-Py, P = SO$_2$Ph |
| 109 | G = C(=O), Q = 5-F-3-Py, P = SO$_2$Ph |
| 110 | G = C(=O), Q = Ph, P = CH$_2$OAc |
| 111 | G = C(=O), Q = 2-Thn, P = CH$_2$OAc |
| 112 | G = C(=O), Q = 3-Thn, P = CH$_2$OAc |
| 113 | G = C(=O), Q = 3-Py, P = CH$_2$OAc |
| 114 | G = C(=O), Q = 5-F-3-Py, P = CH$_2$OAc |
| 115 | G = C(=O), Q = Ph, P = C(=O)CH$_2$Ph |
| 116 | G = C(=O), Q = 2-Thn, P = C(=O)CH$_2$Ph |
| 117 | G = C(=O), Q = 3-Thn, P = C(=O)CH$_2$Ph |
| 118 | G = C(=O), Q = 3-Py, P = C(=O)CH$_2$Ph |
| 119 | G = C(=O), Q = 5-F-3-Py, P = C(=O)CH$_2$Ph |
| 120 | G = C(=O), Q = Ph, P = CH$_2$C(=O)Me |
| 121 | G = C(=O), Q = 2-Thn, P = CH$_2$C(=O)Me |
| 122 | G = C(=O), Q = 3-Thn, P = CH$_2$C(=O)Me |
| 123 | G = C(=O), Q = 3-Py, P = CH$_2$C(=O)Me |
| 124 | G = C(=O), Q = 5-F-3-Py, P = CH$_2$C(=O)Me |
| 125 | G = C(=O), Q = Ph, P = Ph |
| 126 | G = C(=O), Q = 2-Thn, P = Ph |
| 127 | G = C(=O), Q = 3-Thn, P = Ph |
| 128 | G = C(=O), Q = 3-Py, P = Ph |
| 129 | G = C(=O), Q = 5-F-3-Py, P = Ph |
| 130 | G = C(=O), Q = Ph, P = CH$_2$C(=O)Ph |
| 131 | G = C(=O), Q = 2-Thn, P = CH$_2$C(=O)Ph |
| 132 | G = C(=O), Q = 3-Thn, P = CH$_2$C(=O)Ph |
| 133 | G = C(=O), Q = 3-Py, P = CH$_2$C(=O)Ph |
| 134 | G = C(=O), Q = 5-F-3-Py, P = CH$_2$C(=O)Ph |
| 135 | G = C(=O), Q = Ph, P = i-Pr |
| 136 | G = C(=O), Q = 2-Thn, P = i-Pr |
| 137 | G = C(=O), Q = 3-Thn, P = i-Pr |
| 138 | G = C(=O), Q = 3-Py, P = i-Pr |
| 139 | G = C(=O), Q = 5-F-3-Py, P = i-Pr |
| 140 | G = C(=O), Q = Ph, P = CH$_2$c-Pr |
| 141 | G = C(=O), Q = 2-Thn, P = CH$_2$c-Pr |
| 142 | G = C(=O), Q = 3-Thn, P = CH$_2$c-Pr |
| 143 | G = C(=O), Q = 3-Py, P = CH$_2$c-Pr |
| 144 | G = C(=O), Q = 5-F-3-Py, P = CH$_2$c-Pr |
| 145 | G = C(=O), Q = Ph, P = CH$_2$CF$_2$H |
| 146 | G = C(=O), Q = 2-Thn, P = CH$_2$CF$_2$H |
| 147 | G = C(=O), Q = 3-Thn, P = CH$_2$CF$_2$H |
| 148 | G = C(=O), Q = 3-Py, P = CH$_2$CF$_2$H |
| 149 | G = C(=O), Q = 5-F-3-Py, P = CH$_2$CF$_2$H |
| 150 | G = C(=O), Q = Ph, P = CH$_2$CF$_3$ |
| 151 | G = C(=O), Q = 2-Thn, P = CH$_2$CF$_3$ |
| 152 | G = C(=O), Q = 3-Thn, P = CH$_2$CF$_3$ |
| 153 | G = C(=O), Q = 3-Py, P = CH$_2$CF$_3$ |
| 154 | G = C(=O), Q = 5-F-3-Py, P = CH$_2$CF$_3$ |
| 155 | G = C(=O), Q = Ph, P = CH$_2$CN |
| 156 | G = C(=O), Q = 2-Thn, P = CH$_2$CN |
| 157 | G = C(=O), Q = 3-Thn, P = CH$_2$CN |
| 158 | G = C(=O), Q = 3-Py, P = CH$_2$CN |
| 159 | G = C(=O), Q = 5-F-3-Py, P = CH$_2$CN |
| 160 | G = C(=O), Q = Ph, P = CH$_2$C(=O)N(Me)$_2$ |
| 161 | G = C(=O), Q = 2-Thn, P = CH$_2$C(=O)N(Me)$_2$ |
| 162 | G = C(=O), Q = 3-Thn, P = CH$_2$C(=O)N(Me)$_2$ |
| 163 | G = C(=O), Q = 3-Py, P = CH$_2$C(=O)N(Me)$_2$ |
| 164 | G = C(=O), Q = 5-F-3-Py, P = CH$_2$C(=O)N(Me)$_2$ |
| 165 | G = C(=O), Q = Ph, P = CH$_2$C(=O)NHMe |
| 166 | G = C(=O), Q = 2-Thn, P = CH$_2$C(=O)NHMe |
| 167 | G = C(=O), Q = 3-Thn, P = CH$_2$C(=O)NHMe |
| 168 | G = C(=O), Q = 3-Py, P = CH$_2$C(=O)NHMe |
| 169 | G = C(=O), Q = 5-F-3-Py, P = CH$_2$C(=O)NHMe |
| 170 | G = C(=O), Q = Ph, P = NH$_2$ |
| 171 | G = C(=O), Q = 2-Thn, P = NH$_2$ |
| 172 | G = C(=O), Q = 3-Thn, P = NH$_2$ |
| 173 | G = C(=O), Q = 3-Py, P = NH$_2$ |
| 174 | G = C(=O), Q = 5-F-3-Py, P = NH$_2$ |
| 175 | G = C(=O), Q = Ph, P = CH$_2$C(=O)OMe |
| 176 | G = C(=O), Q = 2-Thn, P = CH$_2$C(=O)OMe |
| 177 | G = C(=O), Q = 3-Thn, P = CH$_2$C(=O)OMe |
| 178 | G = C(=O), Q = 3-Py, P = CH$_2$C(=O)OMe |
| 179 | G = C(=O), Q = 5-F-3-Py, P = CH$_2$C(=O)OMe |
| 180 | G = C(=NNH(2-F—Ph)), Q = Ph, P = H |
| 181 | G = C(=NNH(2-F—Ph)), Q = 2-Thn, P = H |
| 182 | G = C(=NNH(2-F—Ph)), Q = 3-Thn, P = H |
| 183 | G = C(=NNH(2-F—Ph)), Q = 5-F-3-Py, P = H |
| 184 | G = C(=NNH(2-F—Ph)), Q = 3-Py, P = H |
| 185 | G = C(=NNH(3-F—Ph)), Q = Ph, P = H |
| 186 | G = C(=NNH(3-F—Ph)), Q = 2-Thn, P = H |
| 187 | G = C(=NNH(3-F—Ph)), Q = 3-Thn, P = H |
| 188 | G = C(=NNH(3-F—Ph)), Q = 3-Py, P = H |
| 189 | G = C(=NNH(3-F—Ph)), Q = 5-F-3-Py, P = H |
| 190 | G = C(=NN-pyrr), Q = Ph, P = H |
| 191 | G = C(=NN-pyrr), Q = 2-Thn, P = H |
| 192 | G = C(=NN-pyrr), Q = 3-Thn, P = H |
| 193 | G = C(=NN-pyrr), Q = 3-Py, P = H |
| 194 | G = C(=NN-pyrr), Q = 5-F-3-Py, P = H |

-continued

| Table | Header Row |
|---|---|
| 195 | G = C(=NN-pyrr), Q = Ph, P = H |
| 196 | G = C(=NN-pip), Q = 2-Thn, P = H |
| 197 | G = C(=NN-pip), Q = 3-Thn, P = H |
| 198 | G = C(=NN-pip), Q = 3-Py, P = H |
| 199 | G = C(=NN-pip), Q = 5-F-3-Py, P = H |
| 200 | G = C(=NN-morph), Q = Ph, P = H |
| 201 | G = C(=NN-morph), Q = 2-Thn, P = H |
| 202 | G = C(=NN-morph), Q = 3-Thn, P = H |
| 203 | G = C(=NN-morph), Q = 3-Py, P = H |
| 204 | G = C(=NN-morph), Q = 5-F-3-Py, P = H |
| 205 | G = C(=NNHPh), Q = Ph, P = H |
| 206 | G = C(=NNHPh), Q = 2-Thn, P = H |
| 207 | G = C(=NNHPh), Q = 3-Thn, P = H |
| 208 | G = C(=NNHPh), Q = 3-Py, P = H |
| 209 | G = C(=NNHPh), Q = 5-F-3-Py, P = H |
| 210 | G = C(=NNH(2-Cl—Ph)), Q = Ph, P = H |
| 211 | G = C(=NNH(2-Cl—Ph)), Q = 2-Thn, P = H |
| 212 | G = C(=NNH(2-Cl—Ph)), Q = 3-Thn, P = H |
| 213 | G = C(=NNH(2-Cl—Ph)), Q = 3-Py, P = H |
| 214 | G = C(=NNH(2-Cl—Ph)), Q = 5-F-3-Py, P = H |
| 215 | G = C(=NNH(3-Cl—Ph)), Q = Ph, P = H |
| 216 | G = C(=NNH(3-Cl—Ph)), Q = 2-Thn, P = H |
| 217 | G = C(=NNH(3-Cl—Ph)), Q = 3-Thn, P = H |
| 218 | G = C(=NNH(3-Cl—Ph)), Q = 3-Py, P = H |
| 219 | G = C(=NNH(3-Cl—Ph)), Q = 5-F-3-Py, P = H |
| 220 | G = C(=NNH(4-Cl—Ph)), Q = Ph, P = H |
| 221 | G = C(=NNH(4-Cl—Ph)), Q = 2-Thn, P = H |
| 222 | G = C(=NNH(4-Cl—Ph)), Q = 3-Thn, P = H |
| 223 | G = C(=NNH(4-Cl—Ph)), Q = 3-Py, P = H |
| 224 | G = C(=NNH(4-Cl—Ph)), Q = 5-F-3-Py, P = H |
| 225 | G = C(=NCN), Q = Ph, P = H |
| 226 | G = C(=NCN), Q = 2-Thn, P = H |
| 227 | G = C(=NCN), Q = 3-Thn, P = H |
| 228 | G = C(=NCN), Q = 3-Py, P = H |
| 229 | G = C(=NCN), Q = 5-F-3-Py, P = H |
| 230 | G = C(=NOMe), Q = Ph, P = H |
| 231 | G = C(=NOMe), Q = 2-Thn, P = H |
| 232 | G = C(=NOMe), Q = 3-Thn, P = H |
| 233 | G = C(=NOMe), Q = 3-Py, P = H |
| 234 | G = C(=NOMe), Q = 5-F-3-Py, P = H |
| 235 | G = C(=NNHC(=O)OMe), Q = Ph, P = H |
| 236 | G = C(=NNHC(=O)OMe), Q = 2-Thn, P = H |
| 237 | G = C(=NNHC(=O)OMe), Q = 3-Thn, P = H |
| 238 | G = C(=NNHC(=O)OMe), Q = 3-Py, P = H |
| 239 | G = C(=NNHC(=O)OMe), Q = 5-F-3-Py, P = H |
| 240 | G = C(=NNHC(=O)OEt), Q = Ph, P = H |
| 241 | G = C(=NNHC(=O)OEt), Q = 2-Thn, P = H |
| 242 | G = C(=NNHC(=O)OEt), Q = 3-Thn, P = H |
| 243 | G = C(=NNHC(=O)OEt), Q = 3-Py, P = H |
| 244 | G = C(=NNHC(=O)OEt, Q = 5-F-3-Py, P = H |
| 245 | G = C(=NH), Q = Ph, P = H |
| 246 | G = C(=NH), Q = 2-Thn, P = H |
| 247 | G = C(=NH), Q = 3-Thn, P = H |
| 248 | G = C(=NH), Q = 3-Py, P = H |
| 249 | G = C(=NH), Q = 5-F-3-Py, P = H |
| 250 | G = C(=NCH$_2$Me), Q = Ph, P = H |
| 251 | G = C(=NCH$_2$Me), Q = 2-Thn, P = H |
| 252 | G = C(=NCH$_2$Me), Q = 3-Thn, P = H |
| 253 | G = C(=NCH$_2$Me), Q = 3-Py, P = H |
| 254 | G = C(=NCH$_2$Me), Q = 5-F-3-Py, P = H |
| 255 | G = C(1,3-dithiolan-2-yl), Q = Ph, P = H |
| 256 | G = C(1,3-dithiolan-2-yl), Q = 2-Thn, P = H |
| 257 | G = C(1,3-dithiolan-2-yl), Q = 3-Thn, P = H |
| 258 | G = C(1,3-dithiolan-2-yl), Q = 3-Py, P = H |
| 259 | G = C(1,3-dithiolan-2-yl), Q = 5-F-3-Py, P = H |
| 260 | G = C(1,3-dithian-2-yl), Q = Ph, P = H |
| 261 | G = C(1,3-dithian-2-yl), Q = 2-Thn, P = H |
| 262 | G = C(1,3-dithian-2-yl), Q = 3-Thn, P = H |
| 263 | G = C(1,3-dithian-2-yl), Q = 3-Py, P = H |
| 264 | G = C(1,3-dithian-2-yl), Q = 5-F-3-Py, P = H |

A compound of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diPh sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents,* annual American and International Editions published by McCutcheon's Division, The Manufacturing Confectioner Publishing Co.; Sisely and Wood, *Encyclopedia of Surface Active Agents,* Chemical Publ. Co., Inc., New York, 1964; and A. S. Davidson and B. Milwidsky, *Synthetic Detergents,* Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food—Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Table A. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

| High Strength Concentrate | |
|---|---|
| Compound 2, 13, 14, 15, 16, 30, 31, 39, 54, or 61 | 98.5% |
| silica aerogel | 0.5% |
| synthetic amorphous fine silica | 1.0% |

Example B

| Wettable Powder | |
|---|---|
| Compound 2, 13, 14, 15, 16, 30, 31, 39, 54, or 61 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| Compound 2, 13, 14, 15, 16, 30, 31, 39, 54, or 61 | 10.0% |
| attapulgite granules (low volatile matter, 0.71/0.30 mm; U.S.S. No. 25-50 sieves) | 90.0% |

Example D

| Extruded Pellet | |
|---|---|
| Compound 2, 13, 14, 15, 16, 30, 31, 39, 54, or 61 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
|---|---|
| Compound 2, 13, 14, 15, 16, 30, 31, 39, 54, or 61 | 10.0% |
| polyoxyethylene sorbitol hexoleate | 20.0% |
| $C_6$-$C_{10}$ fatty acid methyl ester | 70.0% |

Example F

| Microemulsion | |
|---|---|
| Compound 2, 13, 14, 15, 16, 30, 31, 39, 54, or 61 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Suspension Concentrate | |
|---|---|
| Compound 2, 13, 14, 15, 16, 30, 31, 39, 54, or 61 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example H

| Emulsion in Water | |
|---|---|
| Compound 2, 13, 14, 15, 16, 30, 31, 39, 54, or 61 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Test results indicate that the compounds of the present invention are highly active preemergent and/or postemergent herbicides and/or plant growth regulants. The compounds of the mention generally show highest activity for postemergence weed control (i.e. applied after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g., loblolly pine), and turf species (e.g., Kentucky bluegrass, St. Augustine grass, Kentucky fescue and Bermuda grass). Compounds of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the invention have both preemergent and postemergent herbicidal activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

As referred to herein Asteraceae is a plant family which includes the genera *Ambrosia* and *Bidens*; Brassicaceae is a plant family which includes the genera *Brassica, Raphanus* and *Sinapis*; Amaranthaceae is a plant family which includes the genera *Amaranthus*; Chenopodiaceae is a plant family which includes the genera *Chenopodium* and *Kochia*; Malvaceae is a plant family which includes the genera *Abutilon* and *Sida*; Papaveraceae is a plant family which includes the genera *Papaver*; Rubiaceae is a plant family which includes the genera *Galium*; Scrophulariaceae is a plant family which includes the genera *Veronica*; and Violaceae is a plant family which includes the genera *Viola*. As referred to herein, the term "pigweed" includes species of the genus *Amaranthus*. Species of pigweed for which control is often desired include *A. retroflexus* L. (redroot pigweed), *A. palmeri* (palmer pigweed), and *A. rudis* (common waterhemp). As referred to herein "chickweed" includes species of the genus *Stellaria*. Species of chickweed for which control is often desired include *S. media* (L.) Vill. (common chickweed). As referred to herein "velvetleaf" includes species of the genus *Abutilon*. Species of velvetleaf for which control is often desired include *A. theophrasti* Medik. (velvetleaf). As referred to herein "lambsquarters" includes species of the genus *Chenopodium*. Species of lambsquarters for which control is often desired include *C. album* L. (common lambsquarters). Therefore, one aspect of this invention includes a method of applying a compound of Formula 1 to control the growth of *Amaranthus, Stellaria* and *Abutilon*.

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.001 to 20 kg/ha with a preferred range of about 0.004 to 1 kg/ha. One skilled in the art can easily determine the herbicidally effective amount necessary for the desired level of weed control.

Compounds of the invention are useful in treating all plants and plant parts. Plant varieties and cultivars can be obtained by conventional propagation and breeding methods or by genetic engineering methods. Genetically modified plants (transgenic plants) are those in which a heterologous gene (transgene) has been stably integrated into the plant's genome. A transgene that is defined by its particular location in the plant genome is called a transformation or transgenic event.

Genetically modified plant cultivars which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect-resistance, modified oil profiles or drought tolerance. Useful genetically modified plants containing single gene transformation events or combinations of transformation events are listed in Exhibit C. Additional information for the genetic modifications listed in Exhibit C can be obtained from publicly available databases maintained, for example, by the U.S. Department of Agriculture.

The following abbreviations, T1 through T37, are used in Exhibit C for traits. A "-" means the entry is not available. In the following tables "tol." means tolerance.

| Trait | Description |
| --- | --- |
| T1 | Glyphosate tol. |
| T2 | High lauric acid oil |
| T3 | Glufosinate tol. |
| T4 | Phytate breakdown |
| T5 | Oxynil tol. |
| T6 | Disease resistance |
| T7 | Insect resistance |
| T9 | Modified flower color |
| T11 | ALS Herbicide tol. |
| T12 | Dicamba tol. |
| T13 | Anti-allergy |

-continued

| Trait | Description |
| --- | --- |
| T14 | Salt tol. |
| T15 | Cold tol. |
| T16 | Imidazolinone herb. tol. |
| T17 | Modified alpha-amylase |
| T18 | Pollination control |
| T19 | 2,4-D tol. |
| T20 | Increased lysine |
| T21 | Drought tol. |
| T22 | Delayed ripening/senescence |
| T23 | Modified product quality |
| T24 | High cellulose |
| T25 | Modified starch/carbohydrate |
| T26 | Insect & disease resist. |
| T27 | High tryptophan |
| T28 | Erect leaves semidwarf |
| T29 | Semidwarf |
| T30 | Low iron tol. |
| T31 | Modified oil/fatty acid |
| T32 | HPPD tol. |
| T33 | High oil |
| T34 | Aryloxyalkanoate tol. |
| T35 | Mesotrione tol. |
| T36 | Reduced nicotine |
| T37 | Modified product |

Exhibit C

| Crop | Event Name | Event Code | Trait(s) | Gene(s) |
| --- | --- | --- | --- | --- |
| Alfalfa | J101 | MON-00101-8 | T1 | cp4 epsps (aroA:CP4) |
| Alfalfa | J163 | MON-ØØ163-7 | T1 | cp4 epsps (aroA:CP4) |
| Canola* | 23-18-17 (Event 18) | CGN-89465-2 | T2 | te |
| Canola* | 23-198 (Event 23) | CGN-89465-2 | T2 | te |
| Canola* | 61061 | DP-Ø61061-7 | T1 | gat4621 |
| Canola* | 73496 | DP-Ø73496-4 | T1 | gat4621 |
| Canola* | GT200 (RT200) | MON-89249-2 | T1 | cp4 epsps (aroA:CP4); goxv247 |
| Canola* | GT73 (RT73) | MON-ØØØ73-7 | T1 | cp4 epsps (aroA:CP4); goxv247 |
| Canola* | HCN10 (Topas 19/2) | — | T3 | bar |
| Canola* | HCN28 (T45) | ACS-BNØØ8-2 | T3 | pat (syn) |
| Canola* | HCN92 (Topas 19/2) | ACS-BNØØ7-1 | T3 | bar |
| Canola* | MON88302 | MON-883Ø2-9 | T1 | cp4 epsps (aroA:CP4) |
| Canola* | MPS961 | — | T4 | phyA |
| Canola* | MPS962 | — | T4 | phyA |
| Canola* | MPS963 | — | T4 | phyA |
| Canola* | MPS964 | — | T4 | phyA |
| Canola* | MPS965 | — | T4 | phyA |
| Canola* | MS1 (B91-4) | ACS-BNØØ4-7 | T3 | bar |
| Canola* | MS8 | ACS-BNØØ5-8 | T3 | bar |
| Canola* | OXY-235 | ACS-BNØ11-5 | T5 | bxn |
| Canola* | PHY14 | — | T3 | bar |
| Canola* | PHY23 | — | T3 | bar |
| Canola* | PHY35 | — | T3 | bar |
| Canola* | PHY36 | — | T3 | bar |
| Canola* | RF1 (B93-101) | ACS-BNØØ1-4 | T3 | bar |
| Canola* | RF2 (B94-2) | ACS-BNØØ2-5 | T3 | bar |
| Canola* | RF3 | ACS-BNØØ3-6 | T3 | bar |
| Bean | EMBRAPA 5.1 | EMB-PV051-1 | T6 | acl (sense and antisense) |
| Brinjal # | EE-1 | — | T7 | cry1Ac |
| Cotton | 19-51a | DD-Ø1951A-7 | T11 | S4-HrA |
| Cotton | 281-24-236 | DAS-24236-5 | T3, T7 | pat (syn); cry1F |
| Cotton | 3006-210-23 | DAS-21Ø23-5 | T3, T7 | pat (syn); cry1Ac |
| Cotton | 31707 | — | T5, T7 | bxn; cry1Ac |
| Cotton | 31803 | — | T5, T7 | bxn; cry1Ac |
| Cotton | 31807 | — | T5, T7 | bxn; cry1Ac |
| Cotton | 31808 | — | T5, T7 | bxn; cry1Ac |
| Cotton | 42317 | — | T5, T7 | bxn; cry1Ac |
| Cotton | BNLA-601 | — | T7 | cry1Ac |
| Cotton | BXN10211 | BXN10211-9 | T5 | bxn; cry1Ac |
| Cotton | BXN10215 | BXN10215-4 | T5 | bxn; cry1Ac |
| Cotton | BXN10222 | BXN10222-2 | T5 | bxn; cry1Ac |
| Cotton | BXN10224 | BXN10224-4 | T5 | bxn; cry1Ac |
| Cotton | COT102 | SYN-IR102-7 | T7 | vip3A(a) |
| Cotton | COT67B | SYN-IR67B-1 | T7 | cry1Ab |
| Cotton | COT202 | — | T7 | vip3A |

-continued

| Crop | Event Name | Event Code | Trait(s) | Gene(s) |
|---|---|---|---|---|
| Cotton | Event 1 | — | T7 | cry1Ac |
| Cotton | GMF Cry1A | GTL-GMF311-7 | T7 | cry1Ab-Ac |
| Cotton | GHB119 | BCS-GH005-8 | T7 | cry2Ae |
| Cotton | GHB614 | BCS-GH002-5 | T1 | 2mepsps |
| Cotton | GK12 | — | T7 | cry1Ab-Ac |
| Cotton | LLCotton25 | ACS-GH001-3 | T3 | bar |
| Cotton | MLS 9124 | — | T7 | cry1C |
| Cotton | MON1076 | MON-89924-2 | T7 | cry1Ac |
| Cotton | MON1445 | MON-01445-2 | T1 | cp4 epsps (aroA:CP4) |
| Cotton | MON15985 | MON-15985-7 | T7 | cry1Ac; cry2Ab2 |
| Cotton | MON1698 | MON-89383-1 | T1 | cp4 epsps (aroA:CP4) |
| Cotton | MON531 | MON-00531-6 | T7 | cry1Ac |
| Cotton | MON757 | MON-00757-7 | T7 | cry1Ac |
| Cotton | MON88913 | MON-88913-8 | T1 | cp4 epsps (aroA:CP4) |
| Cotton | Nqwe Chi 6 Bt | — | T7 | — |
| Cotton | SKG321 | — | T7 | cry1A; CpTI |
| Cotton | T303-3 | BCS-GH003-6 | T3, T7 | cry1Ab; bar |
| Cotton | T304-40 | BCS-GH004-7 | T3, T7 | cry1Ab; bar |
| Cotton | CE43-67B | — | T7 | cry1Ab |
| Cotton | CE46-02A | — | T7 | cry1Ab |
| Cotton | CE44-69D | — | T7 | cry1Ab |
| Cotton | 1143-14A | — | T7 | cry1Ab |
| Cotton | 1143-51B | — | T7 | cry1Ab |
| Cotton | T342-142 | — | T7 | cry1Ab |
| Cotton | PV-GHGT07 (1445) | — | T1 | cp4 epsps (aroA:CP4) |
| Cotton | EE-GH3 | — | T1 | mepsps |
| Cotton | EE-GH5 | — | T7 | cry1Ab |
| Cotton | MON88701 | MON-88701-3 | T3, T12 | Modified dmo; bar |
| Cotton | OsCr11 | — | T13 | Modified Cry j |
| Flax | FP967 | CDC-FL001-2 | T11 | als |
| Lentil | RH44 | — | T16 | als |
| Maize | 3272 | SYN-E3272-5 | T17 | amy797E |
| Maize | 5307 | SYN-05307-1 | T7 | ecry3.1Ab |
| Maize | 59122 | DAS-59122-7 | T3, T7 | cry34Ab1; cry35Ab1; pat |
| Maize | 676 | PH-000676-7 | T3, T18 | pat; dam |
| Maize | 678 | PH-000678-9 | T3, T18 | pat; dam |
| Maize | 680 | PH-000680-2 | T3, T18 | pat; dam |
| Maize | 98140 | DP-098140-6 | T1, T11 | gat4621; zm-hra |
| Maize | Bt10 | — | T3, T7 | cry1Ab; pat |
| Maize | Bt176 (176) | SYN-EV176-9 | T3, T7 | cry1Ab; bar |
| Maize | BVLA430101 | — | T4 | phyA2 |
| Maize | CBH-351 | ACS-ZM004-3 | T3, T7 | cry9C; bar |
| Maize | DAS40278-9 | DAS40278-9 | T19 | aad-1 |
| Maize | DBT418 | DKB-89614-9 | T3, T7 | cry1Ac; pinII; bar |
| Maize | DLL25 (B16) | DKB-89790-5 | T3 | bar |
| Maize | GA21 | MON-00021-9 | T1 | mepsps |
| Maize | GG25 | — | T1 | mepsps |
| Maize | GJ11 | — | T1 | mepsps |
| Maize | FI117 | — | T1 | mepsps |
| Maize | GAT-ZM1 | — | T3 | pat |
| Maize | LY038 | REN-00038-3 | T20 | cordapA |
| Maize | MIR162 | SYN-IR162-4 | T7 | vip3Aa20 |
| Maize | MIR604 | SYN-IR604-5 | T7 | mcry3A |
| Maize | MON801 (MON80100) | MON801 | T1, T7 | cry1Ab; cp4 epsps (aroA:CP4); goxv247 |
| Maize | MON802 | MON-80200-7 | T1, T7 | cry1Ab; cp4 epsps (aroA:CP4); goxv247 |
| Maize | MON809 | PH-MON-809-2 | T1, T7 | cry1Ab; cp4 epsps (aroA:CP4); goxv247 |
| Maize | MON810 | MON-00810-6 | T1, T7 | cry1Ab; cp4 epsps (aroA:CP4); goxv247 |
| Maize | MON832 | — | T1 | cp4 epsps (aroA:CP4); goxv247 |
| Maize | MON863 | MON-00863-5 | T7 | cry3Bb1 |
| Maize | MON87427 | MON-87427-7 | T1 | cp4 epsps (aroA:CP4) |
| Maize | MON87460 | MON-87460-4 | T21 | cspB |
| Maize | MON88017 | MON-88017-3 | T1, T7 | cry3Bb1; cp4 epsps (aroA:CP4) |
| Maize | MON89034 | MON-89034-3 | T7 | cry2Ab2; cry1A.105 |
| Maize | MS3 | ACS-ZM001-9 | T3, T18 | bar; barnase |
| Maize | MS6 | ACS-ZM005-4 | T3, T18 | bar; barnase |
| Maize | NK603 | MON-00603-6 | T1 | cp4 epsps (aroA:CP4) |
| Maize | T14 | ACS-ZM002-1 | T3 | pat (syn) |
| Maize | T25 | ACS-ZM003-2 | T3 | pat (syn) |
| Maize | TC1507 | DAS-01507-1 | T3, T7 | cry1Fa2; pat |
| Maize | TC6275 | DAS-06275-8 | T3, T7 | mocry1F; bar |
| Maize | VIP1034 | — | T3, T7 | vip3A; pat |
| Maize | 43A47 | DP-043A47-3 | T3, T7 | cry1F; cry34Ab1; cry35Ab1; pat |
| Maize | 40416 | DP-040416-8 | T3, T7 | cry1F; cry34Ab1; cry35Ab1; pat |

| Crop | Event Name | Event Code | Trait(s) | Gene(s) |
|---|---|---|---|---|
| Maize | 32316 | DP-032316-8 | T3, T7 | cry1F; cry34Ab1; cry35Ab1; pat |
| Maize | 4114 | DP-004114-3 | T3, T7 | cry1F; cry34Ab1; cry35Ab1; pat |
| Melon | Melon A | — | T22 | sam-k |
| Melon | Melon B | — | T22 | sam-k |
| Papaya | 55-1 | CUH-CP551-8 | T6 | prsv cp |
| Papaya | 63-1 | CUH-CP631-7 | T6 | prsv cp |
| Papaya | Huanong No. 1 | — | T6 | prsv rep |
| Papaya | X17-2 | UFL-X17CP-6 | T6 | prsv cp |
| Plum | C-5 | ARS-PLMC5-6 | T6 | ppv cp |
| Canola** | ZSR500 | — | T1 | cp4 epsps (aroA:CP4); goxv247 |
| Canola** | ZSR502 | — | T1 | cp4 epsps (aroA:CP4); goxv247 |
| Canola** | ZSR503 | — | T1 | cp4 epsps (aroA:CP4); goxv247 |
| Rice | 7Crp#242-95-7 | — | T13 | 7crp |
| Rice | 7Crp#10 | — | T13 | 7crp |
| Rice | GM Shanyou 63 | — | T7 | cry1Ab; cry1Ac |
| Rice | Huahui-1/TT51-1 | — | T7 | cry1Ab; cry1Ac |
| Rice | LLRICE06 | ACS-OS001-4 | T3 | bar |
| Rice | LLRICE601 | BCS-OS003-7 | T3 | bar |
| Rice | LLRICE62 | ACS-OS002-5 | T3 | bar |
| Rice | Tarom molaii + cry1Ab | — | T7 | cry1Ab (truncated) |
| Rice | GAT-OS2 | — | T3 | bar |
| Rice | GAT-OS3 | — | T3 | bar |
| Rice | PE-7 | — | T7 | Cry1Ac |
| Rice | 7Crp#10 | — | T13 | 7crp |
| Rice | KPD627-8 | — | T27 | OASA1D |
| Rice | KPD722-4 | — | T27 | OASA1D |
| Rice | KA317 | — | T27 | OASA1D |
| Rice | HW5 | — | T27 | OASA1D |
| Rice | HW1 | — | T27 | OASA1D |
| Rice | B-4-1-18 | — | T28 | Δ OsBRl1 |
| Rice | G-3-3-22 | — | T29 | OSGA2ox1 |
| Rice | AD77 | — | T6 | DEF |
| Rice | AD51 | — | T6 | DEF |
| Rice | AD48 | — | T6 | DEF |
| Rice | AD41 | — | T6 | DEF |
| Rice | 13pNasNa800725atAprt1 | — | T30 | HvNAS1; HvNAAT-A; APRT |
| Rice | 13pAprt1 | — | T30 | APRT |
| Rice | gHvNAS1-gHvNAAT-1 | — | T30 | HvNAS1; HvNAAT-A; HvNAAT-B |
| Rice | gHvIDS3-1 | — | T30 | HvIDS3 |
| Rice | gHvNAAT1 | — | T30 | HvNAAT-A; HvNAAT-B |
| Rice | gHvNAS1-1 | — | T30 | HvNAS1 |
| Rice | NIA-OS006-4 | — | T6 | WRKY45 |
| Rice | NIA-OS005-3 | — | T6 | WRKY45 |
| Rice | NIA-OS004-2 | — | T6 | WRKY45 |
| Rice | NIA-OS003-1 | — | T6 | WRKY45 |
| Rice | NIA-OS002-9 | — | T6 | WRKY45 |
| Rice | NIA-OS001-8 | — | T6 | WRKY45 |
| Rice | OsCr11 | — | T13 | Modified Cry j |
| Rice | 17053 | — | T1 | cp4 epsps (aroA:CP4) |
| Rice | 17314 | — | T1 | cp4 epsps (aroA:CP4) |
| Rose | WKS82/130-4-1 | IFD-52401-4 | T9 | 5AT; bp40 (f3'5'h) |
| Rose | WKS92/130-9-1 | IFD-52901-9 | T9 | 5AT; bp40 (f3'5'h) |
| Soybean | 260-05 (G94-1, G94-19, G168) | — | T9 | gm-fad2-1 (silencing locus) |
| Soybean | A2704-12 | ACS-GM005-3 | T3 | pat |
| Soybean | A2704-21 | ACS-GM004-2 | T3 | pat |
| Soybean | A5547-127 | ACS-GM006-4 | T3 | pat |
| Soybean | A5547-35 | ACS-GM008-6 | T3 | pat |
| Soybean | CV127 | BPS-CV127-9 | T16 | csr1-2 |
| Soybean | DAS68416-4 | DAS68416-4 | T3 | pat |
| Soybean | DP305423 | DP-305423-1 | T11, T31 | gm-fad2-1 (silencing locus); gm-hra |
| Soybean | DP356043 | DP-356043-5 | T1, T31 | gm-fad2-1 (silencing locus); gat4601 |
| Soybean | FG72 | MST-FG072-3 | T32, T1 | 2mepsps; hppdPF W336 |
| Soybean | GTS 40-3-2 (40-3-2) | MON-04032-6 | T1 | cp4 epsps (aroA:CP4) |
| Soybean | GU262 | ACS-GM003-1 | T3 | pat |
| Soybean | MON87701 | MON-87701-2 | T7 | cry1Ac |
| Soybean | MON87705 | MON-87705-6 | T1, T31 | fatb1-A (sense & antisense); fad2-1A (sense & antisense); cp4 epsps (aroA:CP4) |
| Soybean | MON87708 | MON-87708-9 | T1, T12 | dmo; cp4 epsps (aroA:CP4) |
| Soybean | MON87769 | MON-87769-7 | T1, T31 | Pj.D6D; Nc.Fad3; cp4 epsps (aroA:CP4) |
| Soybean | MON89788 | MON-89788-1 | T1 | cp4 epsps (aroA:CP4) |
| Soybean | W62 | ACS-GM002-9 | T3 | bar |
| Soybean | W98 | ACS-GM001-8 | T3 | bar |
| Soybean | MON87754 | MON-87754-1 | T33 | dgat2A |

-continued

| Crop | Event Name | Event Code | Trait(s) | Gene(s) |
|---|---|---|---|---|
| Soybean | DAS21606 | DAS-21606 | T34, T3 | Modified aad-12; pat |
| Soybean | DAS44406 | DAS-44406-6 | T1, T3, T34 | Modified aad-12; 2mepsps; pat |
| Soybean | SYHT04R | SYN-0004R-8 | T35 | Modified avhppd |
| Soybean | 9582.814.19.1 | — | T3, T7 | cry1Ac, cry1F, PAT |
| Squash | CZW3 | SEM-ØCZW3-2 | T6 | cmv cp, zymv cp, wmv cp |
| Squash | ZW20 | SEM-0ZW20-7 | T6 | zymv cp, wmv cp |
| Sugar Beet | GTSB77 (T9100152) | SY-GTSB77-8 | T1 | cp4 epsps (aroA:CP4); goxv247 |
| Sugar Beet | H7-1 | KM-000H71-4 | T1 | cp4 epsps (aroA:CP4) |
| Sugar Beet | T120-7 | ACS-BV001-3 | T3 | pat |
| Sugar Beet | T227-1 | — | T1 | cp4 epsps (aroA:CP4) |
| Sugarcane | NXI-1T | — | T21 | EcbetA |
| Sunflower | X81359 | — | T16 | als |
| Pepper | PK-SP01 | — | T6 | cmv cp |
| Tobacco | C/F/93/08-02 | — | T5 | bxn |
| Tobacco | Vector 21-41 | — | T36 | NtQPT1 (antisense) |
| Sunflower | X81359 | — | T16 | als |
| Wheat | MON71800 | MON-718ØØ-3 | T1 | cp4 epsps (aroA:CP4) |

*Argentine (*Brassica napus*),
**Polish (*B. rapa*),
Eggplant

Treatment of genetically modified plants with compounds of the invention may result in super-additive or synergistic effects. For example, reduction in application rates, broadening of the activity spectrum, increased tolerance to biotic/abiotic stresses or enhanced storage stability may be greater than expected from just simple additive effects of the application of compounds of the invention on genetically modified plants.

Compounds of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the invention with other herbicides can broaden the spectrum of activity against additional weed species, and suppress the proliferation of any resistant biotypes. Thus the present invention also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, clodinafop-propargyl, clomazone, clomeprop, clopyralid, clopyralid-olamine, cloransulam-methyl, cumyluron, cyanazine, cycloate, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxy sulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, topramezone, tralkoxydim, tri-allate, triafamone, triasulfuron, triaziflam, tribenuron-methyl, triclopyr, triclopyr-butotyl, triclopyr-triethylammonium, tridiphane, trietazine, trifloxysulfuron, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3 (2H)-pyridazinone), 5-[[(2,6-difluorophenyl)methoxy]methyl]-4,5-dihydro-5-methyl-3-(3-methyl-2-thienyl)isoxazole (previously methioxolin), 3-[7-fluoro-3,4-dihydro-3-oxo-4-(2-propyn-1-yl)-2H-1,4-benzoxazin-6-yl]dihydro-1,5-dimethyl-6-thioxo-1,3,5-triazine-2,4(1H,3H)-dione, 4-(4-fluorophenyl)-6-[(2-hydroxy-6-oxo-1-cyclohexen-1-yl) carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methylsulfonyl)-N-(1-methyl-1H-tetrazol-5-yl)-4-(trifluoromethyl)benzamide and 2-methyl-N-(4-methyl-1,2,5-oxadiazol-3-yl)-3-(methylsulfinyl)-4-(trifluoromethyl) benzamide. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual*, 13th Edition, C. D. S. Tomlin, Ed., British Crop Protection Council, Farnham, Surrey, U.K., 2003 and *The BioPesticide Manual*, 2nd Edition, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this invention with other biologically active (particularly herbicidal) compounds or agents (i.e. active ingredients) can result in a greater-than-additive (i.e. synergistic) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When synergism of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the invention with at least one other herbicidal active ingredient. Of particular note is such a combination where the other herbicidal active ingredient has different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Compounds of this invention can also be used in combination with herbicide safeners such as allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone naphthalic anhydride (1,8-naphthalic anhydride), oxabetrinil, N-(aminocarbonyl)-2-methylbenzenesulfonamide, N-(aminocarbonyl)-2-fluorobenzenesulfonamide, 1-bromo-4-[(chloromethyl)sulfonyl]benzene (BCS), 4-(dichloroacetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimidinecarboxylate to increase safety to certain crops. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Of note is a composition comprising a compound of the invention (in a herbicidally effective amount), at least one additional active ingredient selected from the group consisting of other herbicides and herbicide safeners (in an effective amount), and at least one component selected from the group consisting of surfactants, solid diluents and liquid diluents. Table A1 lists specific combinations of a Component (a) with Component (b) illustrative of the mixtures, compositions and methods of the present invention. Compound 2 in the Component (a) column is identified in Index Table A. The second column of Table A1 lists the specific Component (b) compound (e.g., "2,4-D" in the first line). The third, fourth and fifth columns of Table A1 lists ranges of weight ratios for rates at which the Component (a) compound is typically applied to a field-grown crop relative to Component (b) (i.e. (a):(b)). Thus, for example, the first line of Table A1 specifically discloses the combination of Component (a) (i.e. Compound 2 in Index Table A) with 2,4-D is typically applied in a weight ratio between 1:192-6:1. The remaining lines of Table A1 are to be construed similarly.

TABLE A1

| Component (a)<br>(Compound#) | Component (b) | Typical<br>Weight Ratio | More Typical<br>Weight Ratio | Most Typical<br>Weight Ratio |
|---|---|---|---|---|
| 2 | 2,4-D | 1:192-6:1 | 1:64-2:1 | 1:24-1:3 |
| 2 | Acetochlor | 1:768-2:1 | 1:256-1:2 | 1:96-1:11 |
| 2 | Acifluorfen | 1:96-12:1 | 1:32-4:1 | 1:12-1:2 |
| 2 | Aclonifen | 1:857-2:1 | 1:285-1:3 | 1:107-1:12 |
| 2 | Alachlor | 1:768-2:1 | 1:256-1:2 | 1:96-1:11 |
| 2 | Ametryn | 1:384-3:1 | 1:128-1:1 | 1:48-1:6 |
| 2 | Amicarbazone | 1:192-6:1 | 1:64-2:1 | 1:24-1:3 |
| 2 | Amidosulfuron | 1:6-168:1 | 1:2-56:1 | 1:1-11:1 |
| 2 | Aminocyclopyrachlor | 1:48-24:1 | 1:16-8:1 | 1:6-2:1 |
| 2 | Aminopyralid | 1:20-56:1 | 1:6-19:1 | 1:2-4:1 |
| 2 | Amitrole | 1:768-2:1 | 1:256-1:2 | 1:96-1:11 |
| 2 | Anilofos | 1:96-12:1 | 1:32-4:1 | 1:12-1:2 |
| 2 | Asulam | 1:960-2:1 | 1:320-1:3 | 1:120-1:14 |
| 2 | Atrazine | 1:192-6:1 | 1:64-2:1 | 1:24-1:3 |
| 2 | Azimsulfuron | 1:6-168:1 | 1:2-56:1 | 1:1-11:1 |
| 2 | Beflubutamid | 1:342-4:1 | 1:114-2:1 | 1:42-1:5 |
| 2 | Benfuresate | 1:617-2:1 | 1:205-1:2 | 1:77-1:9 |
| 2 | Bensulfuron-methyl | 1:25-45:1 | 1:8-15:1 | 1:3-3:1 |
| 2 | Bentazone | 1:192-6:1 | 1:64-2:1 | 1:24-1:3 |
| 2 | Benzobicyclon | 1:85-14:1 | 1:28-5:1 | 1:10-1:2 |
| 2 | Benzofenap | 1:257-5:1 | 1:85-2:1 | 1:32-1:4 |
| 2 | Bicyclopyrone | 1:42-27:1 | 1:14-9:1 | 1:5-2:1 |
| 2 | Bifenox | 1:257-5:1 | 1:85-2:1 | 1:32-1:4 |
| 2 | Bispyribac-sodium | 1:10-112:1 | 1:3-38:1 | 1:1-7:1 |
| 2 | Bromacil | 1:384-3:1 | 1:128-1:1 | 1:48-1:6 |
| 2 | Bromobutide | 1:384-3:1 | 1:128-1:1 | 1:48-1:6 |
| 2 | Bromoxynil | 1:96-12:1 | 1:32-4:1 | 1:12-1:2 |
| 2 | Butachlor | 1:768-2:1 | 1:256-1:2 | 1:96-1:11 |
| 2 | Butafenacil | 1:42-27:1 | 1:14-9:1 | 1:5-2:1 |
| 2 | Butylate | 1:1542-1:2 | 1:514-1:5 | 1:192-1:22 |
| 2 | Carfenstrole | 1:192-6:1 | 1:64-2:1 | 1:24-1:3 |
| 2 | Carfentrazone-ethyl | 1:128-9:1 | 1:42-3:1 | 1:16-1:2 |
| 2 | Chlorimuron-ethyl | 1:8-135:1 | 1:2-45:1 | 1:1-9:1 |
| 2 | Chlorotoluron | 1:768-2:1 | 1:256-1:2 | 1:96-1:11 |
| 2 | Chlorsulfuron | 1:6-168:1 | 1:2-56:1 | 1:1-11:1 |
| 2 | Cincosulfuron | 1:17-68:1 | 1:5-23:1 | 1:2-5:1 |
| 2 | Cinidon-ethyl | 1:384-3:1 | 1:128-1:1 | 1:48-1:6 |
| 2 | Cinmethylin | 1:34-34:1 | 1:11-12:1 | 1:4-3:1 |
| 2 | Clacyfos | 1:34-34:1 | 1:11-12:1 | 1:4-3:1 |
| 2 | Clethodim | 1:48-24:1 | 1:16-8:1 | 1:6-2:1 |
| 2 | Clodinafop-propargyl | 1:20-56:1 | 1:6-19:1 | 1:2-4:1 |
| 2 | Clomazone | 1:384-3:1 | 1:128-1:1 | 1:48-1:6 |
| 2 | Clomeprop | 1:171-7:1 | 1:57-3:1 | 1:21-1:3 |
| 2 | Clopyralid | 1:192-6:1 | 1:64-2:1 | 1:24-1:3 |
| 2 | Cloransulam-methyl | 1:12-96:1 | 1:4-32:1 | 1:1-6:1 |

TABLE A1-continued

| Component (a) (Compound#) | Component (b) | Typical Weight Ratio | More Typical Weight Ratio | Most Typical Weight Ratio |
|---|---|---|---|---|
| 2 | Cumyluron | 1:384-3:1 | 1:128-1:1 | 1:48-1:6 |
| 2 | Cyanazine | 1:384-3:1 | 1:128-1:1 | 1:48-1:6 |
| 2 | Cyclopyrimorate | 1:17-68:1 | 1:5-23:1 | 1:2-5:1 |
| 2 | Cyclosulfamuron | 1:17-68:1 | 1:5-23:1 | 1:2-5:1 |
| 2 | Cycloxydim | 1:96-12:1 | 1:32-4:1 | 1:12-1:2 |
| 2 | Cyhalofop | 1:25-45:1 | 1:8-15:1 | 1:3-3:1 |
| 2 | Daimuron | 1:192-6:1 | 1:64-2:1 | 1:24-1:3 |
| 2 | Desmedipham | 1:322-4:1 | 1:107-2:1 | 1:40-1:5 |
| 2 | Dicamba | 1:192-6:1 | 1:64-2:1 | 1:24-1:3 |
| 2 | Dichlobenil | 1:1371-1:2 | 1:457-1:4 | 1:171-1:20 |
| 2 | Dichlorprop | 1:925-2:1 | 1:308-1:3 | 1:115-1:13 |
| 2 | Diclofop-methyl | 1:384-3:1 | 1:128-1:1 | 1:48-1:6 |
| 2 | Diclosulam | 1:10-112:1 | 1:3-38:1 | 1:1-7:1 |
| 2 | Difenzoquat | 1:288-4:1 | 1:96-2:1 | 1:36-1:4 |
| 2 | Diflufenican | 1:857-2:1 | 1:285-1:3 | 1:107-1:12 |
| 2 | Diflufenzopyr | 1:12-96:1 | 1:4-32:1 | 1:1-6:1 |
| 2 | Dimethachlor | 1:768-2:1 | 1:256-1:2 | 1:96-1:11 |
| 2 | Dimethametryn | 1:192-6:1 | 1:64-2:1 | 1:24-1:3 |
| 2 | Dimethenamid-P | 1:384-3:1 | 1:128-1:1 | 1:48-1:6 |
| 2 | Dithiopyr | 1:192-6:1 | 1:64-2:1 | 1:24-1:3 |
| 2 | Diuron | 1:384-3:1 | 1:128-1:1 | 1:48-1:6 |
| 2 | EPTC | 1:768-2:1 | 1:256-1:2 | 1:96-1:11 |
| 2 | Esprocarb | 1:1371-1:2 | 1:457-1:4 | 1:171-1:20 |
| 2 | Ethalfluralin | 1:384-3:1 | 1:128-1:1 | 1:48-1:6 |
| 2 | Ethametsulfuron-methyl | 1:17-68:1 | 1:5-23:1 | 1:2-5:1 |
| 2 | Ethoxyfen | 1:8-135:1 | 1:2-45:1 | 1:1-9:1 |
| 2 | Ethoxysulfuron | 1:20-56:1 | 1:6-19:1 | 1:2-4:1 |
| 2 | Etobenzanid | 1:257-5:1 | 1:85-2:1 | 1:32-1:4 |
| 2 | Fenoxaprop-ethyl | 1:120-10:1 | 1:40-4:1 | 1:15-1:2 |
| 2 | Fenoxasulfone | 1:85-14:1 | 1:28-5:1 | 1:10-1:2 |
| 2 | Fenquinotrione | 1:17-68:1 | 1:5-23:1 | 1:2-5:1 |
| 2 | Fentrazamide | 1:17-68:1 | 1:5-23:1 | 1:2-5:1 |
| 2 | Flazasulfuron | 1:17-68:1 | 1:5-23:1 | 1:2-5:1 |
| 2 | Florasulam | 1:2-420:1 | 1:1-140:1 | 2:1-27:1 |
| 2 | Fluazifop-butyl | 1:192-6:1 | 1:64-2:1 | 1:24-1:3 |
| 2 | Flucarbazone | 1:8-135:1 | 1:2-45:1 | 1:1-9:1 |
| 2 | Flucetosulfuron | 1:8-135:1 | 1:2-45:1 | 1:1-9:1 |
| 2 | Flufenacet | 1:257-5:1 | 1:85-2:1 | 1:32-1:4 |
| 2 | Flumetsulam | 1:24-48:1 | 1:8-16:1 | 1:3-3:1 |
| 2 | Flumiclorac-pentyl | 1:10-112:1 | 1:3-38:1 | 1:1-7:1 |
| 2 | Flumioxazin | 1:25-45:1 | 1:8-15:1 | 1:3-3:1 |
| 2 | Fluometuron | 1:384-3:1 | 1:128-1:1 | 1:48-1:6 |
| 2 | Flupyrsulfuron-methyl | 1:3-336:1 | 1:1-112:1 | 2:1-21:1 |
| 2 | Fluridone | 1:384-3:1 | 1:128-1:1 | 1:48-1:6 |
| 2 | Fluroxypyr | 1:96-12:1 | 1:32-4:1 | 1:12-1:2 |
| 2 | Flurtamone | 1:857-2:1 | 1:285-1:3 | 1:107-1:12 |
| 2 | Fluthiacet-methyl | 1:48-42:1 | 1:16-14:1 | 1:3-3:1 |
| 2 | Fomesafen | 1:96-12:1 | 1:32-4:1 | 1:12-1:2 |
| 2 | Foramsulfuron | 1:13-84:1 | 1:4-28:1 | 1:1-6:1 |
| 2 | Glufosinate | 1:288-4:1 | 1:96-2:1 | 1:36-1:4 |
| 2 | Glyphosate | 1:288-4:1 | 1:96-2:1 | 1:36-1:4 |
| 2 | Halosulfuron-methyl | 1:17-68:1 | 1:5-23:1 | 1:2-5:1 |
| 2 | Halauxifen | 1:20-56:1 | 1:6-19:1 | 1:2-4:1 |
| 2 | Halauxifen methyl | 1:20-56:1 | 1:6-19:1 | 1:2-4:1 |
| 2 | Haloxyfop-methyl | 1:34-34:1 | 1:11-12:1 | 1:4-3:1 |
| 2 | Hexazinone | 1:192-6:1 | 1:64-2:1 | 1:24-1:3 |
| 2 | Imazamox | 1:13-84:1 | 1:4-28:1 | 1:1-6:1 |
| 2 | Imazapic | 1:20-56:1 | 1:6-19:1 | 1:2-4:1 |
| 2 | Imazapyr | 1:85-14:1 | 1:28-5:1 | 1:10-1:2 |
| 2 | Imazaquin | 1:34-34:1 | 1:11-12:1 | 1:4-3:1 |
| 2 | Imazethabenz-methyl | 1:171-7:1 | 1:57-3:1 | 1:21-1:3 |
| 2 | Imazethapyr | 1:24-48:1 | 1:8-16:1 | 1:3-3:1 |
| 2 | Imazosulfuron | 1:27-42:1 | 1:9-14:1 | 1:3-3:1 |
| 2 | Indanofan | 1:342-4:1 | 1:114-2:1 | 1:42-1:5 |
| 2 | Indaziflam | 1:25-45:1 | 1:8-15:1 | 1:3-3:1 |
| 2 | Iodosulfuron-methyl | 1:3-336:1 | 1:1-112:1 | 2:1-21:1 |
| 2 | Ioxynil | 1:192-6:1 | 1:64-2:1 | 1:24-1:3 |
| 2 | Ipfencarbazone | 1:85-14:1 | 1:28-5:1 | 1:10-1:2 |
| 2 | Isoproturon | 1:384-3:1 | 1:128-1:1 | 1:48-1:6 |
| 2 | Isoxaben | 1:288-4:1 | 1:96-2:1 | 1:36-1:4 |
| 2 | Isoxaflutole | 1:60-20:1 | 1:20-7:1 | 1:7-2:1 |
| 2 | Lactofen | 1:42-27:1 | 1:14-9:1 | 1:5-2:1 |
| 2 | Lenacil | 1:384-3:1 | 1:128-1:1 | 1:48-1:6 |
| 2 | Linuron | 1:384-3:1 | 1:128-1:1 | 1:48-1:6 |
| 2 | MCPA | 1:192-6:1 | 1:64-2:1 | 1:24-1:3 |
| 2 | MCPB | 1:288-4:1 | 1:96-2:1 | 1:36-1:4 |
| 2 | Mecoprop | 1:768-2:1 | 1:256-1:2 | 1:96-1:11 |

TABLE A1-continued

| Component (a) (Compound#) | Component (b) | Typical Weight Ratio | More Typical Weight Ratio | Most Typical Weight Ratio |
|---|---|---|---|---|
| 2 | Mefenacet | 1:384-3:1 | 1:128-1:1 | 1:48-1:6 |
| 2 | Mefluidide | 1:192-6:1 | 1:64-2:1 | 1:24-1:3 |
| 2 | Mesosulfuron-methyl | 1:5-224:1 | 1:1-75:1 | 1:1-14:1 |
| 2 | Mesotrione | 1:42-27:1 | 1:14-9:1 | 1:5-2:1 |
| 2 | Metamifop | 1:42-27:1 | 1:14-9:1 | 1:5-2:1 |
| 2 | Metazachlor | 1:384-3:1 | 1:128-1:1 | 1:48-1:6 |
| 2 | Metazosulfuron | 1:25-45:1 | 1:8-15:1 | 1:3-3:1 |
| 2 | Methabenzthiazuron | 1:768-2:1 | 1:256-1:2 | 1:96-1:11 |
| 2 | Metolachlor | 1:768-2:1 | 1:256-1:2 | 1:96-1:11 |
| 2 | Metosulam | 1:8-135:1 | 1:2-45:1 | 1:1-9:1 |
| 2 | Metribuzin | 1:192-6:1 | 1:64-2:1 | 1:24-1:3 |
| 2 | Metsulfuron-methyl | 1:2-560:1 | 1:1-187:1 | 3:1-35:1 |
| 2 | Molinate | 1:1028-2:1 | 1:342-1:3 | 1:128-1:15 |
| 2 | Napropamide | 1:384-3:1 | 1:128-1:1 | 1:48-1:6 |
| 2 | Napropamide-M | 1:192-6:1 | 1:64-2:1 | 1:24-1:3 |
| 2 | Naptalam | 1:192-6:1 | 1:64-2:1 | 1:24-1:3 |
| 2 | Nicosulfuron | 1:12-96:1 | 1:4-32:1 | 1:1-6:1 |
| 2 | Norflurazon | 1:1152-1:1 | 1:384-1:3 | 1:144-1:16 |
| 2 | Orbencarb | 1:1371-1:2 | 1:457-1:4 | 1:171-1:20 |
| 2 | Orthosulfamuron | 1:20-56:1 | 1:6-19:1 | 1:2-4:1 |
| 2 | Oryzalin | 1:514-3:1 | 1:171-1:2 | 1:64-1:8 |
| 2 | Oxadiargyl | 1:384-3:1 | 1:128-1:1 | 1:48-1:6 |
| 2 | Oxadiazon | 1:548-3:1 | 1:182-1:2 | 1:68-1:8 |
| 2 | Oxasulfuron | 1:27-42:1 | 1:9-14:1 | 1:3-3:1 |
| 2 | Oxaziclomefone | 1:42-27:1 | 1:14-9:1 | 1:5-2:1 |
| 2 | Oxyfluorfen | 1:384-3:1 | 1:128-1:1 | 1:48-1:6 |
| 2 | Paraquat | 1:192-6:1 | 1:64-2:1 | 1:24-1:3 |
| 2 | Pendimethalin | 1:384-3:1 | 1:128-1:1 | 1:48-1:6 |
| 2 | Penoxsulam | 1:10-112:1 | 1:3-38:1 | 1:1-7:1 |
| 2 | Penthoxamid | 1:384-3:1 | 1:128-1:1 | 1:48-1:6 |
| 2 | Pentoxazone | 1:102-12:1 | 1:34-4:1 | 1:12-1:2 |
| 2 | Phenmedipham | 1:102-12:1 | 1:34-4:1 | 1:12-1:2 |
| 2 | Picloram | 1:96-12:1 | 1:32-4:1 | 1:12-1:2 |
| 2 | Picolinafen | 1:34-34:1 | 1:11-12:1 | 1:4-3:1 |
| 2 | Pinoxaden | 1:25-45:1 | 1:8-15:1 | 1:3-3:1 |
| 2 | Pretilachlor | 1:192-6:1 | 1:64-2:1 | 1:24-1:3 |
| 2 | Primisulfuron-methyl | 1:8-135:1 | 1:2-45:1 | 1:1-9:1 |
| 2 | Prodiamine | 1:384-3:1 | 1:128-1:1 | 1:48-1:6 |
| 2 | Profoxydim | 1:42-27:1 | 1:14-9:1 | 1:5-2:1 |
| 2 | Prometryn | 1:384-3:1 | 1:128-1:1 | 1:48-1:6 |
| 2 | Propachlor | 1:1152-1:1 | 1:384-1:3 | 1:144-1:16 |
| 2 | Propanil | 1:384-3:1 | 1:128-1:1 | 1:48-1:6 |
| 2 | Propaquizafop | 1:48-24:1 | 1:16-8:1 | 1:6-2:1 |
| 2 | Propoxycarbazone | 1:17-68:1 | 1:5-23:1 | 1:2-5:1 |
| 2 | Propyrisulfuron | 1:17-68:1 | 1:5-23:1 | 1:2-5:1 |
| 2 | Propyzamide | 1:384-3:1 | 1:128-1:1 | 1:48-1:6 |
| 2 | Prosulfocarb | 1:1200-1:2 | 1:400-1:4 | 1:150-1:17 |
| 2 | Prosulfuron | 1:6-168:1 | 1:2-56:1 | 1:1-11:1 |
| 2 | Pyraclonil | 1:42-27:1 | 1:14-9:1 | 1:5-2:1 |
| 2 | Pyraflufen-ethyl | 1:5-224:1 | 1:1-75:1 | 1:1-14:1 |
| 2 | Pyrasulfotole | 1:13-84:1 | 1:4-28:1 | 1:1-6:1 |
| 2 | Pyrazolynate | 1:857-2:1 | 1:285-1:3 | 1:107-1:12 |
| 2 | Pyrazosulfuron-ethyl | 1:10-112:1 | 1:3-38:1 | 1:1-7:1 |
| 2 | Pyrazoxyfen | 1:5-224:1 | 1:1-75:1 | 1:1-14:1 |
| 2 | Pyribenzoxim | 1:10-112:1 | 1:3-38:1 | 1:1-7:1 |
| 2 | Pyributicarb | 1:384-3:1 | 1:128-1:1 | 1:48-1:6 |
| 2 | Pyridate | 1:288-4:1 | 1:96-2:1 | 1:36-1:4 |
| 2 | Pyriftalid | 1:10-112:1 | 1:3-38:1 | 1:1-7:1 |
| 2 | Pyriminobac-methyl | 1:20-56:1 | 1:6-19:1 | 1:2-4:1 |
| 2 | Pyrimisulfan | 1:17-68:1 | 1:5-23:1 | 1:2-5:1 |
| 2 | Pyrithiobac | 1:24-48:1 | 1:8-16:1 | 1:3-3:1 |
| 2 | Pyroxasulfone | 1:85-14:1 | 1:28-5:1 | 1:10-1:2 |
| 2 | Pyroxsulam | 1:5-224:1 | 1:1-75:1 | 1:1-14:1 |
| 2 | Quinclorac | 1:192-6:1 | 1:64-2:1 | 1:24-1:3 |
| 2 | Quizalofop-ethyl | 1:42-27:1 | 1:14-9:1 | 1:5-2:1 |
| 2 | Rimsulfuron | 1:13-84:1 | 1:4-28:1 | 1:1-6:1 |
| 2 | Saflufenacil | 1:25-45:1 | 1:8-15:1 | 1:3-3:1 |
| 2 | Sethoxydim | 1:96-12:1 | 1:32-4:1 | 1:12-1:2 |
| 2 | Simazine | 1:384-3:1 | 1:128-1:1 | 1:48-1:6 |
| 2 | Sulcotrione | 1:120-10:1 | 1:40-4:1 | 1:15-1:2 |
| 2 | Sulfentrazone | 1:147-8:1 | 1:49-3:1 | 1:18-1:3 |
| 2 | Sulfometuron-methyl | 1:34-34:1 | 1:11-12:1 | 1:4-3:1 |
| 2 | Sulfosulfuron | 1:8-135:1 | 1:2-45:1 | 1:1-9:1 |
| 2 | Tebuthiuron | 1:384-3:1 | 1:128-1:1 | 1:48-1:6 |
| 2 | Tefuryltrione | 1:42-27:1 | 1:14-9:1 | 1:5-2:1 |
| 2 | Tembotrione | 1:31-37:1 | 1:10-13:1 | 1:3-3:1 |
| 2 | Tepraloxydim | 1:25-45:1 | 1:8-15:1 | 1:3-3:1 |

TABLE A1-continued

| Component (a) (Compound#) | Component (b) | Typical Weight Ratio | More Typical Weight Ratio | Most Typical Weight Ratio |
|---|---|---|---|---|
| 2 | Terbacil | 1:288-4:1 | 1:96-2:1 | 1:36-1:4 |
| 2 | Terbuthylazine | 1:857-2:1 | 1:285-1:3 | 1:107-1:12 |
| 2 | Terbutryn | 1:192-6:1 | 1:64-2:1 | 1:24-1:3 |
| 2 | Thenylchlor | 1:85-14:1 | 1:28-5:1 | 1:10-1:2 |
| 2 | Thiazopyr | 1:384-3:1 | 1:128-1:1 | 1:48-1:6 |
| 2 | Thiencarbazone | 1:3-336:1 | 1:1-112:1 | 2:1-21:1 |
| 2 | Thifensulfuron-methyl | 1:5-224:1 | 1:1-75:1 | 1:1-14:1 |
| 2 | Tiafenacil | 1:17-68:1 | 1:5-23:1 | 1:2-5:1 |
| 2 | Thiobencarb | 1:768-2:1 | 1:256-1:2 | 1:96-1:11 |
| 2 | Topramzone | 1:6-168:1 | 1:2-56:1 | 1:1-11:1 |
| 2 | Tralkoxydim | 1:68-17:1 | 1:22-6:1 | 1:8-2:1 |
| 2 | Triallate | 1:768-2:1 | 1:256-1:2 | 1:96-1:11 |
| 2 | Triasulfuron | 1:5-224:1 | 1:1-75:1 | 1:1-14:1 |
| 2 | Triaziflam | 1:171-7:1 | 1:57-3:1 | 1:21-1:3 |
| 2 | Tribenuron-methyl | 1:3-336:1 | 1:1-112:1 | 2:1-21:1 |
| 2 | Triclopyr | 1:192-6:1 | 1:64-2:1 | 1:24-1:3 |
| 2 | Trifloxysulfuron | 1:2-420:1 | 1:1-140:1 | 2:1-27:1 |
| 2 | Trifluralin | 1:288-4:1 | 1:96-2:1 | 1:36-1:4 |
| 2 | Triflusulfuron-methyl | 1:17-68:1 | 1:5-23:1 | 1:2-5:1 |
| 2 | Tritosulfuron | 1:13-84:1 | 1:4-28:1 | 1:1-6:1 |

Table A2 is constructed the same as Table A1 above except that entries below the "Component (a)" column heading are replaced with the respective Component (a) Column Entry shown below. Compound 13 in the Component (a) column is identified in Index Table A. Thus, for example, in Table A2 the entries below the "Component (a)" column heading all recite "Compound 13" (i.e. Compound # identified in Index Table A), and the first line below the column headings in Table A2 specifically discloses a mixture of Compound 13 with 2,4-D. Tables A3 through A7 are constructed similarly.

| Table Number | Component (a) Column Entries |
|---|---|
| A2 | Compound 13 |
| A3 | Compound 14 |
| A4 | Compound 15 |
| A5 | Compound 16 |
| A6 | Compound 30 |
| A7 | Compound 31 |
| A8 | Compound 54 |
| A9 | Compound 61 |

Preferred for better control of undesired vegetation (e.g., lower use rate such as from synergism, broader spectrum of weeds controlled, or enhanced crop safety) or for preventing the development of resistant weeds are mixtures of a compound of this invention with a herbicide selected from the group consisting of chlorimuron-ethyl, nicosulfuron, mesotrione, thifensulfuron-methyl, flupyrsulfuron-methyl, tribenuron, pyroxasulfone, pinoxaden, tembotrione, pyroxsulam, metolachlor and S-metolachlor.

The following Tests demonstrate the control efficacy of the compounds of this invention against specific weeds. The weed control afforded by the compounds is not limited, however, to these species. See Index Table A for compound descriptions. The following abbreviations are used in the Index Tables which follow: c is cyclo, c-Pr is cyclopropyl, —CN is cyano, Ph is phenyl, Py means pyridinyl, pyrr means pyrrolidinyl, morph means morpholinyl and thien means thienyl. The abbreviation "Ex." stands for "Example" and is followed by a number indicating in which example the compound is prepared. Mass Spectra are reported as AP+ unless otherwise indicated.

INDEX TABLE A

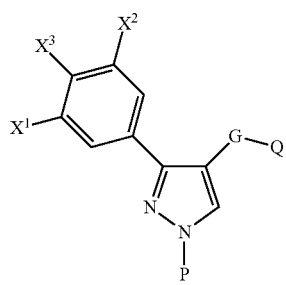

| Cmpd. No. | G | Q | P | $X^1$ | $X^3$ | $X^2$ | m. p. (° C.)/M.S. |
|---|---|---|---|---|---|---|---|
| 1 | C(=O) | Ph | $SO_2CH_2Cl$ | Cl | H | Cl | ** |
| 2 | C(=O) | Ph | $SO_2CF_3$ | Cl | H | Cl | ** |
| 3 | C(=O) | Ph | $SO_2CH_2CF_3$ | Cl | H | Cl | ** |
| 4 | C(=O) | Ph | $C(=O)CH_2Ph$ | Cl | H | Cl | 119-122 |

INDEX TABLE A-continued

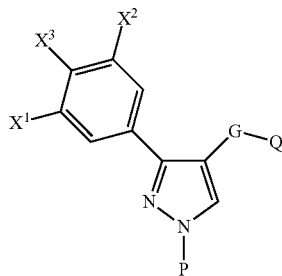

| Cmpd. No. | G | Q | P | X$^1$ | X$^3$ | X$^2$ | m. p. (° C.)/M.S. |
|---|---|---|---|---|---|---|---|
| 5 | C(=NOH) | 3-Py | H | Cl | H | Cl | 333 |
| 6 | C(=O) | 3-Py | CH$_3$ | Cl | H | Cl | 332 |
| 7 | C(=O) | 3-Py | CH$_2$CH$_3$ | Cl | H | Cl | 346 |
| 8 | C(=O) | 3-Py | CH$_2$CH=CH$_2$ | Cl | H | Cl | 358 |
| 9 | C(=O) | 3-Py | CH$_2$C≡CH | Cl | H | Cl | 356 |
| 10 | C(=O) | Ph | CH$_2$CH$_3$ | F | H | Br | ** |
| 11 | C(=O) | Ph | CH$_3$ | Cl | Cl | Cl | 94-101 |
| 12 | C(=O) | Ph | CH$_2$CH$_3$ | Cl | Cl | Cl | 98-114 |
| 13 | C(OCH$_3$)$_2$ | Ph | H | Cl | H | Cl | ** |
| 14 | C(OCH$_2$CH$_3$)$_2$ | Ph | H | Cl | H | Cl | # |
| 15 (Ex. 3) | C(=O) | Ph | CH$_2$OH | Cl | H | Cl | # |
| 16 (Ex. 4) | C(=O) | Ph | C(=O)CH$_2$OCH$_3$ | Cl | H | Cl | 118-123 |
| 17 | C(=O) | 2-Thien | CH$_3$ | Cl | H | Cl | 337 |
| 18 | C(=O) | 2-Thien | CH$_2$CH$_3$ | Cl | H | Cl | 351 |
| 19 | C(=O) | 5-F-3-Py | H | Cl | H | Cl | 334* |
| 20 | C(=O) | 5-F-3-Py | C(=O)CH$_3$ | Cl | H | Cl | 378 |
| 21 | C(=O) | 5-F-3-Py | CH$_2$CH$_3$ | Cl | H | Cl | 364 |
| 22 | C(=O) | 5-F-3-Py | H | F | H | Cl | 320 |
| 23 | C(=O) | 5-F-3-Py | H | F | H | F | 304 |
| 24 | C(=O) | 2-Thien | CH$_2$CH$_3$ | Cl | H | F | 335@ |
| 25 | C(=NN-pyrr) | Ph | CH$_3$ | Cl | Cl | Cl | 139-156 |
| 26 | C(=O) | Ph | C(=O)c-Pr | Cl | H | Cl | 145-147 |
| 27 | C(OCH$_2$CH$_3$)$_2$ | 2-Thien | H | Cl | H | Cl | ** |
| 28 | C(=O) | Ph | CHO | Cl | H | Cl | 95-98 |
| 29 | C(=NOCH$_3$) | Ph | H | Br | H | Br | 63-66 |
| 30 (Ex. 1) | C(=NN-pyrr) | Ph | H | Cl | H | Cl | 66-70 # |
| 31 (Ex. 5) | C(=O) | Ph | CH$_2$CH$_3$ | Cl | H | Cl | 345 # |
| 32 | C(=NOCH$_3$) | 2-Thien | H | Cl | H | Cl | 352 |
| 33 | C(=NNHPh) | Ph | H | Cl | H | Cl | 168-172 |
| 34 | C(=NNHPh) | Ph | CH$_2$CF$_3$ | Cl | H | Cl | 489 |
| 35 | C(=NNH(4-F—Ph)) | Ph | H | Cl | H | Cl | ** |
| 36 | C(=NNHPh) | Ph | CH$_2$CH$_3$ | Cl | H | Cl | 435 |
| 37 | C(=NN-pyrr) | Ph | CH$_2$CH$_3$ | Cl | H | Cl | 413 |
| 38 | C(=O) | Ph | CH$_2$CH$_3$ | Br | H | Br | ** |
| 39 (Ex. 2) | C(=O) | Ph | CH$_2$C≡CH | Cl | H | Cl | # |
| 40 | C(=O) | Ph | CH$_2$CF$_2$H | Cl | H | F | ** |
| 41 | C(=O) | Ph | CH$_2$(c-Pr) | Cl | H | Cl | 371 |
| 42 | C(=NN-pyrr) | Ph | H | Cl | H | F | 62-69 |
| 43 | C(=O) | Ph | CH$_2$CN | Cl | H | Cl | 356@ |
| 44 | C(=O) | Ph | CH(CH$_3$)$_2$ | Cl | H | Cl | 359 |
| 45 | C(=O) | Ph | CH$_2$C(=O)CH$_3$ | Cl | H | Cl | 373 |
| 46 | C(=O) | Ph | CH$_2$CH$_3$ | Cl | H | F | ** |
| 47 | C(=O) | Ph | CH$_3$ | Cl | H | F | ** |
| 48 | C(=O) | Ph | CH$_2$CH$_3$ | F | H | CF3 | ** |
| 49 | C(=NOH) | Ph | H | Br | H | Br | 179-188 |
| 50 | C(=NOH) | Ph | H | Cl | H | Cl | 149-152 |
| 51 | C(=NN-pip) | Ph | H | Cl | H | Cl | 165-175 |
| 52 | C(=NCN) | Ph | H | Cl | H | Cl | 183-186 |
| 53 | C(=O) | Ph | CH$_3$ | Br | H | Br | ** |
| 54 (Ex. 6) | C(=O) | Ph | CH$_3$ | Cl | H | Cl | 331 # |
| 55 | C(=NN-morph) | Ph | H | Cl | H | Cl | ** |
| 56 | C(=NNH(3-Cl—Ph)) | Ph | H | Cl | H | Cl | ** |
| 57 | C(=NNH(2-F—Ph)) | Ph | H | Cl | H | Cl | ** |
| 58 | C(=NNH(3-F—Ph)) | Ph | H | Cl | H | Cl | ** |
| 59 | C(=O) | Ph | CH$_2$CF$_2$H | Cl | H | Cl | 381 |
| 60 | C(=O) | Ph | CH$_2$CH=CH$_2$ | Cl | H | Cl | 357 |

INDEX TABLE A-continued

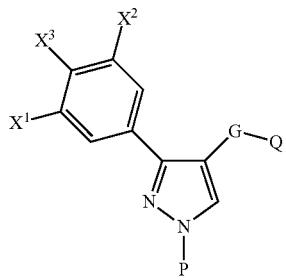

| Cmpd. No. | G | Q | P | $X^1$ | $X^3$ | $X^2$ | m. p. (° C.)/M.S. |
|---|---|---|---|---|---|---|---|
| 61 (Ex. 7) | C(=O) | Ph | CH$_2$CH$_2$CH$_3$ | Cl | H | Cl | 359 |
| 62 | C(1,3-dithiolan-2-yl) | Ph | H | Br | H | Br | ** |
| 63 | C(1,3-dithian-2-yl) | Ph | H | Cl | H | Cl | 408 ** |
| 64 | C(=NOCH$_3$) | Ph | H | Cl | H | Cl | |
| 65 | C(=NNH(4-Cl—Ph))) | Ph | H | Cl | H | Cl | ** |
| 66 | C(=NNH(2-Cl—Ph)) | Ph | H | Cl | H | Cl | ** |
| 67 | C(=NH) | Ph | H | F | H | Fl | ** |
| 68 | C(=NH) | Ph | H | Cl | H | Cl | ** |
| 69 | C(1,3-dithiolan-2-y1) | Ph | H | Cl | H | Cl | ** |

*AP$^-$
@ESI$^+$
** See Index Table B for $^1$H NMR data.
See Synthesis Example for $^1$H NMR data.

INDEX TABLE B

| Cmpd. No. | $^1$H NMR Data (CDCl$_3$ solution in ppm)$^a$ |
|---|---|
| 1 | δ 8.40 (s, 1H), 7.78-7.89 (m, 2H), 7.61-7.70 (m, 3H), 7.48-7.55 (m, 2H), 7.41 (m, 1H), 5.06 (s, 2H). |
| 2 | δ 8.35-8.40 (m, 1H), 7.83 (m, 2H), 7.66 (s, 1H), 7.62 (d, 2H), 7.52 (m, 2H), 7.42 (m, 1H) |
| 3 | δ 8.37 (s, 1H), 7.76-7.86 (m, 2H), 7.60-7.68 (m, 3H), 7.47-7.55 (m, 2H), 7.40 (m, 1H), 4.42-4.52 (m, 2H). |
| 10 | δ 7.77 (m, 3H), 7.67 (t, 1H), 7.54 (tt, 1H), 7.42 (m, 3H), 7.18 (m, 1H), 4.25 (q, 2H), 1.57 (t, 3H). |
| 13 | δ 11.3 (vbs, 1H), 7.94 (s, 1H), 7.36 (bd, 2H), 7.24 (d, 2H), 7.21-7.13 (m, 4H), 3.07 (s, 6H). |
| 14 | δ 12.5 (bs, 1H), 7.87 (s, 1H), 7.39 (bd, 2H), 7.33 (bs, 2H), 7.2-7.1 (m, 4H), 3.38-3.29 (m, 2H), 3.29-3.20 (m, 2H), 1.14 (t, 6H). |
| 27 | δ 11.3 (bs, 1H), 7.90 (s, 1H), 7.45 (d, 2H), 7.20 (t, 1H), 7.14 (dd, 1H), 6.91 (dd, 1H), 6.82 (dd, 1H), 3.40-3.30 (m, 4H), 1.14 (t, 6H). |
| 35 | δ 10.55 (bs, 1H), 7.72 (s, 1H), 7.61 (dd, 2H), 7.53 (m, 2H), 7.49 (m, 1H), 7.31 (m, 3H), 7.22 (s, 1H), 7.02 (m, 2H), 6.96 (m, 2H). |
| 38 | δ 7.80 (d, 2H), 7.78 (s, 1H), 7.75 (dd, 2H), 7.59 (t, 1H), 7.54 (s, 1H), 7.42 (m, 2H), 4.24 (q, 2H), 1.57 (t, 3H). |
| 40 | δ 7.84 (s, 1H), 7.78 (dd, 2H), 7.57 (m, 1H), 7.53 (m, 1H), 7.44 (m, 2H), 7.37 (m, 1H), 7.06 (dt, 1H), 6.21 (m, 1H), 4.53 (td, 2H). |
| 46 | δ 7.77 (m, 3H), 7.53 (m, 2H), 7.43 (m, 2H), 7.37 (m, 1H), 7.03 (dt, 1H), 4.25 (q, 2H), 1.57 (t, 3H). |
| 47 | δ 7.76 (m, 3H), 7.53 (d, 2H), 7.43 (d, 2H), 7.37 (m, 1H), 7.03 (d, 1H), 3.99 (s, 3H). |
| 48 | δ 7.80 (m, 2H), 7.76 (m, 2H), 7.69 (m, 1H), 7.53 (m, 1H), 7.42 (m, 2H), 7.24 (m, 1H), 4.25 (q, 2H), 1.59 (t, 3H). |
| 53 | δ 7.82 (d, 2H), 7.73 (m, 3H), 7.58 (s, 1H), 7.52 (m, 1H), 7.39 (m, 2H), 3.95 (s, 3H). |
| 55 | δ 10.32 (m, 1H), 7.70 (m, 1H), 7.58 (m, 2H), 7.48 (m, 2H), 7.35-7.25 (m, 4H), 3.45 (m, 4H), 2.77 (m, 4H). |
| 56 | δ 7.72 (s, 1H), 7.63 (m, 2H), 7.58 (m, 1H), 7.51 (d, 2H), 7.32 (m, 3H), 7.21 (s, 1H), 7.16 (s, 1H), 7.14 (s, 1H), 6.84 (m, 2H). |
| 57 | δ 7.76 (s, 1H), 7.71 (m, 2H), 7.64 (dd, 2H), 7.50 (d, 2H), 7.32 (m, 3H), 7.21 (t, 1H), 7.12 (m, 1H), 6.95 (m, 1H), 6.79 (m, 1H). |
| 58 | δ 7.73 (s, 1H), 7.61 (d, 3H), 7.51 (d, 2H), 7.32 (m, 4H), 7.21 (s, 1H), 7.15 (m, 1H), 6.94 (m, 1H), 6.69 (m, 1H), 6.55 (dd, 1H). |
| 62 | δ 9.0-10.2 (m, 1H), 7.84-7.88 (m, 1H), 7.50-7.56 (m, 2H), 7.46-7.49 (m, 1H), 7.15-7.27 (m, 5H), 3.35-3.47 (m, 4H). |
| 63 | δ 7.62-7.69 (m, 3H), 7.17-7.32 (m, 4H), 7.04-7.11 (m, 1H), 2.66-2.80 (m, 4H), 1.92-2.00 (m, 2H). |
| 65 | δ ppm 7.72 (s, 1H), 7.61 (d, 2H), 7.51 (m, 2H), 7.31 (m, 3H), 7.20 (m, 3H), 7.00 (m, 2H) |
| 66 | δ 8.09 (bs, 1H), 7.77 (s, 1H), 7.66 (d, 2H), 7.50 (d, 2H), 7.33 (m, 3H), 7.24 (m, 1H), 7.21 (m, 1H), 7.17 (m, 2H), 6.78 (m, 1H). |
| 67 | δ 7.73 (s, 1H), 7.58 (m, 2H), 7.41 (m, 1H), 7.34 (m, 2H), 7.03 (m, 2H), 6.67 (t, 1H). |

INDEX TABLE B-continued

| Cmpd. No. | ¹H NMR Data (CDCl₃ solution in ppm)ᵃ |
|---|---|
| 68 | δ 7.93 (s, 1H), 7.52 (m, 2H), 7.42 (s, 1H), 7.33 (d, 2H), 7.28 (d, 2H), 7.17 (t, 1H). |
| 69 | δ 11.0-12.8 (m, 1H), 7.82-7.85 (m, 1H), 7.50-7.56 (m, 2H), 7.15-7.28 (m, 4H), 6.99-7.03 (m, 2H), 3.35-3.48 (m, 4H). |

ᵃdata are in ppm downfield from tetramethylsilane 500 MHz unless indicated otherwise. Couplings are designated by (s)-singlet, (vbs)-very broad singlet, (d)-doublet, (bd) broad doublet, (t)-triplet, , (td)-triplet of doublets, (tt)-triplet of triplets, (m)-multiplet, (dd)-doublet of doublets, (dt)-doublet of triplets and (bs)-broad singlet.

Biological Examples of the Invention

Test A

Seeds of plant species selected from barnyardgrass (*Echinochloa crus-galli*), large (Lg) crabgrass (*Digitaria sanguinalis*), giant foxtail (*Setaria faberii*), morningglory (*Ipomoea* spp.), pigweed (*Amaranthus retroflexus*), velvetleaf (*Abutilon theophrasti*), wheat (*Triticum aestivum*), and corn (*Zea mays*) were planted into a blend of loam soil and sand and treated preemergence with a directed soil spray using test chemicals formulated in a non-phytotoxic solvent mixture which included a surfactant. At the same time these species were also treated with postemergence applications of test chemicals formulated in the same manner. Plants ranged in height from 2 to 10 cm and were in the one- to two-leaf stage for the postemergence treatment. Treated plants and untreated controls were maintained in a greenhouse for approximately 10 days, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

| 1000 g ai/ha | Compounds | | | | | | | | | | | | | |
|---|---|---|---|---|---|---|---|---|---|---|---|---|---|---|
| | 10 | 11 | 12 | 19 | 20 | 21 | 25 | 29 | 30 | 31 | 33 | 35 | 38 | 39 |
| Postemergence | | | | | | | | | | | | | | |
| Barnyardgrass | 0 | 0 | 0 | 0 | 0 | 0 | 0 | 0 | 0 | 20 | 0 | 0 | 0 | 0 |
| Corn | 0 | 0 | 0 | 0 | 0 | 0 | 0 | 0 | 0 | 10 | 0 | 0 | 0 | 0 |
| Crabgrass, Large | 0 | 0 | 0 | 0 | 0 | 10 | 0 | 0 | 0 | 0 | 0 | 0 | 0 | 0 |
| Foxtail, Giant | 0 | 0 | 0 | 0 | 0 | 0 | 0 | 10 | 0 | 0 | 0 | 0 | 0 | 0 |
| Morningglory | 0 | 0 | 0 | 0 | 0 | 0 | 0 | 0 | 0 | 0 | 0 | 0 | — | — |
| Pigweed | 90 | 90 | 90 | 100 | 90 | 100 | 90 | 90 | 100 | 100 | 100 | 90 | 100 | 100 |
| Velvetleaf | 90 | 80 | 80 | 100 | 90 | 90 | 80 | 90 | 100 | 90 | 100 | 90 | 90 | 100 |
| Wheat | 0 | 0 | 0 | 0 | 0 | 0 | 0 | 0 | 0 | 0 | 0 | 0 | 0 | 0 |

| 1000 g ai/ha | Compounds | | | | | | | | | | | | | |
|---|---|---|---|---|---|---|---|---|---|---|---|---|---|---|
| | 40 | 42 | 46 | 47 | 48 | 49 | 50 | 51 | 52 | 53 | 55 | 56 | 57 | 58 |
| Postemergence | | | | | | | | | | | | | | |
| Barnyardgrass | 0 | 0 | 0 | 0 | 20 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 |
| Crabgrass, Large | 0 | 0 | 0 | 0 | 20 | 0 | 0 | 0 | 0 | 0 | 0 | 0 | 0 | 0 |
| Foxtail, Giant | 0 | 0 | 0 | 0 | 20 | 0 | 10 | 0 | 0 | 0 | 0 | 0 | 0 | 0 |
| Morningglory | 0 | 0 | — | — | 20 | 0 | 0 | 0 | 0 | 0 | 0 | 0 | 0 | 0 |
| Pigweed | 40 | 100 | 90 | 90 | 90 | 90 | 90 | 90 | 90 | 100 | 100 | 90 | 90 | 90 |
| Velvetleaf | 0 | 100 | 90 | 90 | 90 | 80 | 100 | 90 | 100 | 90 | 100 | 90 | 100 | 90 |
| Wheat | 0 | 0 | 0 | 0 | 0 | 0 | 0 | 0 | 0 | 0 | 0 | 0 | 0 | 0 |

| 1000 g ai/ha | Compounds | | | | | |
|---|---|---|---|---|---|---|
| | 62 | 64 | 65 | 66 | 67 | 68 |
| Postemergence | | | | | | |
| Barnyardgrass | 0 | 0 | 0 | 0 | 0 | 0 |
| Corn | 0 | 0 | 0 | 0 | 0 | 0 |
| Crabgrass, Large | 0 | 0 | 0 | 0 | 0 | 0 |
| Foxtail, Giant | 0 | 0 | 0 | 0 | 0 | 0 |
| Morningglory | — | 0 | 30 | 0 | 0 | 0 |
| Pigweed | 100 | 80 | 90 | 80 | 80 | 100 |
| Velvetleaf | 90 | 80 | 90 | 90 | 90 | 90 |
| Wheat | 0 | 0 | 0 | 0 | 0 | 0 |

TABLE A-continued

| 500 g ai/ha | Compounds | | | | | | | | | | | | | |
|---|---|---|---|---|---|---|---|---|---|---|---|---|---|---|
| | 1 | 2 | 3 | 4 | 5 | 6 | 7 | 8 | 9 | 13 | 14 | 15 | 16 | 22 |
| Postemergence | | | | | | | | | | | | | | |
| Barnyardgrass | 0 | 0 | 0 | 0 | 0 | 0 | 0 | 0 | 10 | 0 | 0 | 0 | 0 | 0 |
| Corn | 0 | 0 | 0 | 0 | — | 0 | 0 | 0 | — | 0 | 0 | 0 | 0 | 0 |
| Crabgrass, Large | 0 | 0 | 0 | 0 | 0 | 0 | 0 | 0 | 0 | 0 | 0 | 0 | 0 | 0 |
| Foxtail, Giant | 0 | 0 | 0 | 10 | 0 | 0 | 0 | 0 | 0 | 0 | 0 | 0 | 0 | 0 |
| Morningglory | 0 | 0 | 0 | 0 | 0 | 0 | 0 | 0 | 0 | 0 | 0 | 0 | 0 | 0 |
| Pigweed | 90 | 100 | 100 | 80 | 0 | 30 | 70 | 60 | 80 | 100 | 90 | 90 | 100 | 100 |
| Velvetleaf | 90 | 100 | 100 | 90 | 0 | 10 | 70 | 30 | 60 | 90 | 90 | 90 | 90 | 80 |
| Wheat | 0 | 0 | 0 | 0 | 0 | 0 | 0 | 0 | 0 | 0 | 0 | 0 | 0 | 0 |

| 500 g ai/ha | Compounds | | | | | | | | | | | | | |
|---|---|---|---|---|---|---|---|---|---|---|---|---|---|---|
| | 23 | 24 | 26 | 27 | 28 | 32 | 34 | 36 | 37 | 41 | 43 | 44 | 45 | 54 |
| Postemergence | | | | | | | | | | | | | | |
| Barnyardgrass | 0 | 10 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 |
| Crabgrass, Large | 0 | 20 | 0 | 0 | 0 | 0 | 0 | 0 | 0 | 0 | 0 | 0 | 0 | 0 |
| Foxtail, Giant | 0 | 10 | 0 | 0 | 0 | 0 | 0 | 0 | 0 | 0 | 0 | 0 | 0 | 0 |
| Morningglory | 0 | 10 | 0 | 0 | 0 | 0 | 0 | 0 | 0 | — | — | — | 0 | 0 |
| Pigweed | 60 | 100 | 80 | 100 | 90 | 60 | 20 | 80 | 100 | 60 | 80 | 100 | 60 | 100 |
| Velvetleaf | 40 | 90 | 80 | 90 | 90 | 70 | 30 | 90 | 100 | 80 | 80 | 90 | 80 | 100 |
| Wheat | 0 | 0 | 0 | 0 | 0 | 0 | 0 | 0 | 0 | 0 | 0 | 0 | 0 | 0 |

| 500 g ai/ha | Compounds | | | | |
|---|---|---|---|---|---|
| | 59 | 60 | 61 | 63 | 69 |
| Postemergence | | | | | |
| Barnyardgrass | 0 | 0 | 0 | 0 | 0 |
| Corn | 0 | 0 | 0 | 0 | 0 |
| Crabgrass, Large | 0 | 0 | 0 | 0 | 0 |
| Foxtail, Giant | 0 | 0 | 0 | 0 | 0 |
| Morningglory | 0 | 0 | 0 | 0 | 0 |
| Pigweed | 80 | 90 | 90 | 80 | 80 |
| Velvetleaf | 70 | 90 | 90 | 60 | 80 |
| Wheat | 0 | 0 | 0 | 0 | 0 |

| 125 g ai/ha | Compounds | | | | | | | | | | | | | |
|---|---|---|---|---|---|---|---|---|---|---|---|---|---|---|
| | 1 | 2 | 3 | 4 | 5 | 6 | 7 | 8 | 9 | 13 | 14 | 15 | 16 | 22 |
| Postemergence | | | | | | | | | | | | | | |
| Barnyardgrass | 0 | 0 | 0 | 0 | 0 | 0 | 0 | 0 | 0 | 0 | 0 | 0 | 0 | 0 |
| Corn | 0 | 0 | 0 | 0 | — | 0 | 0 | 0 | — | 0 | 0 | 0 | 0 | 0 |
| Crabgrass, Large | 0 | 0 | 0 | 0 | 0 | 0 | 0 | 0 | 0 | 0 | 0 | 0 | 0 | 0 |
| Foxtail, Giant | 0 | 0 | 0 | 0 | 0 | 0 | 0 | 0 | 0 | 0 | 0 | 0 | 0 | 0 |
| Morningglory | 0 | 0 | 0 | 0 | 0 | 0 | 0 | 0 | 0 | 0 | 0 | 0 | 0 | 0 |
| Pigweed | 80 | 90 | 80 | 70 | 0 | 0 | 40 | 30 | 60 | 90 | 80 | 80 | 80 | 70 |
| Velvetleaf | 90 | 90 | 90 | 80 | 0 | 10 | 50 | 10 | 50 | 80 | 80 | 80 | 80 | 60 |
| Wheat | 0 | 0 | 0 | 0 | 0 | 0 | 0 | 0 | 0 | 0 | 0 | 0 | 0 | 0 |

| 125 g ai/ha | Compounds | | | | | | | | | | | | | |
|---|---|---|---|---|---|---|---|---|---|---|---|---|---|---|
| | 23 | 24 | 26 | 27 | 28 | 32 | 34 | 36 | 37 | 41 | 43 | 44 | 45 | 54 |
| Postemergence | | | | | | | | | | | | | | |
| Barnyardgrass | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 |
| Crabgrass, Large | 0 | 10 | 0 | 0 | 0 | 0 | 0 | 0 | 0 | 0 | 0 | 0 | 0 | 0 |
| Foxtail, Giant | 0 | 0 | 0 | 0 | 0 | 0 | 0 | 0 | 0 | 0 | 0 | 0 | 0 | 0 |
| Morningglory | 0 | 0 | 0 | 0 | 0 | 0 | 0 | 0 | 0 | — | — | — | — | 0 |
| Pigweed | 50 | 80 | 40 | 80 | 80 | 0 | 0 | 30 | 80 | 30 | 50 | 80 | 40 | 90 |
| Velvetleaf | 0 | 40 | 50 | 80 | 80 | 60 | 10 | 70 | 80 | 40 | 20 | 90 | 60 | 90 |
| Wheat | 0 | 0 | 0 | 0 | 0 | 0 | 0 | 0 | 0 | 0 | 0 | 0 | 0 | 0 |

TABLE A-continued

| Compounds | | | | | |
|---|---|---|---|---|---|
| 125 g ai/ha | 59 | 60 | 61 | 63 | 69 |
| Postemergence | | | | | |
| Barnyardgrass | 0 | 0 | 0 | 0 | 0 |
| Corn | 0 | 0 | 0 | 0 | 0 |
| Crabgrass, Large | 0 | 0 | 0 | 0 | 0 |
| Foxtail, Giant | 0 | 0 | 0 | 0 | 0 |
| Morningglory | 0 | 0 | 0 | 0 | 0 |
| Pigweed | 60 | 80 | 80 | 20 | 30 |
| Velvetleaf | 50 | 90 | 80 | 10 | 20 |
| Wheat | 0 | 0 | 0 | 0 | 0 |

| Compounds | | | | | | | | | | | | | | |
|---|---|---|---|---|---|---|---|---|---|---|---|---|---|---|
| 1000 g ai/ha | 10 | 11 | 12 | 19 | 20 | 21 | 25 | 29 | 30 | 31 | 33 | 35 | 38 | 39 |
| Preemergence | | | | | | | | | | | | | | |
| Barnyardgrass | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 |
| Crabgrass, Large | 0 | 0 | 0 | 0 | 0 | 0 | 0 | 0 | 0 | 0 | 0 | 0 | 0 | 0 |
| Foxtail, Giant | 0 | 0 | 0 | 0 | 0 | 0 | 0 | 0 | 0 | 0 | 0 | 0 | 0 | 0 |
| Morningglory | 0 | 0 | 0 | 0 | 0 | 0 | 0 | 0 | 0 | 0 | 0 | 0 | 0 | 0 |
| Pigweed | 100 | 90 | 80 | 100 | 100 | 80 | 90 | 40 | 90 | 100 | 100 | 100 | 90 | 100 |
| Velvetleaf | 90 | 70 | 70 | 90 | 80 | 80 | 20 | 70 | 0 | 70 | 80 | 100 | 80 | 100 |
| Wheat | 0 | 0 | 0 | 0 | 0 | 0 | 0 | 0 | 0 | 0 | 0 | 0 | 0 | 0 |

| Compounds | | | | | | | | | | | | | | |
|---|---|---|---|---|---|---|---|---|---|---|---|---|---|---|
| 1000 g ai/ha | 40 | 42 | 46 | 47 | 48 | 49 | 50 | 51 | 52 | 53 | 55 | 56 | 57 | 58 |
| Preemergence | | | | | | | | | | | | | | |
| Barnyardgrass | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 |
| Crabgrass, Large | 0 | 0 | 0 | 0 | 0 | 0 | 0 | 0 | 0 | 0 | 0 | 0 | 0 | 0 |
| Foxtail, Giant | 0 | 0 | 0 | 0 | 0 | 10 | 0 | 0 | 0 | 0 | 0 | 0 | 0 | 0 |
| Morningglory | 0 | 0 | — | — | 0 | 0 | 0 | 0 | 0 | 0 | 0 | 0 | 0 | 0 |
| Pigweed | 0 | 100 | 100 | 80 | 100 | 80 | 100 | 100 | 50 | 90 | 90 | 100 | 90 | 100 |
| Velvetleaf | 0 | 100 | 90 | 90 | 80 | 0 | 90 | 90 | 60 | 60 | 80 | 90 | 80 | 90 |
| Wheat | 0 | 0 | 0 | 0 | 0 | 0 | 0 | 0 | 0 | 0 | 0 | 0 | 0 | 0 |

| Compounds | | | | | | |
|---|---|---|---|---|---|---|
| 1000 g ai/ha | 62 | 64 | 65 | 66 | 67 | 68 |
| Preemergence | | | | | | |
| Barnyardgrass | 0 | 0 | 0 | 0 | 0 | 0 |
| Corn | 0 | 0 | 0 | 0 | 0 | 0 |
| Crabgrass, Large | 0 | 0 | 0 | 0 | 0 | 0 |
| Foxtail, Giant | 0 | 0 | 0 | 0 | 0 | 0 |
| Morningglory | — | 0 | 0 | 0 | 0 | 0 |
| Pigweed | 80 | 0 | 80 | 80 | 100 | 100 |
| Velvetleaf | 60 | 0 | 80 | 80 | 100 | 100 |
| Wheat | 0 | 0 | 0 | 0 | 0 | 0 |

| Compounds | | | | | | | | | | | | | |
|---|---|---|---|---|---|---|---|---|---|---|---|---|---|
| 500 g ai/ha | 1 | 2 | 3 | 4 | 5 | 6 | 7 | 8 | 9 | 13 | 14 | 15 | 16 | 22 |
| Preemergence | | | | | | | | | | | | | | |
| Barnyardgrass | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 |
| Crabgrass, Large | 0 | 0 | 0 | 20 | 0 | 0 | 0 | 0 | 10 | 0 | 0 | 0 | 0 | 0 |
| Foxtail, Giant | 0 | 0 | 0 | 30 | 0 | 0 | 0 | 0 | 20 | 0 | 0 | 0 | 0 | 0 |
| Morningglory | 0 | 0 | 0 | 0 | 0 | 0 | 0 | 0 | 0 | 0 | 0 | 0 | 0 | 0 |
| Pigweed | 80 | 100 | 80 | 90 | 20 | 20 | 60 | 50 | 90 | 100 | 100 | 100 | 100 | 100 |
| Velvetleaf | 20 | 100 | 50 | 90 | 0 | 20 | 50 | 0 | 80 | 70 | 100 | 90 | 80 | 60 |
| Wheat | 0 | 0 | 0 | 0 | 0 | 0 | 0 | 0 | 0 | 0 | 0 | 0 | 0 | 0 |

TABLE A-continued

| 500 g ai/ha | Compounds | | | | | | | | | | | | | |
|---|---|---|---|---|---|---|---|---|---|---|---|---|---|---|
| | 23 | 24 | 26 | 27 | 28 | 32 | 34 | 36 | 37 | 41 | 43 | 44 | 45 | 54 |
| Preemergence | | | | | | | | | | | | | | |
| Barnyardgrass | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 |
| Crabgrass, Large | 0 | 20 | 0 | 0 | 0 | 0 | 0 | 0 | 0 | 0 | 0 | 0 | 0 | 0 |
| Foxtail, Giant | 0 | 0 | 0 | 0 | 0 | 0 | 0 | 0 | 0 | 0 | 0 | 0 | 0 | 0 |
| Morningglory | 0 | 0 | 0 | 0 | 0 | 0 | 0 | 0 | 0 | 0 | 0 | 0 | 0 | 0 |
| Pigweed | 100 | 80 | 0 | 100 | 90 | — | 0 | 70 | 90 | 60 | 40 | 70 | 70 | 90 |
| Velvetleaf | 90 | 0 | 0 | 80 | 60 | 0 | 0 | 20 | 40 | 60 | 30 | 40 | 30 | 60 |
| Wheat | 0 | 0 | 0 | 0 | 0 | 0 | 0 | 0 | 0 | 0 | 0 | 0 | 0 | 0 |

| 500 g ai/ha | Compounds | | | | |
|---|---|---|---|---|---|
| | 59 | 60 | 61 | 63 | 69 |
| Preemergence | | | | | |
| Barnyardgrass | 0 | 0 | 0 | 0 | 0 |
| Corn | 0 | 0 | 0 | 0 | 0 |
| Crabgrass, Large | 0 | 0 | 0 | 0 | 0 |
| Foxtail, Giant | 0 | 0 | 0 | 0 | 0 |
| Morningglory | 0 | 0 | 0 | 0 | 0 |
| Pigweed | 30 | 90 | 90 | 60 | 40 |
| Velvetleaf | 40 | 40 | 40 | 0 | 20 |
| Wheat | 0 | 0 | 0 | 0 | 0 |

| 125 g ai/ha | Compounds | | | | | | | | | | | | | |
|---|---|---|---|---|---|---|---|---|---|---|---|---|---|---|
| | 1 | 2 | 3 | 4 | 5 | 6 | 7 | 8 | 9 | 13 | 14 | 15 | 16 | 22 |
| Preemergence | | | | | | | | | | | | | | |
| Barnyardgrass | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 |
| Crabgrass, Large | 0 | 0 | 0 | 0 | 0 | 0 | 0 | 0 | 0 | 0 | 0 | 0 | 0 | 0 |
| Foxtail, Giant | 0 | 0 | 0 | 0 | 0 | 0 | 0 | 0 | 0 | 0 | 0 | 0 | 0 | 0 |
| Morningglory | 0 | 0 | 0 | 0 | 0 | 0 | 0 | 0 | 0 | 0 | 0 | 0 | 0 | 0 |
| Pigweed | 40 | 50 | 60 | 80 | 0 | 0 | 20 | 0 | 60 | 70 | 70 | 20 | 60 | 60 |
| Velvetleaf | 20 | 20 | 0 | 70 | 0 | 0 | 0 | 0 | 0 | — | 50 | 40 | 20 | 30 |
| Wheat | 0 | 0 | 0 | 0 | 0 | 0 | 0 | 0 | 0 | 0 | 0 | 0 | 0 | 0 |

| 125 g ai/ha | Compounds | | | | | | | | | | | | | |
|---|---|---|---|---|---|---|---|---|---|---|---|---|---|---|
| | 23 | 24 | 26 | 27 | 28 | 32 | 34 | 36 | 37 | 41 | 43 | 44 | 45 | 54 |
| Preemergence | | | | | | | | | | | | | | |
| Barnyardgrass | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 |
| Crabgrass, Large | — | 0 | 0 | 0 | 0 | 0 | 0 | 0 | 0 | 0 | 0 | 0 | 0 | 0 |
| Foxtail, Giant | 0 | 0 | 0 | 0 | 0 | 0 | 0 | 0 | 0 | 0 | 0 | 0 | 0 | 0 |
| Morningglory | 0 | 0 | 0 | 0 | 0 | 0 | 0 | 0 | 0 | 0 | 0 | 0 | 0 | 0 |
| Pigweed | 70 | 60 | 0 | 100 | 80 | 0 | 0 | 0 | 40 | 0 | 0 | 0 | 0 | 50 |
| Velvetleaf | 60 | 0 | 0 | 80 | 20 | 0 | 0 | 20 | 0 | 0 | 30 | 20 | 20 | 30 |
| Wheat | 0 | 0 | 0 | 0 | 0 | 0 | 0 | 0 | 0 | 0 | 0 | 0 | 0 | 0 |

| 125 g ai/ha | Compounds | | | | |
|---|---|---|---|---|---|
| | 59 | 60 | 61 | 63 | 69 |
| Preemergence | | | | | |
| Barnyardgrass | 0 | 0 | 0 | 0 | 0 |
| Corn | 0 | 0 | 0 | 0 | 0 |
| Crabgrass, Large | 0 | 0 | 0 | 0 | 0 |
| Foxtail, Giant | 0 | 0 | 0 | 0 | 0 |
| Morningglory | 0 | 0 | 0 | 0 | 0 |
| Pigweed | 0 | 60 | 0 | 0 | 0 |
| Velvetleaf | 0 | 30 | 0 | 0 | 0 |
| Wheat | 0 | 0 | 0 | 0 | 0 |

Test B

Plant species in the flooded paddy test selected from rice (*Oryza sativa*), sedge, umbrella (small-flower umbrella sedge, *Cyperus difformis*), ducksalad (*Heteranthera limosa*), and barnyardgrass (*Echinochloa crus-galli*) were grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 days, after which time all species were compared to controls and visually evaluated. Plant response ratings, summarized in Table B, are based on a scale of 0 to 100 where 0 is no effect and 100 is complete control. A dash (-) response means no test result.

TABLE B

| 250 g ai/ha | Compounds | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Flood | | | | | | | | | | | | | | |
| Barnyardgrass | 0 | 0 | 0 | 0 | 0 | 0 | 0 | 0 | 0 | 0 | — | — | 0 | 0 |
| Ducksalad | 0 | 0 | 0 | 0 | 0 | 0 | 0 | 0 | 0 | 0 | 0 | 20 | 0 | 0 |
| Rice | 0 | 0 | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 70 | 0 | 0 |

| 250 g ai/ha | Compounds | | | | | | | | | | | | | |
|---|---|---|---|---|---|---|---|---|---|---|---|---|---|---|
| | 15 | 16 | 22 | 23 | 24 | 25 | 26 | 27 | 28 | 35 | 38 | 39 | 41 | 42 |
| Flood | | | | | | | | | | | | | | |
| Barnyardgrass | 0 | 0 | 0 | 0 | 0 | — | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 |
| Sedge, Umbrella | 0 | 0 | 0 | 0 | 0 | 70 | 0 | 0 | 0 | 0 | 0 | 0 | 30 | 0 |

| 250 g ai/ha | Compounds | | | | | | | | | | | | | |
|---|---|---|---|---|---|---|---|---|---|---|---|---|---|---|
| | 43 | 44 | 45 | 46 | 47 | 48 | 53 | 55 | 56 | 57 | 58 | 65 | 66 | 67 |
| Flood | | | | | | | | | | | | | | |
| Barnyardgrass | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 |
| Sedge, Umbrella | 0 | 0 | 0 | 0 | 0 | 0 | 40 | 0 | 0 | 75 | 0 | 0 | 70 | 0 |

Test C

Seeds of plant species selected from blackgrass (*Alopecurus myosuroides*), Italian ryegrass (*Lolium multiflorum*), winter wheat (*Triticum aestivum*), galium (catchweed bedstraw, *Galium aparine*), corn (*Zea mays*), large (Lg) crabgrass (*Digitaria sanguinalis*), giant foxtail (*Setaria faberii*), johnsongrass (*Sorghum halepense*), lambsquarters (*Chenopodium album*), morningglory (*Ipomoea coccinea*), yellow nutsedge (*Cyperus esculentus*), pigweed (*Amaranthus retroflexus*), ragweed (common ragweed, *Ambrosia elatior*), soybean (*Glycine max*), barnyardgrass (*Echinochloa crus-galli*), oilseed rape (*Brassica napus*), waterhemp (common waterhemp, *Amaranthus rudis*), and velvetleaf (*Abutilon theophrasti*) were planted into a blend of loam soil and sand and treated preemergence with test chemicals formulated in a non-phytotoxic solvent mixture which included a surfactant.

At the same time, plants selected from these crop and weed species and also winter barley (*Hordeum vulgare*), bermudagrass (*Cynodon dactylon*), downy bromegrass (*Bromus tectorum*), canarygrass (*Phalaris minor*), cocklebur (common cocklebur, *Xanthium strumarium*), woolly cupgrass (*Eriochloa villosa*), deadnettle (henbit deadnettle, *Lamium amplexicaule*), green foxtail (*Setaria viridis*), goosegrass (*Eleusine indica*), surinam grass (*Brachiaria decumbens*), windgrass (*Apera spica-venti*), chickweed (common chickweed, *Stellaria media*), kochia (*Kochia scoparia*), and wild oat (*Avena fatua*), were planted in pots containing Redi-Earth® planting medium (Scotts Company, 14111 Scottslawn Road, Marysville, Ohio 43041) comprising spaghnum peat moss, vermiculite, wetting agent and starter nutrients and treated with postemergence applications of test chemicals formulated in the same manner. Plants ranged in height from 2 to 18 cm (1- to 4-leaf stage) for postemergence treatments. Treated plants and controls were maintained in a greenhouse for 13 to 15 days, after which time all species were compared to controls and visually evaluated. Plant response ratings, summarized in Table C, are based on a scale of 0 to 100 where 0 is no effect and 100 is complete control. A dash (-) response means no test result.

TABLE C

| 500 g ai/ha | Compounds | | | | | | | | | | | | | |
|---|---|---|---|---|---|---|---|---|---|---|---|---|---|---|
| | 2 | 3 | 13 | 14 | 15 | 16 | 17 | 18 | 27 | 28 | 35 | 39 | 53 | 58 |
| Postemergence | | | | | | | | | | | | | | |
| Barley | — | — | — | — | — | — | 0 | 0 | — | — | 0 | 0 | 0 | 0 |
| Barnyardgrass | 0 | 10 | 0 | 0 | 0 | 0 | — | — | 10 | 0 | — | — | — | — |
| Bermudagrass | — | — | — | — | — | — | 0 | 5 | — | — | 0 | 0 | 5 | 10 |
| Blackgrass | 0 | 0 | 0 | 0 | 0 | 0 | 5 | 0 | 0 | 0 | 0 | 0 | 0 | 0 |
| Bromegrass, Downy | — | — | — | — | — | — | 0 | 0 | — | — | 0 | 5 | 0 | 0 |
| Canarygrass | — | — | — | — | — | — | 5 | 5 | — | — | 0 | 0 | 0 | 0 |
| Chickweed | 100 | 100 | 100 | 95 | 100 | 100 | 85 | 100 | 90 | 98 | 100 | 100 | 100 | 100 |
| Cocklebur | — | — | — | — | — | — | 40 | 20 | — | — | 75 | 55 | 15 | 95 |
| Corn | 0 | 5 | 0 | 5 | 0 | 0 | 10 | — | 0 | 0 | 5 | — | 5 | 5 |
| Crabgrass, Large | 0 | 5 | 0 | 0 | 0 | 0 | 15 | 20 | 10 | 0 | 5 | 15 | 0 | 5 |
| Cupgrass, Woolly | — | — | — | — | — | — | 15 | 20 | — | — | 5 | 0 | 5 | 0 |
| Deadnettle | — | — | — | — | — | — | 0 | 60 | — | — | 0 | 0 | 0 | 0 |
| Foxtail, Giant | 0 | 0 | 0 | 0 | 10 | 10 | 10 | 20 | 0 | 0 | 5 | 0 | 10 | 5 |
| Foxtail, Green | — | — | — | — | — | — | 0 | 0 | — | — | 20 | 5 | 0 | 30 |
| *Galium* | 50 | 30 | 10 | 45 | 45 | 50 | 20 | 35 | 0 | 30 | 5 | 0 | 10 | 5 |
| Goosegrass | — | — | — | — | — | — | 5 | 15 | — | — | 0 | 0 | 5 | 5 |
| Johnsongrass | 0 | 0 | 0 | 0 | 0 | 0 | 15 | 5 | 10 | 0 | 0 | 5 | 0 | 25 |
| *Kochia* | 95 | 85 | 90 | 90 | 90 | 90 | 55 | 60 | 90 | 90 | 95 | 80 | 60 | 98 |
| Lambsquarters | 90 | 100 | 98 | 100 | 90 | 75 | 98 | 90 | 98 | 98 | 100 | 100 | 100 | 100 |
| Morningglory | 10 | 0 | 10 | 5 | 20 | 0 | 15 | 45 | 55 | 0 | 5 | 10 | — | 0 |
| Nutsedge, Yellow | 0 | 0 | 0 | 0 | 0 | 5 | 5 | 5 | 0 | 0 | 5 | 5 | 0 | 0 |
| Oat, Wild | 0 | 0 | 5 | 5 | 0 | 0 | 0 | 0 | 5 | 0 | 0 | 5 | 0 | 0 |
| Oilseed Rape | 90 | 85 | 70 | 90 | 90 | 90 | — | — | 45 | 95 | — | — | — | — |
| Pigweed | 100 | — | 100 | 100 | 100 | 100 | 85 | 100 | 100 | 100 | 100 | 98 | 90 | 100 |
| Ragweed | 70 | 65 | 80 | 80 | 85 | 95 | 10 | 25 | 75 | 85 | 55 | 35 | 10 | 65 |
| Ryegrass, Italian | 0 | 0 | 0 | 5 | 0 | 0 | 5 | 5 | 5 | 0 | 0 | 0 | 0 | 0 |
| Soybean | 5 | 0 | 10 | 0 | 5 | 0 | 15 | 20 | 0 | 5 | 10 | 0 | 5 | 10 |
| Surinam Grass | — | — | — | — | — | — | 5 | 10 | — | — | 0 | 0 | 0 | 0 |
| Velvetleaf | 85 | 85 | 80 | 85 | 90 | 90 | 80 | 80 | 75 | 85 | 70 | 98 | — | 75 |
| Waterhemp | 100 | 95 | 100 | 100 | 100 | 100 | — | — | 100 | 100 | — | — | — | — |
| Wheat | 0 | 0 | 0 | 5 | 0 | 0 | 0 | 5 | 0 | 0 | 0 | 0 | 0 | 0 |
| Windgrass | — | — | — | — | — | — | 0 | 5 | — | — | 0 | 0 | 0 | 0 |

| 500 g ai/ha | Compound 66 |
|---|---|
| Postemergence | |
| Barley | 0 |
| Barnyardgrass | — |
| Bermudagrass | 0 |
| Blackgrass | 0 |
| Bromegrass, Downy | 0 |
| Canarygrass | 0 |
| Chickweed | 100 |
| Cocklebur | 90 |
| Corn | 5 |
| Crabgrass, Large | 0 |
| Cupgrass, Woolly | 0 |
| Deadnettle | 5 |
| Foxtail, Giant | 0 |
| Foxtail, Green | 0 |
| *Galium* | 5 |
| Goosegrass | 0 |
| Johnsongrass | 0 |
| *Kochia* | 95 |
| Lambsquarters | 90 |
| Morningglory | — |
| Nutsedge, Yellow | 0 |
| Oat, Wild | 0 |
| Oilseed Rape | — |
| Pigweed | 100 |
| Ragweed | 95 |
| Ryegrass, Italian | 0 |
| Soybean | 5 |
| Surinam Grass | 0 |
| Velvetleaf | 90 |
| Waterhemp | — |
| Wheat | 0 |
| Windgrass | 0 |

TABLE C-continued

| 250 g ai/ha | Compounds | | | | | | | | | | | | | |
|---|---|---|---|---|---|---|---|---|---|---|---|---|---|---|
| | 1 | 2 | 3 | 13 | 14 | 15 | 16 | 17 | 18 | 19 | 25 | 27 | 28 | 30 |
| Postemergence | | | | | | | | | | | | | | |
| Barley | — | — | — | — | — | — | — | 0 | 0 | — | 10 | — | — | 0 |
| Barnyardgrass | 0 | 0 | 5 | 0 | 0 | 0 | 0 | — | — | 0 | — | 0 | 0 | — |
| Bermudagrass | — | — | — | — | — | — | — | 0 | 0 | — | 0 | — | — | 0 |
| Blackgrass | 0 | 0 | 0 | 0 | 0 | 0 | 0 | 0 | 0 | 0 | 5 | 0 | 0 | 0 |
| Bromegrass, Downy | — | — | — | — | — | — | — | 0 | 0 | — | 0 | — | — | 0 |
| Canarygrass | — | — | — | — | — | — | — | 0 | 0 | — | 5 | — | — | 0 |
| Chickweed | 100 | 100 | 100 | 100 | 100 | 100 | 100 | 85 | 98 | 98 | 75 | 90 | 100 | 100 |
| Cocklebur | — | — | — | — | — | — | — | 30 | 15 | — | 25 | — | — | — |
| Corn | 0 | 0 | 5 | 0 | 5 | 0 | 0 | — | 10 | 0 | 0 | 0 | 0 | 0 |
| Crabgrass, Large | 0 | 0 | 5 | 10 | 0 | 0 | 0 | 10 | 15 | 10 | 0 | 10 | 0 | 0 |
| Cupgrass, Woolly | — | — | — | — | — | — | — | 0 | 15 | — | 0 | — | — | 0 |
| Deadnettle | — | — | — | — | — | — | — | 0 | 55 | — | 0 | — | — | 0 |
| Foxtail, Giant | 0 | 0 | 0 | 0 | 0 | 0 | 0 | 5 | 15 | 5 | 0 | 0 | 0 | 0 |
| Foxtail, Green | — | — | — | — | — | — | — | 0 | 0 | — | 15 | — | — | 0 |
| *Galium* | 20 | 50 | 20 | 40 | 50 | 10 | 20 | 0 | 0 | 45 | 0 | 0 | 35 | 5 |
| Goosegrass | — | — | — | — | — | — | — | 5 | 10 | — | 0 | — | — | 0 |
| Johnsongrass | 0 | 0 | 0 | 0 | 0 | 0 | 0 | 10 | 0 | 0 | 0 | 0 | 0 | 0 |
| *Kochia* | 90 | 90 | 85 | 85 | 90 | 85 | 90 | 50 | 45 | 90 | 15 | 90 | 85 | 98 |
| Lambsquarters | 85 | 85 | 80 | 98 | 100 | 80 | 75 | 80 | 85 | 10 | 20 | 98 | 98 | 100 |
| Morningglory | 0 | 0 | 0 | 10 | 0 | 10 | 0 | 10 | 20 | 0 | 0 | 0 | 0 | 0 |
| Nutsedge, Yellow | 10 | 0 | 0 | 0 | 0 | 0 | 0 | 5 | 5 | 5 | 0 | 0 | 5 | 0 |
| Oat, Wild | 0 | 0 | 0 | 0 | 0 | 0 | 0 | 0 | 0 | 0 | 10 | 5 | 0 | 0 |
| Oilseed Rape | 95 | 90 | 80 | 50 | 95 | 90 | 90 | — | — | 5 | — | 50 | 85 | — |
| Pigweed | 100 | 98 | 100 | 100 | 100 | 100 | 100 | — | 100 | 95 | 100 | 100 | 98 | 100 |
| Ragweed | 65 | 60 | 65 | 75 | 75 | 85 | 85 | 10 | 15 | 90 | 0 | 90 | 70 | 90 |
| Ryegrass, Italian | 0 | 0 | 0 | 0 | 0 | 0 | 0 | 0 | 0 | 5 | 5 | 5 | 0 | 0 |
| Soybean | 0 | 0 | 0 | 0 | 0 | 0 | 0 | 10 | 20 | 0 | 10 | 0 | 5 | 0 |
| Surinam Grass | — | — | — | — | — | — | — | 5 | 10 | — | 0 | — | — | 0 |
| Velvetleaf | 80 | 80 | 75 | 85 | 80 | 90 | 90 | 80 | 70 | 55 | 70 | 75 | 85 | 98 |
| Waterhemp | 98 | 100 | 90 | 100 | 100 | 100 | 98 | — | — | 95 | — | 98 | 98 | — |
| Wheat | 0 | 0 | 0 | 0 | 0 | 0 | 0 | 0 | 0 | 0 | 0 | 0 | 0 | 0 |
| Windgrass | — | — | — | — | — | — | — | 0 | 0 | — | 25 | — | — | 0 |

| 250 g ai/ha | Compounds | | | | | | | | | | | | |
|---|---|---|---|---|---|---|---|---|---|---|---|---|---|
| | 35 | 37 | 38 | 39 | 44 | 50 | 53 | 54 | 57 | 58 | 60 | 61 | 66 |
| Postemergence | | | | | | | | | | | | | |
| Barley | 0 | 0 | 0 | 0 | 0 | 0 | 0 | 0 | 0 | 0 | 0 | 0 | 0 |
| Barnyardgrass | — | — | — | — | — | — | — | — | — | — | — | — | — |
| Bermudagrass | 0 | 0 | 0 | 0 | 0 | 0 | 5 | 0 | 5 | 0 | 5 | 5 | 0 |
| Blackgrass | 0 | 0 | 5 | 0 | 0 | 0 | 0 | 0 | 0 | 0 | 0 | 0 | 0 |
| Bromegrass, Downy | 0 | 0 | 0 | 0 | 0 | 0 | 0 | 0 | 0 | 0 | 0 | 0 | 0 |
| Canarygrass | 0 | 0 | 5 | 0 | 0 | 0 | 0 | 0 | 0 | 0 | 0 | 0 | 0 |
| Chickweed | 100 | 75 | 100 | 100 | 50 | 100 | 100 | 100 | 100 | 100 | 100 | 75 | 100 |
| Cocklebur | 75 | 20 | 15 | 55 | 30 | 90 | 10 | 0 | 70 | 80 | 50 | 35 | — |
| Corn | 5 | 5 | — | — | 10 | 0 | 5 | 0 | 0 | 5 | 5 | 5 | 5 |
| Crabgrass, Large | 5 | 10 | 0 | 5 | 10 | 0 | 0 | 0 | 5 | 5 | 5 | 5 | 0 |
| Cupgrass, Woolly | 5 | 5 | 0 | 0 | 5 | 0 | 5 | 0 | 5 | 0 | 5 | 15 | 0 |
| Deadnettle | 0 | 0 | 5 | 0 | 0 | 40 | 0 | 5 | 0 | 0 | 0 | 0 | 0 |
| Foxtail, Giant | 0 | 25 | 0 | 0 | 20 | 0 | 10 | 5 | 5 | 0 | 5 | 10 | 0 |
| Foxtail, Green | 0 | 0 | 5 | 0 | 0 | 0 | 0 | 0 | 0 | 0 | 0 | 0 | 0 |
| *Galium* | 0 | 0 | 5 | 0 | 0 | 5 | 0 | 5 | 0 | 0 | 0 | 0 | 0 |
| Goosegrass | 0 | 0 | 0 | 0 | 0 | 0 | 5 | 0 | 0 | 0 | 0 | 5 | 0 |
| Johnsongrass | 0 | 0 | 0 | 0 | 5 | 0 | 0 | 0 | 0 | 0 | 5 | 10 | 0 |
| *Kochia* | 90 | 35 | 50 | 55 | 65 | 65 | 60 | 70 | 80 | 98 | 55 | 50 | 75 |
| Lambsquarters | 100 | 65 | 100 | 100 | 55 | 100 | 35 | 55 | — | 100 | 60 | 55 | 90 |
| Morningglory | 5 | 0 | 5 | 10 | 5 | 0 | — | 0 | — | 0 | 0 | 0 | — |
| Nutsedge, Yellow | 5 | 10 | 0 | 0 | 0 | 0 | 0 | 0 | 5 | 0 | 0 | 5 | 0 |
| Oat, Wild | 0 | 0 | 0 | 0 | 0 | 0 | 0 | 0 | 0 | 0 | 0 | 0 | 0 |
| Oilseed Rape | — | — | — | — | — | — | — | — | — | — | — | — | — |
| Pigweed | 100 | 100 | 100 | 98 | 100 | 100 | 90 | 100 | 75 | 100 | 100 | 100 | 95 |
| Ragweed | 50 | 20 | 35 | 35 | 10 | 45 | 10 | 20 | 70 | 50 | 35 | 40 | — |
| Ryegrass, Italian | 0 | 0 | 0 | 0 | 0 | 0 | 0 | 0 | 0 | 0 | 0 | 0 | 0 |
| Soybean | 10 | 5 | 0 | 0 | 5 | 0 | 0 | 0 | 0 | 10 | 5 | 15 | 0 |
| Surinam Grass | 0 | 0 | 0 | 0 | 0 | 0 | 0 | 0 | 0 | 0 | 5 | 0 | 0 |
| Velvetleaf | 70 | 98 | — | 85 | 80 | 95 | 90 | 100 | 80 | 70 | 80 | 75 | 80 |
| Waterhemp | — | — | — | — | — | — | — | — | — | — | — | — | — |
| Wheat | 0 | 0 | 5 | 0 | 0 | 0 | 0 | 0 | 0 | 0 | 0 | 0 | 0 |
| Windgrass | 0 | 0 | 0 | 0 | 0 | 0 | 0 | 0 | 0 | 0 | 0 | 0 | 0 |

TABLE C-continued

| 125 g ai/ha | Compounds | | | | | | | | | | | | | |
|---|---|---|---|---|---|---|---|---|---|---|---|---|---|---|
| | 1 | 2 | 3 | 13 | 14 | 15 | 16 | 17 | 18 | 19 | 25 | 27 | 28 | 30 |
| | Postemergence | | | | | | | | | | | | | |
| Barley | — | — | — | — | — | — | — | 0 | 0 | — | 5 | — | — | 0 |
| Barnyardgrass | 0 | 0 | 0 | 0 | 0 | 0 | 0 | — | — | 0 | — | 0 | 0 | — |
| Bermudagrass | — | — | — | — | — | — | — | 0 | 0 | — | 0 | — | — | 0 |
| Blackgrass | 0 | 0 | 0 | 0 | 0 | 0 | 0 | 0 | 0 | 0 | 0 | 5 | 0 | 0 |
| Bromegrass, Downy | — | — | — | — | — | — | — | 0 | 0 | — | 0 | — | — | 0 |
| Canarygrass | — | — | — | — | — | — | — | 0 | 0 | — | 0 | — | — | 0 |
| Chickweed | 100 | 100 | 100 | 85 | 100 | 95 | 100 | 65 | 80 | 98 | 75 | 85 | 95 | 100 |
| Cocklebur | — | — | — | — | — | — | — | 10 | 5 | — | 15 | — | — | — |
| Corn | 0 | 0 | 5 | 0 | 0 | 0 | 0 | — | 5 | 0 | 0 | 0 | 0 | 0 |
| Crabgrass, Large | 0 | 0 | 5 | 10 | 0 | 0 | 0 | 5 | 5 | 10 | 0 | 0 | 0 | 0 |
| Cupgrass, Woolly | — | — | — | — | — | — | — | 0 | 10 | — | 0 | — | — | 0 |
| Deadnettle | — | — | — | — | — | — | — | 0 | 40 | — | 0 | — | — | 0 |
| Foxtail, Giant | 0 | 0 | 0 | 0 | 0 | 0 | 0 | 0 | 10 | 5 | 0 | 0 | 5 | 0 |
| Foxtail, Green | — | — | — | — | — | — | — | 0 | 0 | — | 5 | — | — | 0 |
| *Galium* | 0 | 0 | 0 | 0 | 30 | 0 | 20 | 0 | 0 | 40 | 0 | 0 | 40 | 5 |
| Goosegrass | — | — | — | — | — | — | — | 0 | 0 | — | 0 | — | — | 0 |
| Johnsongrass | 0 | 0 | 0 | 0 | 0 | 0 | 0 | 0 | — | 0 | 0 | 0 | 0 | 0 |
| *Kochia* | 85 | 85 | 85 | 80 | 90 | 85 | 85 | 50 | 40 | 85 | 15 | 80 | 85 | 85 |
| Lambsquarters | 85 | 85 | — | 80 | 95 | 80 | 75 | 55 | 85 | 15 | 0 | 95 | 90 | 80 |
| Morningglory | 0 | 0 | 0 | 0 | 0 | 0 | 0 | 5 | 10 | 0 | 0 | 0 | 0 | 0 |
| Nutsedge, Yellow | 0 | 0 | 0 | 0 | 0 | 0 | 0 | 5 | 0 | 5 | 0 | 0 | 0 | 0 |
| Oat, Wild | 0 | 0 | 0 | 0 | 0 | 0 | 0 | 0 | 0 | 0 | 0 | 0 | 0 | 0 |
| Oilseed Rape | 80 | 70 | 70 | 55 | 70 | 90 | 60 | — | — | 0 | — | 50 | 85 | — |
| Pigweed | 100 | 90 | 95 | 100 | 98 | 100 | 85 | 80 | 100 | 90 | 98 | 95 | 98 | 100 |
| Ragweed | 50 | 60 | 25 | 50 | 70 | 75 | 85 | 10 | 10 | 80 | 0 | 75 | 45 | 35 |
| Ryegrass, Italian | 0 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 15 | 0 | 0 | 0 | 0 | 0 |
| Surinam Grass | — | — | — | — | — | — | — | 0 | 5 | — | 0 | — | — | 0 |
| Velvetleaf | 75 | 75 | 70 | 75 | 75 | 80 | 90 | 80 | 65 | 40 | 65 | 70 | 80 | 85 |
| Waterhemp | 90 | 85 | 90 | 100 | 95 | 95 | 95 | — | — | 80 | — | 98 | 98 | — |
| Wheat | 0 | 0 | 0 | 0 | 0 | 0 | 0 | 0 | 0 | 0 | 0 | 0 | 0 | 0 |
| Windgrass | — | — | — | — | — | — | — | 0 | 0 | — | 0 | — | — | 0 |

| 125 g ai/ha | Compounds | | | | | | | | | | | | |
|---|---|---|---|---|---|---|---|---|---|---|---|---|---|
| | 31 | 35 | 37 | 38 | 39 | 44 | 50 | 53 | 54 | 57 | 58 | 60 | 61 | 66 |
| | Postemergence | | | | | | | | | | | | |
| Barley | 0 | 0 | 0 | 0 | 0 | 0 | 0 | 0 | 0 | 0 | 0 | 0 | 0 | 0 |
| Barnyardgrass | — | — | — | — | — | — | — | — | — | — | — | — | — | — |
| Bermudagrass | 0 | 0 | 0 | 0 | 0 | 0 | 0 | 5 | 0 | 0 | 0 | 5 | 5 | 0 |
| Blackgrass | 0 | 0 | 0 | 0 | 0 | 0 | 0 | 0 | 0 | 0 | 0 | 0 | 0 | 0 |
| Bromegrass, Downy | 0 | 0 | 0 | 0 | 0 | 0 | 0 | 0 | 0 | 0 | 0 | 0 | 0 | 0 |
| Canarygrass | 0 | 0 | 0 | 0 | 0 | 0 | 0 | 0 | 0 | 0 | 0 | 0 | 0 | 0 |
| Chickweed | 80 | 100 | 70 | 60 | 98 | — | 100 | 50 | 100 | 100 | 100 | 100 | 75 | 100 |
| Cocklebur | 25 | 60 | 15 | 15 | 55 | 10 | 55 | 10 | 0 | 70 | 75 | 20 | 20 | 90 |
| Corn | 0 | 0 | 5 | — | — | 5 | 0 | 5 | 0 | 0 | 5 | 5 | 5 | 0 |
| Crabgrass, Large | 5 | 5 | 10 | 0 | 0 | 5 | 0 | 0 | 0 | 0 | 5 | 5 | 5 | 0 |
| Cupgrass, Woolly | 5 | 5 | 5 | 0 | 0 | 5 | 0 | 5 | 0 | 5 | 0 | 5 | 10 | 0 |
| Deadnettle | 10 | 0 | 0 | 0 | 0 | 0 | 0 | 0 | 0 | 0 | 0 | 0 | 0 | 0 |
| Foxtail, Giant | 5 | 0 | 25 | 0 | 0 | 0 | 0 | 0 | 5 | 0 | 0 | 5 | 5 | 0 |
| Foxtail, Green | 0 | 0 | 0 | 0 | 0 | 0 | 0 | 0 | 0 | 0 | 0 | 0 | 0 | 0 |
| *Galium* | 5 | 0 | 0 | 0 | 0 | 0 | 5 | 0 | 0 | 0 | 0 | 0 | 0 | 0 |
| Goosegrass | 0 | 0 | 0 | 0 | 0 | 0 | 0 | 5 | 0 | 0 | 0 | 0 | 0 | 0 |
| Johnsongrass | 10 | 0 | 0 | 0 | 0 | 0 | 0 | 0 | 0 | 0 | 25 | 5 | 10 | 0 |
| *Kochia* | 40 | 55 | 15 | — | 40 | 65 | 65 | 45 | 65 | 65 | 50 | 20 | 45 | 65 |
| Lambsquarters | 80 | 98 | 55 | 75 | 80 | 45 | 100 | 30 | 55 | 100 | 100 | 40 | 55 | 50 |
| Morningglory | 5 | 0 | 0 | 5 | 0 | 5 | 0 | — | 0 | — | 0 | 0 | 0 | — |
| Nutsedge, Yellow | 5 | 5 | 10 | 0 | 0 | 0 | 0 | 0 | 0 | 0 | 0 | 0 | 5 | 0 |
| Oat, Wild | 0 | 0 | 0 | 0 | 0 | 0 | 0 | 0 | 0 | 0 | 0 | 0 | 0 | 0 |
| Oilseed Rape | — | — | — | — | — | — | — | — | — | — | — | — | — | — |
| Pigweed | 75 | 100 | 80 | — | — | 60 | 100 | 85 | 100 | — | 100 | 65 | 100 | 85 |
| Ragweed | 5 | 40 | 5 | 20 | 10 | 5 | 0 | 10 | 0 | 65 | 40 | 30 | 40 | 80 |
| Ryegrass, Italian | 0 | 0 | 0 | 0 | 0 | 0 | 0 | 0 | 0 | 0 | 0 | 0 | 0 | 0 |
| Soybean | 5 | 10 | 5 | 0 | 0 | 5 | 0 | 0 | 0 | 0 | 5 | 5 | 10 | 0 |
| Surinam Grass | 5 | 0 | 0 | 0 | 0 | 0 | 0 | 0 | 0 | 0 | 0 | 0 | 0 | 0 |
| Velvetleaf | 80 | 65 | 80 | 90 | 85 | 75 | 90 | 75 | 85 | 80 | 65 | 70 | 75 | 55 |
| Waterhemp | — | — | — | — | — | — | — | — | — | — | — | — | — | — |
| Wheat | 0 | 0 | 0 | 0 | 0 | 0 | 0 | 0 | 0 | 0 | 0 | 0 | 0 | 0 |
| Windgrass | 0 | 0 | 0 | 0 | 0 | 0 | 0 | 0 | 0 | 0 | 0 | 0 | 0 | 0 |

TABLE C-continued

| 62 g ai/ha | Compounds | | | | | | | | | | | | | |
|---|---|---|---|---|---|---|---|---|---|---|---|---|---|---|
| | 1 | 2 | 3 | 13 | 14 | 15 | 16 | 17 | 18 | 19 | 25 | 27 | 28 | 30 |
| Postemergence | | | | | | | | | | | | | | |
| Barley | — | — | — | — | — | — | — | 0 | 0 | — | 0 | — | — | 0 |
| Barnyardgrass | 0 | 0 | 0 | 0 | 0 | 0 | 0 | — | — | 0 | — | 0 | 0 | — |
| Bermudagrass | — | — | — | — | — | — | — | 0 | 0 | — | 0 | — | — | 0 |
| Blackgrass | 0 | 0 | 0 | 5 | 0 | 0 | 0 | 0 | 0 | 0 | 0 | 0 | 0 | 0 |
| Bromegrass, Downy | — | — | — | — | — | — | — | 0 | 0 | — | 0 | — | — | 0 |
| Canarygrass | — | — | — | — | — | — | — | 0 | 0 | — | 0 | — | — | 0 |
| Chickweed | 100 | 98 | 100 | 100 | 90 | 95 | 95 | 10 | 50 | 80 | 75 | 80 | 95 | 100 |
| Cocklebur | — | — | — | — | — | — | — | 5 | 5 | — | 15 | — | — | — |
| Corn | 0 | 0 | 0 | 0 | 0 | 0 | 0 | — | — | 0 | 0 | 0 | 0 | 0 |
| Crabgrass, Large | 0 | 0 | 0 | 0 | 0 | 0 | 0 | 0 | 5 | 0 | 0 | 0 | 0 | 0 |
| Cupgrass, Woolly | — | — | — | — | — | — | — | 0 | 5 | — | 0 | — | — | 0 |
| Deadnettle | — | — | — | — | — | — | — | 0 | 20 | — | 0 | — | — | 0 |
| Foxtail, Giant | 0 | 0 | 0 | 0 | 0 | 0 | 0 | 0 | 5 | 0 | 0 | 0 | 0 | 0 |
| Foxtail, Green | — | — | — | — | — | — | — | 0 | 0 | — | 0 | — | — | 0 |
| *Galium* | 0 | 0 | 0 | 0 | 0 | 0 | 0 | 0 | 0 | 40 | 0 | 0 | 5 | 0 |
| Goosegrass | — | — | — | — | — | — | — | 0 | 0 | — | 0 | — | — | 0 |
| Johnsongrass | 0 | 0 | 0 | 0 | 0 | 0 | 0 | 0 | 0 | 0 | 0 | 0 | 0 | 0 |
| *Kochia* | 80 | 80 | 80 | 85 | 85 | 70 | 80 | 30 | 20 | 80 | 0 | 80 | 80 | 40 |
| Lambsquarters | 70 | 85 | 55 | 75 | 70 | 75 | 70 | 15 | 60 | 10 | 0 | 75 | 90 | 60 |
| Morningglory | 0 | 0 | 0 | 0 | 0 | 0 | 0 | 5 | 5 | 0 | 0 | 0 | 0 | 0 |
| Nutsedge, Yellow | 0 | 0 | 0 | 0 | 0 | 0 | 0 | 0 | 0 | 5 | 0 | 0 | 0 | 0 |
| Oat, Wild | 0 | 0 | 0 | 0 | 0 | 0 | 0 | 0 | 0 | 0 | 0 | 0 | 0 | 0 |
| Oilseed Rape | 50 | 70 | 60 | 40 | 80 | 60 | 50 | — | — | 0 | — | 45 | 80 | — |
| Pigweed | 98 | 90 | 85 | 75 | 85 | 90 | 85 | 75 | 85 | 85 | 80 | 80 | 90 | 100 |
| Ragweed | 40 | 40 | 20 | 50 | 60 | 60 | 60 | 0 | — | 70 | 0 | 65 | 60 | 20 |
| Ryegrass, Italian | 0 | 0 | 0 | 0 | 0 | 0 | 0 | 0 | 0 | 0 | 0 | 5 | 0 | 0 |
| Soybean | 0 | 0 | 0 | 0 | 0 | 0 | 0 | 0 | 5 | 0 | 0 | 0 | 0 | 0 |
| Surinam Grass | — | — | — | — | — | — | — | 0 | 5 | — | 0 | — | — | 0 |
| Velvetleaf | 70 | 75 | 70 | 70 | 75 | 80 | 85 | 80 | 50 | 25 | 55 | 65 | 80 | 85 |
| Waterhemp | 90 | 85 | 90 | 100 | 100 | 65 | 90 | — | — | 65 | — | 95 | 95 | — |
| Wheat | 0 | 0 | 0 | 0 | 0 | 0 | 0 | 0 | 0 | 0 | 0 | 0 | 0 | 0 |
| Windgrass | — | — | — | — | — | — | — | 0 | 0 | — | 0 | — | — | 0 |

| 62 g ai/ha | Compounds | | | | | | | | | | | | | |
|---|---|---|---|---|---|---|---|---|---|---|---|---|---|---|
| | 31 | 35 | 37 | 38 | 39 | 44 | 50 | 53 | 54 | 57 | 58 | 60 | 61 | 66 |
| Postemergence | | | | | | | | | | | | | | |
| Barley | 0 | 0 | 0 | 0 | 0 | 0 | 0 | 0 | 0 | 0 | 0 | 0 | 0 | 0 |
| Barnyardgrass | — | — | — | — | — | — | — | — | — | — | — | — | — | — |
| Bermudagrass | 0 | 0 | 0 | 0 | 0 | 0 | 0 | 5 | 0 | 0 | 0 | 5 | 5 | 0 |
| Blackgrass | 0 | 0 | 0 | 0 | 0 | 0 | 0 | 0 | 0 | 0 | 0 | 0 | 0 | 0 |
| Bromegrass, Downy | 0 | 0 | 0 | 0 | 0 | 0 | 0 | 0 | 0 | 0 | 0 | 0 | 0 | 0 |
| Canarygrass | 0 | 0 | 0 | 0 | 0 | 0 | 0 | 0 | 0 | 0 | 0 | 0 | 0 | 0 |
| Chickweed | 75 | 98 | — | 50 | 98 | 35 | 95 | 50 | 90 | 100 | 70 | — | — | 100 |
| Cocklebur | 20 | 60 | 10 | 10 | 15 | 0 | 15 | 5 | 0 | 70 | 60 | 15 | 10 | 40 |
| Corn | 0 | 0 | 0 | — | — | 5 | 0 | 5 | 0 | 0 | 0 | 5 | 5 | 0 |
| Crabgrass, Large | 5 | 5 | 10 | 0 | 0 | 5 | 0 | 0 | 0 | 0 | 5 | 0 | 5 | 0 |
| Cupgrass, Woolly | 5 | 5 | 5 | 0 | 0 | 5 | 0 | 5 | 0 | 0 | 0 | 0 | 10 | 0 |
| Deadnettle | 0 | 0 | 0 | 0 | 0 | 0 | 0 | 0 | 0 | 0 | 0 | 0 | 0 | 0 |
| Foxtail, Giant | 5 | 0 | 0 | 0 | 0 | 0 | 0 | 0 | 0 | 0 | 0 | 5 | 5 | 0 |
| Foxtail, Green | 0 | 0 | 0 | 0 | 0 | 0 | 0 | 0 | 0 | 0 | 0 | 0 | 0 | 0 |
| *Galium* | 0 | 0 | 0 | 0 | 0 | 0 | 0 | 0 | 0 | 0 | 0 | 0 | 0 | 0 |
| Goosegrass | 0 | 0 | 0 | 0 | 0 | 0 | 0 | 5 | 0 | 0 | 0 | 0 | 10 | 0 |
| Johnsongrass | 5 | 0 | 0 | 0 | 0 | 0 | 0 | 0 | 0 | 0 | 0 | 0 | 10 | 0 |
| *Kochia* | 40 | 50 | 15 | 35 | 15 | 55 | 60 | 25 | 60 | 65 | 15 | 10 | 40 | 60 |
| Lambsquarters | 55 | 98 | 45 | 75 | 80 | 45 | 80 | — | 50 | 60 | 70 | 5 | 40 | 40 |
| Morningglory | 5 | 0 | 0 | 0 | 0 | 0 | — | 0 | — | 0 | 0 | 0 | 0 | — |
| Nutsedge, Yellow | 5 | 0 | 10 | 0 | 0 | 0 | 0 | 0 | 0 | 0 | 0 | 0 | 0 | 0 |
| Oat, Wild | 0 | 0 | 0 | 0 | 0 | 0 | 0 | 0 | 0 | 0 | 0 | 0 | 0 | 0 |
| Oilseed Rape | — | — | — | — | — | — | — | — | — | — | — | — | — | — |
| Pigweed | — | 85 | 75 | 85 | 90 | 60 | 75 | 85 | 98 | 70 | 100 | 60 | 100 | 55 |
| Ragweed | 0 | 15 | 5 | 10 | 10 | 5 | 0 | 10 | 0 | 15 | 10 | 30 | 10 | 10 |
| Ryegrass, Italian | 0 | 0 | 0 | 0 | 0 | 0 | 0 | 0 | 0 | 0 | 0 | 0 | 0 | 0 |
| Soybean | 0 | 10 | 5 | 0 | 0 | 5 | 0 | 0 | 0 | 0 | 0 | 5 | 0 | 0 |
| Surinam Grass | 5 | 0 | 0 | 0 | 0 | 0 | 0 | 0 | 0 | 0 | 0 | 0 | 0 | 0 |
| Velvetleaf | 75 | 60 | 75 | 75 | 75 | 60 | 75 | 60 | 80 | 70 | 60 | 70 | 40 | 55 |
| Waterhemp | — | — | — | — | — | — | — | — | — | — | — | — | — | — |
| Wheat | 0 | 0 | 0 | 0 | 0 | 0 | 0 | 0 | 0 | 0 | 0 | 0 | 0 | 0 |
| Windgrass | 0 | 0 | 0 | 0 | 0 | 0 | 0 | 0 | 0 | 0 | 0 | 0 | 0 | 0 |

TABLE C-continued

| 31 g ai/ha | Compounds | | | | | | | | | | | | |
|---|---|---|---|---|---|---|---|---|---|---|---|---|---|
| | 1 | 19 | 25 | 30 | 31 | 37 | 38 | 44 | 50 | 54 | 57 | 60 | 61 |
| Postemergence | | | | | | | | | | | | | |
| Barley | — | — | 0 | 0 | 0 | 0 | 0 | 0 | 0 | 0 | 0 | 0 | 0 |
| Barnyardgrass | 0 | 0 | — | — | — | — | — | — | — | — | — | — | — |
| Bermudagrass | — | — | 0 | 0 | 0 | 0 | 0 | 0 | 0 | 0 | 0 | 0 | 0 |
| Blackgrass | 0 | 0 | 0 | 0 | 0 | 0 | 0 | 0 | 0 | 0 | 0 | 0 | 0 |
| Bromegrass, Downy | — | — | 0 | 0 | 0 | 0 | 0 | 0 | 0 | 0 | 0 | 0 | 0 |
| Canarygrass | — | — | 0 | 0 | 0 | 0 | 0 | 0 | 0 | 0 | 0 | 0 | 0 |
| Chickweed | 90 | 95 | 10 | 100 | 70 | 70 | 20 | 20 | 95 | 0 | 60 | 75 | 20 |
| Cocklebur | — | — | 5 | 10 | 20 | 5 | 5 | 0 | 5 | 0 | 10 | 10 | 10 |
| Corn | 0 | 0 | 0 | 0 | 0 | 0 | — | 0 | 0 | 0 | 0 | 5 | 5 |
| Crabgrass, Large | 0 | 0 | 0 | 0 | 5 | 10 | 0 | 0 | 0 | 0 | 0 | 0 | 5 |
| Cupgrass, Woolly | — | — | 0 | 0 | 5 | 5 | 0 | 0 | 0 | 0 | 0 | 0 | 5 |
| Deadnettle | — | — | 0 | 0 | 0 | 0 | 0 | 0 | 0 | 0 | 0 | 0 | 0 |
| Foxtail, Giant | 0 | 0 | 0 | 0 | 5 | 0 | 0 | 0 | 0 | 0 | 0 | 0 | 5 |
| Foxtail, Green | — | — | 0 | 0 | 0 | 0 | 0 | 0 | 0 | 0 | 0 | 0 | 0 |
| *Galium* | 0 | 15 | 0 | 0 | 0 | 0 | 0 | 0 | 0 | 0 | 0 | 0 | 0 |
| Goosegrass | — | — | 0 | 0 | 0 | 0 | 0 | 0 | 0 | 0 | 0 | 0 | 0 |
| Johnsongrass | 0 | 0 | 0 | 0 | 0 | 0 | 0 | 0 | 0 | 0 | 0 | 0 | 0 |
| *Kochia* | 80 | 70 | — | 35 | 15 | 10 | 35 | 45 | 5 | 60 | 50 | 10 | 20 |
| Lambsquarters | 70 | 35 | 0 | 45 | 25 | 10 | 60 | 0 | 0 | 20 | 50 | 5 | 5 |
| Morningglory | 0 | 0 | 0 | 0 | 5 | 0 | 0 | 0 | 0 | — | 0 | 0 | 0 |
| Nutsedge, Yellow | 0 | 5 | 0 | 0 | 0 | 5 | 0 | 0 | 0 | 0 | 0 | 0 | 0 |
| Oat, Wild | 0 | 0 | 0 | 0 | 0 | 0 | 0 | 0 | 0 | 0 | 0 | 0 | 0 |
| Oilseed Rape | 25 | 0 | — | — | — | — | — | — | — | — | — | — | — |
| Pigweed | 80 | 85 | 80 | 75 | 60 | 55 | 80 | 50 | 75 | 20 | 65 | 60 | 70 |
| Ragweed | 15 | 35 | 0 | 5 | 0 | 5 | 10 | 5 | 0 | 0 | 5 | 0 | 5 |
| Ryegrass, Italian | 0 | 0 | 0 | 0 | 0 | 0 | 0 | 0 | 0 | 0 | 0 | 0 | 0 |
| Soybean | 0 | 0 | 0 | 0 | 0 | 5 | 0 | 5 | 0 | 0 | 0 | 5 | 0 |
| Surinam Grass | — | — | 0 | 0 | 5 | 0 | 0 | 0 | 0 | 0 | 0 | 0 | 0 |
| Velvetleaf | 70 | 15 | 55 | 75 | 75 | 75 | 25 | 40 | 75 | 55 | 50 | 60 | 35 |
| Waterhemp | 85 | 75 | — | — | — | — | — | — | — | — | — | — | — |
| Wheat | 0 | 0 | 0 | 0 | 0 | 0 | 0 | 0 | 0 | 0 | 0 | 0 | 0 |
| Windgrass | — | — | 0 | 0 | 0 | 0 | 0 | 0 | 0 | 0 | 0 | 0 | 0 |

| 16 g ai/ha | Compound 31 |
|---|---|
| Postemergence | |
| Barley | 0 |
| Bermudagrass | 0 |
| Blackgrass | 0 |
| Bromegrass, Downy | 0 |
| Canarygrass | 0 |
| Chickweed | 10 |
| Cocklebur | 10 |
| Corn | 0 |
| Crabgrass, Large | 5 |
| Cupgrass, Woolly | 5 |
| Deadnettle | 0 |
| Foxtail, Giant | 5 |
| Foxtail, Green | 0 |
| *Galium* | 0 |
| Goosegrass | 0 |
| Johnsongrass | 0 |
| *Kochia* | 5 |
| Lambsquarters | 25 |
| Morningglory | 0 |
| Nutsedge, Yellow | 0 |
| Oat, Wild | 0 |
| Pigweed | 20 |
| Ragweed | 0 |
| Ryegrass, Italian | 0 |
| Soybean | 0 |
| Surinam Grass | 5 |
| Velvetleaf | 50 |
| Wheat | 0 |
| Windgrass | 0 |

TABLE C-continued

| 500 g ai/ha | Compounds | | | | | | | | |
|---|---|---|---|---|---|---|---|---|---|
| | 3 | 13 | 14 | 16 | 27 | 28 | 30 | 39 | 54 |
| Preemergence | | | | | | | | | |
| Barnyardgrass | 0 | 0 | 0 | 0 | 0 | 0 | 0 | 0 | 0 |
| Blackgrass | 0 | 40 | 30 | 0 | 0 | 5 | 0 | 0 | — |
| Corn | 0 | 0 | 0 | 0 | 0 | 0 | 0 | — | 10 |
| Crabgrass, Large | 0 | 0 | 0 | 0 | 0 | 15 | 0 | 0 | 30 |
| Foxtail, Giant | 0 | 0 | 0 | 0 | 0 | 10 | 0 | 0 | 0 |
| *Galium* | 0 | 0 | 0 | 0 | 30 | 80 | 10 | 80 | 5 |
| Johnsongrass | 0 | 0 | 0 | 0 | 0 | 0 | 0 | 0 | 0 |
| Lambsquarters | 100 | 100 | 100 | 100 | 100 | 100 | 100 | 100 | 100 |
| Morningglory | 10 | 0 | 0 | 0 | 0 | 0 | 15 | 20 | 40 |
| Nutsedge, Yellow | 0 | 0 | 0 | 0 | 0 | 0 | 0 | 0 | 25 |
| Oilseed Rape | 100 | 98 | 85 | 100 | 90 | 100 | 100 | 80 | 5 |
| Pigweed | 100 | 100 | 100 | 100 | 100 | 100 | 100 | 95 | 95 |
| Ragweed | 95 | 100 | 100 | 95 | 100 | 98 | 100 | 45 | 40 |
| Ryegrass, Italian | 0 | 0 | 0 | 0 | 0 | 0 | 0 | 0 | 0 |
| Soybean | 0 | 60 | 10 | 0 | 0 | 0 | 0 | 0 | 0 |
| Velvetleaf | 100 | 100 | 98 | 100 | 60 | 98 | 100 | 80 | 80 |
| Waterhemp | 100 | 100 | 100 | 100 | 100 | 100 | 100 | 100 | 100 |
| Wheat | 0 | 0 | 0 | 0 | 0 | 0 | — | 0 | 0 |

| 250 g ai/ha | Compounds | | | | | | | | | |
|---|---|---|---|---|---|---|---|---|---|---|
| | 3 | 13 | 14 | 15 | 16 | 19 | 27 | 28 | 30 | 39 | 54 |
| Preemergence | | | | | | | | | | |
| Barnyardgrass | 0 | 0 | 0 | 0 | 0 | 0 | 0 | 0 | 0 | 0 | 0 |
| Blackgrass | 0 | 50 | 0 | 0 | 0 | 50 | 50 | 5 | 0 | 0 | 0 |
| Corn | 0 | 0 | 0 | 0 | 0 | 0 | 0 | 0 | 0 | 0 | 10 |
| Crabgrass, Large | 0 | 0 | 0 | 0 | 0 | 0 | 0 | 15 | 0 | 0 | 0 |
| Foxtail, Giant | 0 | 0 | 0 | 0 | 0 | 0 | 0 | 10 | 0 | 0 | 0 |
| *Galium* | 0 | 30 | 80 | 0 | 0 | 100 | 80 | 80 | 5 | 5 | 0 |
| Johnsongrass | 0 | 0 | 0 | 0 | 0 | 0 | 0 | 0 | 0 | 0 | 0 |
| Lambsquarters | 100 | 100 | 100 | 100 | 100 | 100 | 100 | 100 | 100 | 100 | 50 |
| Morningglory | 10 | 0 | 0 | 0 | 0 | 10 | 0 | 0 | 15 | 20 | 15 |
| Nutsedge, Yellow | 0 | 0 | 0 | 0 | 0 | 0 | 0 | 0 | 0 | 0 | 0 |
| Oilseed Rape | 80 | 30 | 85 | 80 | 100 | 80 | 85 | 98 | 85 | 50 | 0 |
| Pigweed | 100 | 100 | 100 | 100 | 100 | 100 | 100 | 100 | 100 | 85 | 95 |
| Ragweed | 70 | 100 | 100 | 100 | 85 | 100 | 70 | 90 | 75 | 45 | 15 |
| Ryegrass, Italian | 0 | 0 | 0 | 0 | 0 | 10 | 0 | 0 | 0 | 0 | 0 |
| Soybean | 0 | 75 | 40 | 0 | 0 | 85 | 40 | 0 | 0 | 0 | 0 |
| Velvetleaf | 55 | 75 | 85 | 100 | 100 | 98 | 65 | 98 | 75 | 65 | 60 |
| Waterhemp | 100 | 100 | 100 | 100 | 100 | 100 | 100 | 100 | 100 | 100 | 98 |
| Wheat | 0 | 0 | 0 | 0 | 0 | 0 | 0 | 0 | 0 | 0 | 0 |

| 125 g ai/ha | Compounds | | | | | | | | | |
|---|---|---|---|---|---|---|---|---|---|---|
| | 3 | 13 | 14 | 15 | 16 | 19 | 27 | 28 | 30 | 39 | 54 |
| Preemergence | | | | | | | | | | |
| Barnyardgrass | 0 | 0 | 0 | 0 | 0 | 0 | 0 | 0 | 0 | 0 | 0 |
| Blackgrass | 0 | 10 | 20 | 0 | 0 | 0 | 0 | 0 | 0 | 0 | 0 |
| Corn | 0 | 0 | 0 | 0 | 0 | 0 | 0 | 0 | 0 | 0 | 0 |
| Crabgrass, Large | 0 | 0 | 0 | 0 | 0 | 0 | 0 | 0 | 0 | 0 | 0 |
| Foxtail, Giant | 0 | 0 | 0 | 0 | 0 | 0 | 0 | 0 | 0 | 0 | 0 |
| *Galium* | 0 | 0 | 60 | 0 | 0 | 95 | 50 | 80 | 0 | 0 | 0 |
| Johnsongrass | 0 | 0 | 0 | 0 | 0 | 0 | 0 | 0 | 0 | 0 | 0 |
| Lambsquarters | 100 | 100 | 100 | 100 | 100 | 100 | 100 | 100 | 100 | 100 | 40 |
| Morningglory | 0 | 0 | 0 | 0 | 0 | 0 | 0 | 0 | 15 | 20 | 0 |
| Nutsedge, Yellow | 0 | 0 | 0 | 0 | 0 | 0 | 0 | 0 | 0 | 0 | 0 |
| Oilseed Rape | 80 | 20 | 90 | 50 | 50 | 80 | 90 | 30 | 80 | 30 | 0 |
| Pigweed | 100 | 100 | 100 | 100 | 85 | 100 | 100 | 100 | 98 | 75 | — |
| Ragweed | 0 | 100 | 100 | 95 | 85 | 100 | 70 | 75 | — | 20 | 15 |
| Ryegrass, Italian | 0 | 0 | 0 | 0 | 0 | 0 | 0 | 0 | 0 | 0 | 0 |
| Soybean | 0 | 0 | 35 | 0 | 0 | 0 | 0 | 0 | 0 | 0 | 0 |
| Velvetleaf | — | 85 | 50 | 100 | 100 | 75 | 40 | 90 | 70 | 65 | 55 |
| Waterhemp | 100 | 100 | 100 | 100 | 100 | 100 | 100 | 100 | 100 | 100 | 95 |
| Wheat | 0 | 0 | 0 | 0 | 0 | 0 | 0 | 0 | 0 | 0 | 0 |

TABLE C-continued

| 62 g ai/ha | Compounds | | | | | | | | | | |
|---|---|---|---|---|---|---|---|---|---|---|---|
| | 3 | 13 | 14 | 15 | 16 | 19 | 27 | 28 | 30 | 39 | 54 |
| Preemergence | | | | | | | | | | | |
| Barnyardgrass | 0 | 0 | 0 | 0 | 0 | 0 | 0 | 0 | 0 | 0 | 0 |
| Blackgrass | 0 | 10 | 50 | 0 | 0 | 0 | 20 | 0 | 0 | 0 | 0 |
| Corn | 0 | 0 | 0 | 0 | 0 | 0 | 0 | 0 | 0 | 0 | 0 |
| Crabgrass, Large | 0 | 0 | 0 | 0 | 0 | 0 | 0 | 0 | 0 | 0 | 0 |
| Foxtail, Giant | 0 | 0 | 0 | 0 | 0 | 0 | 0 | 0 | 0 | 0 | 0 |
| *Galium* | 0 | 60 | 0 | 0 | 0 | 80 | 0 | 20 | 0 | 0 | 0 |
| Johnsongrass | 0 | 0 | 0 | 0 | 0 | 0 | 0 | 0 | 0 | 0 | 0 |
| Lambsquarters | 100 | 100 | 100 | 100 | 100 | 100 | 100 | 100 | 100 | 30 | 30 |
| Morningglory | 0 | 0 | 0 | 0 | 0 | 0 | 0 | 0 | 10 | 20 | 0 |
| Nutsedge, Yellow | 0 | 0 | 0 | 0 | 0 | 0 | 0 | 0 | 0 | 0 | 0 |
| Oilseed Rape | 40 | 50 | 50 | 50 | 0 | 0 | 70 | 5 | 50 | 0 | 0 |
| Pigweed | 30 | 90 | 98 | 100 | 85 | 85 | 98 | 100 | 60 | 45 | 90 |
| Ragweed | 0 | 85 | 75 | 35 | 55 | 85 | 98 | 65 | 50 | 0 | 5 |
| Ryegrass, Italian | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 |
| Velvetleaf | 50 | 60 | 75 | 60 | 65 | 40 | 10 | 65 | 65 | 55 | 45 |
| Waterhemp | 100 | 100 | 100 | 100 | 100 | 100 | 100 | 100 | 100 | 75 | 90 |
| Wheat | 0 | 0 | 0 | 0 | 0 | 0 | 0 | 0 | 0 | 0 | 0 |

| 31 g ai/ha | Compounds | |
|---|---|---|
| | 15 | 19 |
| Preemergence | | |
| Barnyardgrass | 0 | 0 |
| Blackgrass | 0 | 10 |
| Corn | 0 | 0 |
| Crabgrass, Large | 0 | 0 |
| Foxtail, Giant | 0 | 0 |
| *Galium* | 0 | 0 |
| Johnsongrass | 0 | 0 |
| Lambsquarters | 100 | 100 |
| Morningglory | 0 | 0 |
| Nutsedge, Yellow | 0 | 0 |
| Oilseed Rape | 0 | 0 |
| Pigweed | 100 | 75 |
| Ragweed | 0 | 35 |
| Ryegrass, Italian | 0 | 0 |
| Soybean | 0 | 0 |
| Velvetleaf | 35 | 20 |
| Waterhemp | 100 | 100 |
| Wheat | 0 | 0 |

Test D

Seeds of plant species selected from bluegrass (annual bluegrass, *Poa annua*), blackgrass (*Alopecurus myosuroides*), canarygrass (*Phalaris minor*), chickweed (common chickweed, *Stellaria media*), galium (catchweed bedstraw, *Galium aparine*), downy bromegrass (*Bromus tectorum*), field violet (*Viola arvensis*), green foxtail (*Setaria viridis*), deadnettle (henbit deadnettle, *Lamium amplexicaule*), Italian ryegrass (*Lolium multiflorum*), kochia (*Kochia scoparia*), lambsquarters (*Chenopodium album*), oilseed rape (*Brassica napus*), pigweed (*Amaranthus retroflexus*), Russian thistle (*Salsola kali*), spring barley (*Hordeum vulgare*), spring wheat (*Triticum aestivum*), wild buckwheat (*Polygonum convolvulus*), wild mustard (*Sinapis arvensis*), wild oat (*Avena fatua*), windgrass (*Apera spica-venti*), winter barley (*Hordeum vulgare*), and winter wheat (*Triticum aestivum*) were planted in pots containing Redi-Earth® planting medium (Scotts Company, 14111 Scottslawn Road, Marysville, Ohio 43041) comprising spaghnum peat moss, vermiculite, wetting agent and starter nutrients and treated with postemergence applications of test chemicals formulated in a non-phytotoxic solvent mixture which included a surfactant. Plants ranged in height from 2 to 18 cm (1- to 4-leaf stage). Treated plants and controls were maintained in a controlled growth environment for 14 days after which time all species were compared to controls and visually evaluated. Plant response ratings, summarized in Table D, are based on a scale of 0 to 100 where 0 is no effect and 100 is complete control. A dash (-) response means no test result.

TABLE D

| 250 g ai/ha | Compounds | | 125 g ai/ha | Compounds | |
|---|---|---|---|---|---|
| | 30 | 39 | | 30 | 39 |
| Postemergence | | | | | |
| Barley, Spring | 0 | 0 | Barley, Spring | 0 | 0 |
| Barley, Winter | 0 | 0 | Barley, Winter | 0 | 0 |
| Blackgrass | 10 | 20 | Blackgrass | 10 | 0 |
| Bluegrass | 0 | 0 | Bluegrass | 0 | 0 |
| Bromegrass, Downy | 0 | 0 | Bromegrass, Downy | 0 | 0 |
| Buckwheat, Wild | 35 | 20 | Buckwheat, Wild | 15 | 10 |
| Canarygrass | 10 | 0 | Canarygrass | 0 | 0 |
| Chickweed | 75 | 50 | Chickweed | 40 | 30 |
| Deadnettle | 10 | 0 | Deadnettle | 10 | 0 |
| Field Violet | 15 | — | Field Violet | 10 | 10 |

TABLE D-continued

| | | | | | |
|---|---|---|---|---|---|
| Foxtail, Green | 0 | 10 | Foxtail, Green | 0 | 0 |
| *Galium* | 0 | 0 | *Galium* | 0 | 0 |
| *Kochia* | 70 | 20 | *Kochia* | 40 | 10 |
| Lambsquarters | 50 | 25 | Lambsquarters | 40 | 20 |
| Mustard, Wild | 85 | 80 | Mustard, Wild | 70 | 70 |
| Oat, Wild | 0 | 0 | Oat, Wild | 0 | 0 |
| Oilseed Rape | 0 | 60 | Oilseed Rape | 85 | 20 |
| Pigweed | 90 | 80 | Pigweed | 80 | 75 |
| Russian Thistle | 50 | 25 | Russian Thistle | 40 | 20 |
| Ryegrass, Italian | 10 | 10 | Ryegrass, Italian | 0 | 0 |
| Wheat, Spring | 0 | 0 | Wheat, Spring | 0 | 0 |
| Wheat, Winter | 90 | 0 | Wheat, Winter | 0 | 0 |
| Windgrass | 0 | 0 | Windgrass | 0 | 0 |

| | Compounds | | | Compounds | |
|---|---|---|---|---|---|
| 62 g ai/ha | 30 | 39 | 31 g ai/ha | 30 | 39 |

Postemergence

| | | | | | |
|---|---|---|---|---|---|
| Barley, Spring | 0 | 0 | Barley, Spring | 0 | 0 |
| Barley, Winter | 0 | 0 | Barley, Winter | 0 | 0 |
| Blackgrass | 0 | 0 | Blackgrass | 0 | 0 |
| Bluegrass | 0 | 0 | Bluegrass | 0 | 0 |
| Bromegrass, Downy | 0 | 0 | Bromegrass, Downy | 0 | 0 |
| Buckwheat, Wild | 5 | 0 | Buckwheat, Wild | 0 | 0 |
| Canarygrass | 0 | 0 | Canarygrass | 0 | 0 |
| Chickweed | 10 | 10 | Chickweed | 0 | 0 |
| Deadnettle | 0 | 0 | Deadnettle | 0 | 0 |
| Field Violet | 10 | 10 | Field Violet | 0 | 0 |
| Foxtail, Green | 0 | 0 | Foxtail, Green | 0 | 0 |
| *Galium* | 0 | 0 | *Galium* | 0 | 0 |
| *Kochia* | 30 | 20 | *Kochia* | 10 | 0 |
| Lambsquarters | 30 | 10 | Lambsquarters | 0 | 0 |
| Mustard, Wild | 60 | 70 | Mustard, Wild | 60 | 20 |
| Oat, Wild | 0 | 0 | Oat, Wild | 0 | 0 |
| Oilseed Rape | 60 | 10 | Oilseed Rape | 50 | 0 |
| Pigweed | 70 | 50 | Pigweed | 60 | 30 |
| Russian Thistle | 20 | 10 | Russian Thistle | 10 | 0 |
| Ryegrass, Italian | 0 | 0 | Ryegrass, Italian | 0 | 0 |
| Wheat, Spring | 0 | 0 | Wheat, Spring | 0 | 0 |
| Wheat, Winter | 0 | 0 | Wheat, Winter | 0 | 0 |
| Windgrass | 0 | 0 | Windgrass | 0 | 0 |

| | Compounds | |
|---|---|---|
| 16 g ai/ha | 30 | 39 |

Postemergence

| | | |
|---|---|---|
| Barley, Spring | 0 | 0 |
| Barley, Winter | 0 | 0 |
| Blackgrass | 0 | 0 |
| Bluegrass | 0 | 0 |
| Bromegrass, Downy | 0 | 0 |
| Buckwheat, Wild | 0 | 0 |
| Canarygrass | 0 | 0 |
| Chickweed | 0 | 0 |
| Deadnettle | 0 | 0 |
| Field Violet | 0 | 0 |
| Foxtail, Green | 0 | 0 |
| *Galium* | 0 | 0 |
| *Kochia* | 0 | 0 |
| Lambsquarters | 0 | 0 |
| Mustard, Wild | 60 | 20 |
| Oat, Wild | 0 | 0 |
| Oilseed Rape | 30 | 0 |
| Pigweed | 25 | 30 |
| Russian Thistle | 0 | 0 |
| Ryegrass, Italian | 0 | 0 |
| Wheat, Spring | 0 | 0 |
| Wheat, Winter | 0 | 0 |
| Windgrass | 0 | 0 |

Test E

Seeds of plant species selected from corn (*Zea mays*), soybean (*Glycine max*), velvetleaf (*Abutilon theophrasti*), lambsquarters (*Chenopodium album*), wild poinsettia (*Euphorbia heterophylla*), palmer pigweed (*Amaranthus palmeri*), waterhemp (common waterhemp, *Amaranthus rudis*), surinam grass (*Brachiaria decumbens*), large (Lg) crabgrass (*Digitaria sanguinalis*), Brazilian crabgrass (*Digitaria horizontalis*), fall panicum (*Panicum dichotomiflorum*), giant foxtail (*Setaria faberii*), green foxtail (*Setaria viridis*), goosegrass (*Eleusine indica*), johnsongrass (*Sorghum halepense*), ragweed (common ragweed, *Ambrosia elatior*), barnyardgrass (*Echinochloa crus-galli*), sandbur (southern sandbur, *Cenchrus echinatus*), arrowleaf sida (*Sida rhombifolia*), Italian ryegrass (*Lolium multiflorum*), dayflower (Virginia (VA) dayflower, *Commelina virginica*), field bindweed (*Convolvulus arvensis*), morningglory (*Ipomoea coccinea*), nightshade (eastern black nightshade, *Solanum ptycanthum*), kochia (*Kochia scoparia*), yellow nutsedge (*Cyperus esculentus*), smartweed (ladysthumb smartweed, *Polygonum persicaria*), cocklebur (common cocklebur, *Xanthium strumarium*), and hairy beggarticks (*Bidens pilosa*), were planted into a silt loam soil and treated preemergence with test chemicals formulated in a non-phytotoxic solvent mixture which included a surfactant.

At the same time, plants from these crop and weed species and also waterhemp_RES1, (ALS & Triazine resistant common waterhemp, *Amaranthus rudis*), and waterhemp_RES2, (ALS & HPPD resistant common waterhemp, *Amaranthus rudis*) were planted in pots containing Redi-Earth® planting medium (Scotts Company, 14111 Scottslawn Road, Marysville, Ohio 43041) comprising spaghnum peat moss, vermiculite, wetting agent and starter nutrients were treated with postemergence applications of test chemicals formulated in the same manner. Plants ranged in height from 2 to 18 cm for postemergence treatments (1- to 4-leaf stage).

Treated plants and controls were maintained in a greenhouse for 14 to 21 days, after which time all species were compared to controls and visually evaluated. Plant response ratings, summarized in Table E, are based on a scale of 0 to 100 where 0 is no effect and 100 is complete control. A dash (-) response means no test result.

TABLE E

| | Compounds | | | | | | | | | | | | | |
|---|---|---|---|---|---|---|---|---|---|---|---|---|---|---|
| 500 g ai/ha | 1 | 2 | 3 | 13 | 14 | 15 | 16 | 17 | 18 | 28 | 35 | 39 | 50 | 58 |
| Postemergence | | | | | | | | | | | | | | |
| Arrowleaf Sida | 98 | 98 | 98 | 90 | 95 | 98 | 100 | 85 | 85 | 90 | 90 | 90 | 80 | 80 |
| Barnyardgrass | 0 | 0 | 0 | 40 | 10 | 0 | 0 | 20 | 25 | 0 | 0 | 10 | 10 | 0 |
| Beggarticks | 98 | 100 | 98 | 90 | 98 | 98 | 98 | 60 | — | 98 | 100 | 95 | — | 100 |
| Corn | 0 | 0 | 0 | 0 | 0 | 0 | 0 | 10 | 0 | 0 | 0 | 0 | 0 | 0 |
| Crabgrass, Brazil | 0 | 0 | 0 | 0 | 0 | 0 | 0 | 15 | 20 | 0 | 10 | 5 | 0 | 10 |
| Dayflower, VA | 0 | 0 | 0 | 10 | 0 | 0 | 0 | 0 | 5 | 0 | 0 | 0 | 0 | 0 |
| Field Bindweed | 0 | 0 | 0 | 10 | 0 | 0 | 0 | 30 | 35 | 20 | 15 | 10 | 5 | 10 |

TABLE E-continued

| | | | | | | | | | | | | | |
|---|---|---|---|---|---|---|---|---|---|---|---|---|---|
| *Panicum*, Fall | 0 | 40 | 0 | 0 | — | 35 | 65 | 0 | 10 | 0 | — | 0 | 0 | — |
| Pigweed, Palmer | 98 | 100 | 75 | 95 | 100 | 100 | 100 | 95 | 98 | 90 | 100 | 98 | 98 | 100 |
| Poinsettia, Wild | 0 | 0 | 10 | 0 | 5 | 0 | 0 | 30 | 40 | 15 | 0 | 10 | 30 | 0 |
| Ryegrass, Italian | 0 | 0 | 0 | 0 | 0 | 0 | 0 | 0 | 0 | 0 | 0 | 0 | 0 | 0 |
| Sandbur | 0 | 0 | 0 | 0 | 0 | 0 | 0 | 10 | 20 | 0 | 0 | 0 | 0 | 0 |
| Smartweed | 85 | — | 90 | — | — | — | — | — | 20 | — | — | — | — | — |
| Soybean | 0 | 0 | 0 | 0 | 0 | 0 | 0 | 20 | 30 | 0 | 0 | 20 | 0 | 0 |
| Waterhemp | 100 | 100 | 98 | 95 | 100 | 100 | 100 | 95 | 95 | 90 | 100 | 98 | 100 | 100 |
| Waterhemp_RES1 | — | — | — | 100 | 100 | — | — | 85 | 95 | 90 | — | 95 | — | — |
| Waterhemp_RES2 | 98 | 98 | 95 | 95 | 95 | 98 | 100 | 95 | 95 | 90 | — | 90 | 100 | — |

| | Compound | | | Compounds | | |
|---|---|---|---|---|---|---|
| 500 g ai/ha | | 61 | 250 g ai/ha | 58 | 60 | 61 |

Postemergence

| | | | | | | |
|---|---|---|---|---|---|---|
| Arrowleaf Sida | | 70 | Arrowleaf Sida | 75 | 45 | 60 |
| Barnyardgrass | | 20 | Barnyardgrass | 0 | 0 | 10 |
| Beggarticks | | — | Beggarticks | 95 | — | — |
| Corn | | 0 | Corn | 0 | 0 | 0 |
| Crabgrass, Brazil | | 0 | Crabgrass, Brazil | 0 | 0 | 0 |
| Dayflower, VA | | 0 | Dayflower, VA | 0 | 0 | 0 |
| Field Bindweed | | 5 | Field Bindweed | 0 | 0 | 0 |
| *Panicum*, Fall | | 0 | *Panicum*, Fall | 0 | 0 | 0 |
| Pigweed, Palmer | | 95 | Pigweed, Palmer | 95 | 35 | 80 |
| Poinsettia, Wild | | 30 | Poinsettia, Wild | 0 | 0 | 10 |
| Ryegrass, Italian | | 0 | Ryegrass, Italian | 0 | 0 | 0 |
| Sandbur | | 0 | Sandbur | 0 | 0 | 0 |
| Smartweed | | — | Smartweed | — | 0 | — |
| Soybean | | 10 | Soybean | 0 | 0 | 0 |
| Waterhemp | | — | Waterhemp | 100 | 30 | 100 |
| Waterhemp_RES1 | | — | Waterhemp_RES1 | — | — | — |
| Waterhemp_RES2 | | 95 | Waterhemp_RES2 | — | 25 | — |

| | Compounds | | | | | | | | | | | | |
|---|---|---|---|---|---|---|---|---|---|---|---|---|---|
| 250 g ai/ha | 1 | 2 | 3 | 14 | 15 | 16 | 17 | 18 | 28 | 30 | 35 | 39 | 50 | 54 |

Postemergence

| | | | | | | | | | | | | | | |
|---|---|---|---|---|---|---|---|---|---|---|---|---|---|---|
| Arrowleaf Sida | 95 | 95 | 95 | 90 | 98 | 98 | 80 | 80 | 85 | 80 | 80 | 90 | 70 | 75 |
| Barnyardgrass | 0 | 0 | 0 | 0 | 0 | 0 | 0 | 25 | 0 | 0 | 0 | 0 | 0 | 0 |
| Beggarticks | 98 | 100 | 98 | 95 | 100 | 98 | 40 | — | 98 | 100 | 98 | 95 | — | — |
| Corn | 0 | 0 | 0 | 0 | 0 | 0 | 0 | 0 | 0 | 0 | 0 | 0 | 0 | 0 |
| Crabgrass, Brazil | 0 | 0 | 0 | 0 | 0 | 0 | 0 | 20 | 0 | 0 | 0 | 0 | 0 | 0 |
| Dayflower, VA | 0 | 0 | 0 | 0 | 0 | 0 | 0 | 0 | 0 | 0 | 0 | 0 | 0 | 0 |
| Field Bindweed | 0 | 0 | 0 | 0 | 0 | 0 | 30 | 25 | 10 | 0 | 0 | 10 | 0 | 0 |
| *Panicum*, Fall | 0 | 25 | 0 | 0 | 0 | 30 | 0 | 0 | 0 | 0 | — | 0 | 0 | 0 |
| Pigweed, Palmer | 70 | 95 | 90 | 100 | 98 | 90 | 85 | 98 | 80 | 100 | 100 | 85 | 98 | 95 |
| Poinsettia, Wild | 0 | 0 | 15 | 10 | 0 | 0 | 20 | 30 | 10 | 0 | 0 | 0 | 20 | 0 |
| Ryegrass, Italian | 0 | 0 | 0 | 0 | 0 | 0 | 0 | 0 | 0 | 5 | 0 | 0 | 0 | 0 |
| Sandbur | 0 | 0 | 0 | 0 | 0 | 0 | 0 | 15 | 0 | 0 | 0 | 0 | 0 | 0 |
| Smartweed | 75 | 95 | 65 | — | — | — | — | — | — | — | — | — | — | 0 |
| Soybean | 0 | 0 | 0 | 0 | 0 | 0 | 15 | 20 | 0 | 0 | 0 | 10 | 0 | 0 |
| Waterhemp | 98 | 98 | 90 | 100 | 100 | 98 | 90 | 90 | 90 | 75 | 98 | 95 | 100 | 95 |
| Waterhemp_RES1 | — | — | — | 100 | — | — | 85 | 95 | 95 | — | — | 90 | — | — |
| Waterhemp_RES2 | 98 | 95 | 95 | 95 | 90 | 98 | 85 | 90 | 85 | — | — | 90 | 100 | 85 |

| | Compounds | | | | | | | | | | | |
|---|---|---|---|---|---|---|---|---|---|---|---|---|
| 125 g ai/ha | 1 | 2 | 3 | 13 | 14 | 15 | 16 | 17 | 18 | 28 | 30 | 31 | 35 | 39 |

Postemergence

| | | | | | | | | | | | | | | |
|---|---|---|---|---|---|---|---|---|---|---|---|---|---|---|
| Arrowleaf Sida | 95 | 95 | 90 | 80 | 90 | 98 | 98 | 75 | 80 | 75 | 80 | 90 | 70 | 85 |
| Barnyardgrass | 0 | 0 | 0 | 15 | 0 | 0 | 0 | 0 | 20 | 0 | 0 | — | 0 | 0 |
| Beggarticks | 98 | 100 | 98 | 60 | 95 | 98 | 98 | 35 | — | 95 | 85 | 85 | 98 | 90 |
| Corn | 0 | 0 | 0 | 0 | 0 | 0 | 0 | 0 | 0 | 0 | 0 | — | 0 | 0 |
| Crabgrass, Brazil | 0 | 0 | 0 | 0 | 0 | 0 | 0 | 0 | 15 | 0 | 0 | — | 0 | 0 |
| Dayflower, VA | 0 | 0 | 0 | 10 | 0 | 0 | 0 | 0 | 0 | 0 | 0 | — | 0 | 0 |
| Field Bindweed | 0 | 0 | 0 | 0 | 0 | 0 | 0 | 20 | 25 | 0 | 0 | — | 0 | 0 |
| *Panicum*, Fall | 0 | 0 | 0 | 0 | 0 | 0 | 60 | 0 | 0 | 0 | 0 | — | — | 0 |
| Pigweed, Palmer | 75 | 90 | 75 | 85 | 95 | 75 | 90 | 80 | 90 | 70 | 100 | 75 | 98 | 80 |
| Poinsettia, Wild | 0 | 0 | 0 | 0 | 0 | 0 | 0 | 0 | 30 | 0 | 0 | — | 0 | 0 |
| Ryegrass, Italian | 0 | 0 | 0 | 0 | 0 | 0 | 0 | 0 | 0 | 0 | 0 | — | 0 | 0 |
| Sandbur | 0 | 0 | 0 | 0 | 0 | 0 | 0 | 0 | 0 | 0 | 0 | — | 0 | 0 |
| Smartweed | 50 | 75 | — | — | — | — | — | — | — | — | — | — | — | — |
| Soybean | 0 | 0 | 0 | 0 | 0 | 0 | 0 | 0 | 10 | 0 | 0 | — | 0 | 0 |
| Waterhemp | 98 | 98 | 98 | 90 | 98 | 95 | 98 | 85 | 85 | 85 | 70 | 60 | 95 | 90 |

TABLE E-continued

| | | | | | | | | | | | | | | |
|---|---|---|---|---|---|---|---|---|---|---|---|---|---|---|
| Waterhemp_RES1 | — | — | — | 90 | 95 | — | — | — | 85 | 90 | — | — | — | 90 |
| Waterhemp_RES2 | 35 | 85 | 70 | 75 | 90 | 75 | 75 | 80 | 85 | 80 | — | — | — | 85 |

| 125 g ai/ha | Compounds | | | | |
|---|---|---|---|---|---|
| | 50 | 54 | 58 | 60 | 61 |
| Postemergence | | | | | |
| Arrowleaf Sida | 60 | 65 | 60 | 45 | 40 |
| Barnyardgrass | 0 | 0 | 0 | 0 | 0 |
| Beggarticks | — | — | 80 | — | — |
| Corn | 0 | 0 | 0 | 0 | 0 |
| Crabgrass, Brazil | 0 | 0 | 0 | 0 | 0 |
| Dayflower, VA | 0 | 0 | 0 | 0 | 0 |
| Field Bindweed | 0 | 0 | 0 | 0 | 0 |
| *Panicum*, Fall | 0 | 0 | — | 0 | 0 |
| Pigweed, Palmer | 80 | 75 | 95 | 35 | 60 |
| Poinsettia, Wild | 0 | 0 | 0 | 0 | 0 |
| Ryegrass, Italian | 0 | 0 | 0 | 0 | 0 |
| Sandbur | 0 | 0 | 0 | 0 | 0 |
| Smartweed | — | — | 50 | 0 | — |
| Soybean | 0 | 0 | 0 | 0 | 0 |
| Waterhemp | 90 | 70 | 95 | 25 | 75 |
| Waterhemp_RES1 | — | — | — | — | — |
| Waterhemp_RES2 | 100 | 85 | — | 20 | 40 |

| 62 g ai/ha | Compounds | | | | | | | | | | | | | |
|---|---|---|---|---|---|---|---|---|---|---|---|---|---|---|
| | 1 | 2 | 3 | 14 | 15 | 16 | 17 | 18 | 28 | 30 | 31 | 35 | 39 | 50 |
| Postemergence | | | | | | | | | | | | | | |
| Arrowleaf Sida | 90 | 95 | 95 | 90 | 90 | 98 | 70 | 70 | 60 | 70 | 80 | 60 | 80 | 50 |
| Barnyardgrass | 0 | 0 | 0 | 0 | 0 | 0 | 0 | 10 | 0 | 0 | — | 0 | 0 | 0 |
| Beggarticks | 95 | 90 | 95 | 90 | 98 | 100 | 25 | — | 90 | — | 85 | 98 | 85 | — |
| Corn | 0 | 0 | 0 | 0 | 0 | 0 | 0 | 0 | 0 | 0 | — | 0 | 0 | 0 |
| Crabgrass, Brazil | 0 | 0 | 0 | 0 | 0 | 0 | 0 | 5 | 0 | 0 | — | 0 | 0 | 0 |
| Dayflower, VA | 0 | 0 | 0 | 0 | 0 | 0 | 0 | 0 | 0 | 0 | — | 0 | 0 | 0 |
| Field Bindweed | 0 | 0 | 0 | 0 | 0 | 0 | 10 | 15 | 0 | 0 | — | 0 | 0 | 0 |
| *Panicum*, Fall | 0 | 0 | 0 | 0 | 0 | 0 | 0 | 0 | 0 | 0 | — | — | 0 | 0 |
| Pigweed, Palmer | 25 | 85 | 50 | 90 | 75 | 70 | 70 | 90 | 70 | 100 | 60 | 80 | 80 | 75 |
| Poinsettia, Wild | 0 | 0 | 0 | 0 | 0 | 0 | 0 | 20 | 0 | 0 | — | 0 | 0 | 0 |
| Ryegrass, Italian | 0 | 0 | 0 | 0 | 0 | 0 | 0 | 0 | 0 | 0 | — | 0 | 0 | 0 |
| Sandbur | 0 | 0 | 0 | 0 | 0 | 0 | 0 | 0 | 0 | 0 | — | 0 | 0 | 0 |
| Smartweed | 35 | 65 | — | — | 75 | — | — | — | — | — | — | — | — | — |
| Soybean | 0 | 0 | 0 | 0 | 0 | 0 | 0 | 0 | 0 | 0 | — | 0 | 0 | 0 |
| Waterhemp | 90 | 80 | 98 | 95 | 98 | 98 | 80 | 75 | 85 | 70 | — | 85 | — | — |
| Waterhemp_RES1 | — | — | — | 95 | — | — | 70 | 70 | 85 | — | — | — | 85 | — |
| Waterhemp_RES2 | — | 65 | 80 | 85 | 70 | 95 | 75 | 80 | 60 | — | — | — | 75 | — |

| 62 g ai/ha | Compounds | | | | 31 g ai/ha | Compounds | | | |
|---|---|---|---|---|---|---|---|---|---|
| | 54 | 58 | 60 | 61 | | 54 | 58 | 60 | 61 |
| Postemergence | | | | | | | | | |
| Arrowleaf Sida | 50 | 50 | 35 | 40 | Arrowleaf Sida | 50 | 50 | 35 | 30 |
| Barnyardgrass | 0 | 0 | 0 | 0 | Barnyardgrass | 0 | 0 | 0 | 0 |
| Beggarticks | — | 80 | — | — | Beggarticks | — | 70 | — | — |
| Corn | 0 | 0 | 0 | 0 | Corn | 0 | 0 | 0 | 0 |
| Crabgrass, Brazil | 0 | 0 | 0 | 0 | Crabgrass, Brazil | 0 | 0 | 0 | 0 |
| Dayflower, VA | 0 | 0 | 0 | 0 | Dayflower, VA | 0 | 0 | 0 | 0 |
| Field Bindweed | 0 | 0 | 0 | 0 | Field Bindweed | 0 | 0 | 0 | 0 |
| *Panicum*, Fall | 0 | — | 0 | 0 | *Panicum*, Fall | 0 | 0 | 0 | 0 |
| Pigweed, Palmer | 60 | 80 | 30 | 60 | Pigweed, Palmer | 40 | 80 | — | 50 |
| Poinsettia, Wild | 0 | 0 | 0 | 0 | Poinsettia, Wild | 0 | 0 | 0 | 0 |
| Ryegrass, Italian | 0 | 0 | 0 | 0 | Ryegrass, Italian | 0 | 0 | 0 | 0 |
| Sandbur | 0 | 0 | 0 | 0 | Sandbur | 0 | 0 | 0 | 0 |
| Smartweed | — | — | 0 | — | Smartweed | — | 0 | 0 | — |
| Soybean | 0 | 0 | 0 | 0 | Soybean | 0 | 0 | 0 | 0 |
| Waterhemp | 60 | 90 | 25 | 30 | Waterhemp | — | 80 | 20 | 20 |
| Waterhemp_RES1 | — | — | — | — | Waterhemp_RES1 | — | — | — | — |
| Waterhemp_RES2 | 80 | — | 20 | — | Waterhemp_RES2 | — | — | — | 20 |

TABLE E-continued

| 31 g ai/ha | Compounds | | | | | | | | | | | | | |
|---|---|---|---|---|---|---|---|---|---|---|---|---|---|---|
| | 1 | 2 | 3 | 14 | 15 | 16 | 17 | 18 | 28 | 30 | 31 | 35 | 39 | 50 |
| Postemergence | | | | | | | | | | | | | | |
| Arrowleaf Sida | 80 | 95 | 85 | 80 | 98 | 95 | 60 | 60 | 65 | 50 | 65 | 50 | 75 | 50 |
| Barnyardgrass | 0 | 0 | 0 | 0 | 0 | 0 | 0 | 0 | 0 | 0 | — | 0 | 0 | 0 |
| Beggarticks | 30 | 80 | 60 | 80 | 90 | 95 | 5 | — | 80 | — | 80 | 85 | 80 | — |
| Corn | 0 | 0 | 0 | 0 | 0 | 0 | 0 | 0 | 0 | 0 | — | 0 | 0 | 0 |
| Crabgrass, Brazil | 0 | 0 | 0 | 0 | 0 | 0 | 0 | 0 | 0 | 0 | — | 0 | 0 | 0 |
| Dayflower, VA | 0 | 0 | 0 | 0 | 0 | 0 | 0 | 0 | 0 | 0 | — | 0 | 0 | 0 |
| Field Bindweed | 0 | 0 | 0 | 0 | 0 | 0 | 0 | 0 | 0 | 0 | — | 0 | 0 | 0 |
| *Panicum*, Fall | 0 | 0 | 0 | 0 | 0 | 0 | 0 | 0 | 0 | 0 | — | — | 0 | 0 |
| Pigweed, Palmer | 50 | 65 | 40 | 80 | 35 | 70 | 60 | 90 | 50 | 40 | — | 75 | 70 | 65 |
| Poinsettia, Wild | 0 | 0 | 0 | 0 | 0 | 0 | 0 | 5 | 0 | 0 | — | 0 | 0 | 0 |
| Ryegrass, Italian | 0 | 0 | 0 | 0 | 0 | 0 | 0 | 0 | 0 | 0 | — | 0 | 0 | 0 |
| Sandbur | 0 | 0 | 0 | 0 | 0 | 0 | 0 | 0 | 0 | 0 | — | 0 | 0 | 0 |
| Smartweed | 0 | 0 | — | — | 0 | — | — | — | — | — | — | — | — | — |
| Soybean | 0 | 0 | 0 | 0 | 0 | 0 | 0 | 0 | 0 | 0 | — | 0 | 0 | 0 |
| Waterhemp | 65 | 90 | 95 | 90 | 80 | 95 | 50 | 50 | 80 | 60 | 50 | — | 80 | 80 |
| Waterhemp_RES1 | — | — | — | 90 | — | — | 70 | 60 | 85 | — | — | — | 85 | — |
| Waterhemp_RES2 | 40 | 0 | 60 | 75 | 60 | 95 | 60 | 65 | 50 | — | — | — | 70 | 75 |

| 16 g ai/ha | Compounds | | | | 1000 g ai/ha | Compound |
|---|---|---|---|---|---|---|
| | 30 | 31 | 54 | 60 | | 54 |
| Postemergence | | | | | Preemergence | |
| Arrowleaf Sida | 50 | 55 | 30 | 25 | Arrowleaf Sida | 100 |
| Barnyardgrass | 0 | — | 0 | 0 | Beggarticks | 90 |
| Beggarticks | 80 | 70 | — | — | Corn | 0 |
| Corn | 0 | — | 0 | 0 | Dayflower, VA | 0 |
| Crabgrass, Brazil | 0 | — | 0 | 0 | Field Bindweed | 0 |
| Dayflower, VA | 0 | — | 0 | 0 | *Kochia* | 97 |
| Field Bindweed | 0 | — | 0 | 0 | Lambsquarters | 99 |
| *Panicum*, Fall | 0 | — | 0 | 0 | Morningglory | 25 |
| Pigweed, Palmer | 0 | 50 | 20 | 20 | Nightshade | 0 |
| Poinsettia, Wild | 0 | — | 0 | 0 | Pigweed, Palmer | 100 |
| Ryegrass, Italian | 0 | — | 0 | 0 | Poinsettia, Wild | 40 |
| Sandbur | 0 | — | 0 | 0 | Ragweed | 84 |
| Smartweed | — | — | — | 0 | Smartweed | 50 |
| Soybean | 0 | — | 0 | 0 | Soybean | 20 |
| Waterhemp | 25 | 50 | 50 | 20 | Velvetleaf | 98 |
| Waterhemp_RES2 | — | — | 50 | 15 | Waterhemp | 100 |

| 500 g ai/ha | Compounds | | | | | | | |
|---|---|---|---|---|---|---|---|---|
| | 1 | 2 | 3 | 15 | 16 | 28 | 31 | 39 |
| Preemergence | | | | | | | | |
| Arrowleaf Sida | 75 | 95 | 98 | 98 | 100 | 100 | 95 | 95 |
| Barnyardgrass | 0 | 0 | 0 | 0 | 0 | 0 | 0 | 0 |
| Beggarticks | 35 | 0 | 30 | 80 | 65 | 70 | 50 | 0 |
| Cocklebur | 0 | — | — | — | — | — | — | — |
| Corn | 0 | 0 | 0 | 0 | 0 | 0 | 0 | 0 |
| Crabgrass, Brazil | — | — | — | — | — | 65 | 50 | 0 |
| Crabgrass, Large | 0 | 0 | 0 | 0 | 0 | 0 | 0 | 0 |
| Dayflower, VA | 0 | — | 0 | 0 | 0 | 0 | 0 | 0 |
| Field Bindweed | 0 | 0 | 65 | 0 | 30 | 0 | 0 | 0 |
| Foxtail, Giant | 0 | 0 | 35 | 0 | 0 | 0 | 0 | 0 |
| Foxtail, Green | 15 | 0 | 0 | 0 | 0 | 0 | 0 | 0 |
| Goosegrass | 0 | 0 | 35 | 0 | 50 | 0 | 0 | 0 |
| Johnsongrass | 20 | 0 | 35 | 0 | 30 | 0 | 0 | 0 |
| *Kochia* | 98 | 90 | 70 | 80 | 75 | 85 | 70 | 75 |
| Lambsquarters | — | — | — | — | — | 100 | 100 | 100 |
| Morningglory | 0 | 0 | 0 | 0 | 40 | 0 | 0 | 0 |
| Nightshade | — | — | — | — | — | 0 | 50 | 95 |
| Nutsedge, Yellow | — | 35 | 75 | 0 | 0 | 0 | 0 | 0 |
| *Panicum*, Fall | 0 | 0 | 0 | 0 | 0 | 0 | — | — |
| Pigweed, Palmer | 100 | 100 | 100 | 100 | 0 | 100 | 100 | 85 |
| Poinsettia, Wild | 0 | 0 | 0 | 0 | 0 | 0 | 0 | 0 |
| Ragweed | 75 | 100 | 95 | 100 | 98 | 70 | 80 | 30 |
| Ryegrass, Italian | 0 | 0 | 0 | 0 | 0 | 20 | 0 | 0 |
| Sandbur | 20 | 0 | 90 | 35 | 0 | 0 | 0 | 0 |
| Smartweed | 98 | — | 0 | 100 | 100 | — | — | — |
| Soybean | 0 | 0 | 0 | 0 | 0 | 0 | 0 | 0 |
| Surinam Grass | 0 | 0 | 0 | 0 | 0 | 0 | 0 | 0 |

TABLE E-continued

| | | | | | | | | |
|---|---|---|---|---|---|---|---|---|
| Velvetleaf | 50 | 100 | 80 | 100 | 100 | 100 | 80 | 100 |
| Waterhemp | 100 | 100 | 98 | 100 | 100 | 95 | 100 | 100 |

| | Compounds | | | | | | | | |
|---|---|---|---|---|---|---|---|---|---|
| 250 g ai/ha | 1 | 2 | 3 | 15 | 16 | 28 | 31 | 39 | 54 |
| | Preemergence | | | | | | | | |
| Arrowleaf Sida | 20 | 98 | 90 | 100 | 95 | 90 | 90 | 95 | 80 |
| Barnyardgrass | 0 | 0 | 0 | 0 | 0 | 0 | 0 | 0 | — |
| Beggarticks | 35 | 0 | 25 | 25 | 50 | 70 | 0 | 0 | 23 |
| Cocklebur | — | 0 | 0 | — | — | — | — | — | 0 |
| Corn | 0 | 0 | 0 | 0 | 0 | 0 | 0 | 0 | 0 |
| Crabgrass, Brazil | — | — | — | — | — | 35 | 0 | 0 | — |
| Crabgrass, Large | 0 | 0 | 0 | 0 | 0 | 0 | 0 | 0 | — |
| Dayflower, VA | 0 | — | 0 | — | 0 | 0 | 0 | 0 | 0 |
| Field Bindweed | 0 | 0 | 0 | 0 | 0 | 0 | 0 | 0 | 0 |
| Foxtail, Giant | 0 | 0 | 15 | 0 | 0 | 0 | 0 | 0 | — |
| Foxtail, Green | 0 | 0 | 0 | 0 | 0 | 0 | 0 | 0 | — |
| Goosegrass | 0 | 0 | 35 | 0 | 40 | 0 | 0 | 0 | — |
| Johnsongrass | 20 | 0 | 35 | 0 | 0 | 0 | 0 | 0 | — |
| *Kochia* | 50 | 65 | 50 | 75 | 50 | 40 | 50 | 65 | 28 |
| Lambsquarters | — | — | — | — | — | 100 | 100 | 90 | 86 |
| Morningglory | 0 | 0 | 0 | 0 | 0 | 0 | 0 | 0 | 12 |
| Nightshade | — | — | — | — | — | 0 | 0 | 100 | 0 |
| Nutsedge, Yellow | 0 | 40 | — | 0 | 0 | 0 | 0 | 0 | — |
| *Panicum*, Fall | 0 | 0 | 0 | 0 | 0 | 0 | — | 0 | — |
| Pigweed, Palmer | 20 | 0 | 50 | 65 | 0 | 25 | 98 | 90 | 95 |
| Poinsettia, Wild | — | 0 | 0 | 0 | 0 | 0 | 0 | 0 | 23 |
| Ragweed | 75 | 100 | 100 | 95 | 90 | 65 | 50 | 65 | 62 |
| Ryegrass, Italian | 0 | 0 | 0 | 0 | 0 | 10 | 0 | 0 | — |
| Sandbur | 20 | 0 | 15 | 40 | 0 | 0 | 0 | 0 | — |
| Smartweed | 98 | 0 | 0 | 100 | 100 | — | — | — | 0 |
| Soybean | 0 | 0 | — | 0 | 0 | 0 | 0 | 0 | 12 |
| Surinam Grass | 0 | 0 | 0 | 0 | 0 | 0 | 0 | 0 | — |
| Velvetleaf | 35 | 0 | 40 | 65 | 100 | 40 | 80 | 90 | 78 |
| Waterhemp | 60 | 65 | 85 | 75 | 100 | 95 | 100 | 100 | 99 |

| | Compounds | | | | | | | | |
|---|---|---|---|---|---|---|---|---|---|
| 125 g ai/ha | 1 | 2 | 3 | 15 | 16 | 28 | 31 | 39 | 54 |
| | Preemergence | | | | | | | | |
| Arrowleaf Sida | 25 | 50 | 70 | 90 | 90 | 75 | 80 | 90 | 43 |
| Barnyardgrass | 0 | 0 | 0 | 0 | 0 | 0 | 0 | 0 | — |
| Beggarticks | 0 | 0 | 25 | 0 | 25 | 40 | 0 | 0 | 0 |
| Cocklebur | — | 0 | — | 0 | — | — | — | — | 0 |
| Corn | 0 | 0 | 0 | 0 | 0 | 0 | 0 | 0 | 0 |
| Crabgrass, Brazil | — | — | — | — | — | 0 | 0 | 0 | — |
| Crabgrass, Large | 0 | 0 | 0 | 0 | 0 | 0 | 0 | 0 | — |
| Dayflower, VA | 0 | — | 0 | — | 0 | 0 | 0 | 0 | 0 |
| Field Bindweed | 0 | 0 | 0 | 0 | 0 | 0 | 0 | 0 | 0 |
| Foxtail, Giant | 0 | 0 | 0 | 0 | 0 | 20 | 0 | 0 | — |
| Foxtail, Green | 0 | 0 | 0 | 0 | 0 | 0 | 0 | 0 | — |
| Goosegrass | 0 | 0 | 0 | 0 | 0 | 0 | 0 | 0 | — |
| Johnsongrass | 0 | 0 | 0 | 0 | 0 | 0 | 0 | 0 | — |
| *Kochia* | 0 | 0 | 25 | 20 | 0 | 40 | 25 | 30 | 0 |
| Lambsquarters | — | — | — | — | — | 100 | 100 | 95 | 68 |
| Morningglory | 0 | 0 | 0 | 0 | 20 | 0 | 0 | 0 | 7 |
| Nightshade | — | — | — | — | — | 0 | 0 | 0 | 0 |
| Nutsedge, Yellow | 0 | 50 | 35 | 10 | 35 | 0 | 0 | 0 | — |
| *Panicum*, Fall | 0 | 0 | 0 | 0 | 0 | 0 | 0 | — | — |
| Pigweed, Palmer | 25 | 0 | 65 | 0 | 0 | 0 | 70 | 50 | 86 |
| Poinsettia, Wild | 0 | 0 | 0 | 0 | 0 | 0 | 0 | 0 | 80 |
| Ragweed | — | 0 | 0 | 0 | 85 | 30 | 35 | 0 | 35 |
| Ryegrass, Italian | 0 | 0 | 0 | 0 | 0 | 0 | 0 | 0 | — |
| Sandbur | 0 | 0 | 15 | 50 | 0 | 0 | 0 | 0 | — |
| Smartweed | 98 | 0 | 0 | 0 | 100 | — | — | — | 0 |
| Soybean | 0 | 0 | 0 | 0 | 0 | 0 | 0 | 0 | 0 |
| Surinam Grass | 0 | 0 | 0 | 0 | 0 | 0 | 0 | 0 | — |
| Velvetleaf | 50 | 0 | 35 | 35 | 85 | 0 | 50 | 75 | 87 |
| Waterhemp | 60 | 30 | 75 | 90 | 70 | 65 | 90 | 95 | 96 |

TABLE E-continued

| 62 g ai/ha | Compounds | | | | | | | |
|---|---|---|---|---|---|---|---|---|
| | 1 | 2 | 3 | 15 | 16 | 28 | 31 | 39 |
| Preemergence | | | | | | | | |
| Arrowleaf Sida | 25 | 35 | 40 | 30 | 35 | 20 | 30 | 0 |
| Barnyardgrass | 0 | 0 | 0 | 0 | 0 | 0 | 0 | 0 |
| Beggarticks | 0 | 0 | 0 | 0 | 0 | 0 | 0 | 0 |
| Cocklebur | — | 0 | — | 0 | — | — | — | — |
| Corn | 0 | 0 | 0 | 0 | 0 | 0 | 0 | 0 |
| Crabgrass, Brazil | — | — | — | — | — | 0 | 0 | 0 |
| Crabgrass, Large | 0 | 0 | 0 | 0 | 0 | 0 | 0 | 0 |
| Dayflower, VA | — | 0 | — | 0 | 0 | 0 | 0 | 0 |
| Field Bindweed | 0 | 0 | 0 | 0 | 0 | 0 | 0 | 0 |
| Foxtail, Giant | 0 | 0 | 0 | 0 | 0 | 0 | 0 | 0 |
| Foxtail, Green | 0 | 0 | 0 | 0 | 0 | 0 | 0 | 0 |
| Goosegrass | 0 | 0 | 0 | — | 0 | 0 | 0 | 0 |
| Johnsongrass | 0 | 0 | 0 | 0 | 0 | 0 | 0 | 0 |
| *Kochia* | 0 | 0 | 20 | 40 | 0 | 20 | 35 | 0 |
| Lambsquarters | — | — | — | — | — | 95 | 0 | 90 |
| Morningglory | 0 | 0 | 0 | 0 | 20 | 0 | 0 | 0 |
| Nightshade | — | — | — | — | — | 0 | 0 | 0 |
| Nutsedge, Yellow | 0 | — | 50 | 35 | 20 | 0 | 0 | 0 |
| *Panicum*, Fall | 0 | 0 | 0 | 0 | 0 | 0 | 0 | 0 |
| Pigweed, Palmer | 20 | 0 | 20 | 0 | 0 | 0 | 0 | 20 |
| Poinsettia, Wild | 0 | 0 | — | — | 0 | 0 | 0 | 0 |
| Ragweed | — | — | 0 | 0 | 0 | 0 | 0 | 60 |
| Ryegrass, Italian | 0 | 0 | 0 | 0 | 0 | 0 | 0 | 0 |
| Sandbur | 0 | 0 | 0 | 30 | 0 | 0 | 0 | 0 |
| Smartweed | — | — | 0 | 0 | 0 | — | — | — |
| Soybean | 0 | — | 0 | 0 | 0 | 0 | 0 | 0 |
| Surinam Grass | 0 | 0 | 0 | 0 | 0 | 0 | 0 | 0 |
| Velvetleaf | 40 | 0 | 20 | 25 | 40 | 0 | 65 | 15 |
| Waterhemp | 20 | — | 50 | 70 | 30 | 0 | 80 | 85 |

| 31 g ai/ha | Compounds | | | | | |
|---|---|---|---|---|---|---|
| | 1 | 2 | 3 | 15 | 16 | 28 |
| Preemergence | | | | | | |
| Arrowleaf Sida | 20 | 35 | 0 | 25 | 25 | 0 |
| Barnyardgrass | — | 0 | 0 | 0 | 0 | 0 |
| Beggarticks | 0 | 0 | 0 | 0 | 0 | 0 |
| Cocklebur | — | 0 | 0 | 0 | — | — |
| Corn | 0 | 0 | 0 | 0 | 0 | 0 |
| Crabgrass, Brazil | — | — | — | — | — | 0 |
| Crabgrass, Large | 0 | 0 | 0 | 0 | 0 | 0 |
| Dayflower, VA | 0 | — | — | 0 | 0 | 0 |
| Field Bindweed | 0 | 0 | 0 | 0 | 0 | 0 |
| Foxtail, Giant | 0 | 0 | 0 | 0 | 0 | 0 |
| Foxtail, Green | 0 | 0 | 0 | 0 | 0 | 0 |
| Goosegrass | 0 | 0 | 0 | 0 | 0 | 0 |
| Johnsongrass | 0 | 0 | 0 | 0 | 0 | 0 |
| *Kochia* | 0 | 0 | 0 | 0 | 0 | 15 |
| Lambsquarters | — | — | — | — | — | 0 |
| Morningglory | 0 | 0 | 0 | — | 0 | 0 |
| Nightshade | — | — | — | — | — | 0 |
| Nutsedge, Yellow | 0 | 0 | — | 15 | 0 | 0 |
| *Panicum*, Fall | 0 | 0 | 0 | 0 | 0 | 0 |
| Pigweed, Palmer | 0 | 0 | 0 | 0 | 0 | 0 |
| Poinsettia, Wild | 0 | — | — | — | 0 | 0 |
| Ragweed | 50 | 0 | 0 | 0 | 0 | 0 |
| Ryegrass, Italian | 0 | 0 | 0 | 0 | 0 | 0 |
| Sandbur | 0 | 0 | 0 | 0 | 0 | 0 |
| Smartweed | 0 | 0 | 0 | 0 | 0 | — |
| Soybean | 0 | — | 0 | 0 | 0 | 0 |
| Surinam Grass | 0 | 0 | 0 | 0 | 0 | 0 |
| Velvetleaf | 35 | 0 | 20 | 20 | 0 | 0 |
| Waterhemp | 0 | 0 | 0 | 0 | 0 | 0 |

Test H

This test evaluated the effect of mixtures of compound 39 with three commercial herbicides on five plant species. Seeds of plant species selected from corn (ZEAMD, *Zea mays*), soybean (GLXMA, *Glycine max*), palmer pigweed (AMAPA, *Amaranthus palmeri*), waterhemp (common waterhemp, AMATA, *Amaranthus rudis*), and Kochia (KCHSC, *Kochia scoparia*) were planted in pots containing Redi-Earth® planting medium (Scotts Company, 14111 Scottslawn Road, Marysville, Ohio 43041) comprising spaghnum peat moss, vermiculite, wetting agent and starter nutrients and treated with postemergence applications of test chemicals formulated in a non-phytotoxic solvent mixture which included a surfactant and applied using a volume of 299 L/ha. Each treatment was replicated four times. Treated plants and controls were maintained in a greenhouse using supplemental lighting to maintain a photoperiod of about 16 h; daytime and nighttime temperatures were about 24-30° C. and 19-21° C., respectively. Nutrients were applied using a balanced fertilizer applied through the watering system. At 14 days after treatment, all species were compared to controls and visually evaluated. Plant response ratings were calculated as the mean of the four replicates, are summarized in Tables H1 through H6, and are based on a scale of 0 to 100 where 0 is no effect and 100 is complete control. A dash (-) response means no test result.

Colby's Equation was used to determine the herbicidal effects expected from the mixtures. Colby's Equation (Colby, S. R. "Calculating Synergistic and Antagonistic Responses of Herbicide Combinations," Weeds, 15(1), pp 20-22 (1967)) calculates the expected additive effect of herbicidal mixtures and for two active ingredients is of the form:

$$P_{a+b} = P_a + P_b - (P_a P_b / 100)$$

where
$P_{a+b}$ is the percentage effect of the mixture expected from additive contribution of the individual components:
$P_a$ is the observed percentage effect of the first active ingredient at the same use rate as in the mixture, and
$P_b$ is the observed percentage effect of the second active ingredient at the same use rate as in the mixture.

In the following Tables, rates are shown in grams of active ingredient per hectare (g a.i./ha); "Obsd." is the observed effect. "Exp." is the expected effect calculated from Colby's Equation.

TABLE H1

Observed and Expected Results from Compound 39 Alone and in Combination with Chlorimuron-ethyl

| Application Rate (g a.i./ha) | | ZEAMD | | GLXMA | | AMAPA | | AMATA | | KCHSC | |
|---|---|---|---|---|---|---|---|---|---|---|---|
| Cmpd 39 | Chlorimuron-ethyl | Obsd. | Exp. | Obsd. | Exp. | Obsd. | Exp. | Obsd. | Exp. | Obsd. | Exp. |
| 31 | — | 0 | — | 0 | — | 86 | — | 88 | — | 60 | — |
| 62 | — | 0 | — | 0 | — | 79 | — | 79 | — | 64 | — |
| — | 1 | 33 | — | 0 | — | 86 | — | 76 | — | 97 | — |
| 31 | 1 | 29 | 33 | 4 | 0 | 99 | 98 | 84 | 97 | 97 | 99 |
| 62 | 1 | 36 | 33 | 0 | 0 | 98 | 97 | 93 | 95 | 100 | 99 |

TABLE H2

Observed and Expected Results from Compound 39 Alone and in Combination with Nicosulfuron

| Application Rate (g a.i./ha) | | ZEAMD | | GLXMA | | AMAPA | | AMATA | | KCHSC | |
|---|---|---|---|---|---|---|---|---|---|---|---|
| Cmpd 39 | Nicosulfuron | Obsd. | Exp. | Obsd. | Exp. | Obsd. | Exp. | Obsd. | Exp. | Obsd. | Exp. |
| 31 | — | 0 | — | 0 | — | 86 | — | 88 | — | 60 | — |
| 62 | — | 0 | — | 0 | — | 76 | — | 79 | — | 64 | — |
| — | 1 | 0 | — | 51 | — | 100 | — | 78 | — | 89 | — |
| 31 | 1 | 0 | 0 | 9 | 51 | 91 | 100 | 90 | 97 | 93 | 96 |
| 62 | 1 | 0 | 0 | 43 | 51 | 100 | 100 | 91 | 95 | 97 | 96 |

TABLE H3

Observed and Expected Results from Compound 39 Alone and in Combination with Mesotrione

| Application Rate (g a.i./ha) | | ZEAMD | | GLXMA | | AMAPA | | AMATA | | KCHSC | |
|---|---|---|---|---|---|---|---|---|---|---|---|
| Cmpd 39 | Mesotrione | Obsd. | Exp. | Obsd. | Exp. | Obsd. | Exp. | Obsd. | Exp. | Obsd. | Exp. |
| 31 | — | 0 | — | 0 | — | 86 | — | 88 | — | 60 | — |
| 62 | — | 0 | — | 0 | — | 79 | — | 79 | — | 64 | — |
| — | 4 | 0 | — | 64 | — | 78 | — | 79 | — | 79 | — |
| 31 | 4 | 0 | 0 | 66 | 64 | 97 | 97 | 95 | 97 | 91 | 92 |
| 62 | 4 | 0 | 0 | 66 | 64 | 99 | 95 | 99 | 96 | 96 | 92 |

TABLE H4

Observed and Expected Results from Compound 39 Alone and in Combination with Chlorimuron-ethyl

| Application Rate (g a.i./ha) | | ZEAMD | | GLXMA | | AMAPA | | AMATA | | KCHSC | |
|---|---|---|---|---|---|---|---|---|---|---|---|
| Cmpd 39 | Chlorimuron-ethyl | Obsd. | Exp. | Obsd. | Exp. | Obsd. | Exp. | Obsd. | Exp. | Obsd. | Exp. |
| 16 | — | 0 | — | 0 | — | 55 | — | 75 | — | 47 | — |
| 31 | — | 0 | — | 0 | — | 78 | — | 83 | — | 47 | — |
| — | 0.25 | 0 | — | 0 | — | 65 | — | 77 | — | 88 | — |
| 16 | 0.25 | 0 | 0 | 0 | 0 | 53 | 84 | 78 | 94 | 87 | 94 |
| 31 | 0.25 | 0 | 0 | 2 | 0 | 67 | 92 | 82 | 96 | 87 | 94 |

TABLE H5

Observed and Expected Results from Compound 39 Alone and in Combination with Nicosulfuron

| Application Rate (g a.i./ha) | | ZEAMD | | GLXMA | | AMAPA | | AMATA | | KCHSC | |
|---|---|---|---|---|---|---|---|---|---|---|---|
| Cmpd 39 | Nicosulfuron | Obsd. | Exp. | Obsd. | Exp. | Obsd. | Exp. | Obsd. | Exp. | Obsd. | Exp. |
| 16 | — | 0 | — | 0 | — | 55 | — | 75 | — | 47 | — |
| 31 | — | 0 | — | 0 | — | 78 | — | 83 | — | 47 | — |
| — | 0.25 | 0 | — | 0 | — | 3 | — | 63 | — | 43 | — |
| 16 | 0.25 | 0 | 0 | 2 | 0 | 53 | 56 | 82 | 91 | 62 | 70 |
| 31 | 0.25 | 0 | 0 | 0 | 0 | 63 | 79 | 80 | 94 | 58 | 70 |

TABLE H6

Observed and Expected Results from Compound 39 Alone and in Combination with Mesotrione

| Application Rate (g a.i./ha) | | ZEAMD | | GLXMA | | AMAPA | | AMATA | | KCHSC | |
|---|---|---|---|---|---|---|---|---|---|---|---|
| Cmpd 39 | Mesotrione | Obsd. | Exp. | Obsd. | Exp. | Obsd. | Exp. | Obsd. | Exp. | Obsd. | Exp. |
| 16 | — | 0 | — | 0 | — | 55 | — | 75 | — | 47 | — |
| 31 | — | 0 | — | 0 | — | 78 | — | 83 | — | 47 | — |
| — | 4 | 0 | — | 62 | — | 72 | — | 92 | — | 72 | — |
| 16 | 4 | 0 | 0 | 53 | 62 | 68 | 87 | 83 | 98 | 80 | 85 |
| 31 | 4 | 0 | 0 | 57 | 62 | 78 | 94 | 97 | 99 | 80 | 85 |

What is claimed is:
1. A compound selected from the group consisting of
[3-(3,5-dichlorophenyl)-1-methyl-1H-pyrazol-4-yl]phenylmethanone;
[3-(3,5-dichlorophenyl)-1-ethyl-1H-pyrazol-4-yl]phenylmethanone;
[3-(3,5-dichlorophenyl)-1-propyl-1H-pyrazol-4-yl]phenylmethanone;
[3-(3,5-dichlorophenyl)-1-(2-propyn-1-yl)-1H-pyrazol-4-yl]phenylmethanone;
N-[[3-(3,5-dichlorophenyl)-1H-pyrazol-4-yl]phenylmethylene]-1-pyrrolidinamine;
[3-(3,5-dichlorophenyl)-1-(hydroxymethyl)-1H-pyrazol-4-yl]phenylmethanone;
1-[4-benzoyl-3-(3,5-dichlorophenyl)-1H-pyrazol-1-yl]-2-methoxyethanone;
3-(3,5-dichlorophenyl)-1-[(trifluoromethyl)sulfonyl]-1H-pyrazol-4-yl]phenylmethanone;
3-(3,5-dichlorophenyl)-4-(diethoxyphenylmethyl)-1H-pyrazole; and
3-(3,5-dichlorophenyl)-4-(dimethoxyphenylmethyl)-1H-pyrazole.

2. A herbicidal composition comprising a compound of claim 1 and at least one component selected from the group consisting of surfactants, solid diluents and liquid diluents.

3. A herbicidal composition comprising a compound of claim 1, at least one additional active ingredient selected from the group consisting of other herbicides and herbicide safeners, and at least one component selected from the group consisting of surfactants, solid diluents and liquid diluents.

4. A herbicidal mixture comprising (a) a compound of claim 1, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics and (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, metam, methyldymron, oleic acid, oxaziclomefone, pelargonic acid and pyributicarb, and (b16) herbicide safeners; and salts of compounds of (b1) through (b16).

5. A method for controlling the growth of undesired vegetation comprising contacting the vegetation or its environment with a herbicidally effective amount of a compound of claim 1.

* * * * *